(12) United States Patent
Hilpert et al.

(10) Patent No.: US 9,388,197 B2
(45) Date of Patent: Jul. 12, 2016

(54) HETEROCYCLIC AMIDE DERIVATIVES AS P2X7 RECEPTOR ANTAGONISTS

(71) Applicant: ACTELION PHARMACEUTICALS LTD, Allschwil (CH)

(72) Inventors: Kurt Hilpert, Allschwil (CH); Francis Hubler, Allschwil (CH); Dorte Renneberg, Allschwil (CH); Simon Stamm, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/762,692

(22) PCT Filed: Jan. 21, 2014

(86) PCT No.: PCT/IB2014/058424
§ 371 (c)(1),
(2) Date: Jul. 22, 2015

(87) PCT Pub. No.: WO2014/115072
PCT Pub. Date: Jul. 31, 2014

(65) Prior Publication Data
US 2015/0361096 A1    Dec. 17, 2015

(30) Foreign Application Priority Data
Jan. 22, 2013   (EP) ..................... 13152217

(51) Int. Cl.
C07D 277/64   (2006.01)
C07D 277/66   (2006.01)
C07D 277/68   (2006.01)
C07D 277/82   (2006.01)
C07D 513/04   (2006.01)
C07D 277/60   (2006.01)

(52) U.S. Cl.
CPC ............ *C07D 513/04* (2013.01); *C07D 277/60* (2013.01); *C07D 277/64* (2013.01); *C07D 277/66* (2013.01); *C07D 277/68* (2013.01); *C07D 277/82* (2013.01)

(58) Field of Classification Search
USPC .................................. 548/153, 180
See application file for complete search history.

(56) References Cited

U.S. PATENT DOCUMENTS 4,033,977 A * 7/1977 Philipp ................ C07D 277/30
544/368
2002/0156287 A1  10/2002 Rudolph et al.
2007/0281939 A1  12/2007 Dombrowski et al.
2012/0157494 A1   6/2012 Harris, III et al.

FOREIGN PATENT DOCUMENTS

| | | |
|---|---|---|
| EP | 2243772 | 10/2010 |
| WO | WO 00/61569 | 10/2000 |
| WO | WO 01/42194 | 6/2001 |
| WO | WO 01/44170 | 6/2001 |
| WO | WO 01/94338 | 12/2001 |
| WO | WO 03/041707 | 5/2003 |
| WO | WO 03/042190 | 5/2003 |
| WO | WO 03/042191 | 5/2003 |
| WO | WO 03/080579 | 10/2003 |
| WO | WO 2004/058270 | 7/2004 |
| WO | WO 2004/058731 | 7/2004 |
| WO | WO 2004/074224 | 9/2004 |
| WO | WO 2004/099146 | 11/2004 |
| WO | WO 2004/106305 | 12/2004 |
| WO | WO 2005/009968 | 2/2005 |
| WO | WO 2005/111003 | 11/2005 |
| WO | WO 2006/025783 | 3/2006 |
| WO | WO 2006/059945 | 6/2006 |
| WO | WO 2006/080884 | 8/2006 |
| WO | WO 2006/102610 | 9/2006 |
| WO | WO 2007/055374 | 5/2007 |
| WO | WO 2007/109154 | 9/2007 |
| WO | WO 2007/109160 | 9/2007 |
| WO | WO 2007/109172 | 9/2007 |
| WO | WO 2007/109182 | 9/2007 |
| WO | WO 2007/109192 | 9/2007 |
| WO | WO 2007/109201 | 9/2007 |
| WO | WO 2007/141267 | 12/2007 |

(Continued)

OTHER PUBLICATIONS

Golub et al., Science, vol. 286, Oct. 15, 1999, pp. 531-537.*

(Continued)

*Primary Examiner* — Laura L. Stockton
(74) *Attorney, Agent, or Firm* — Hoxie & Associates LLC

(57) ABSTRACT

The invention relates to heterocyclic amide derivatives of formula (I),

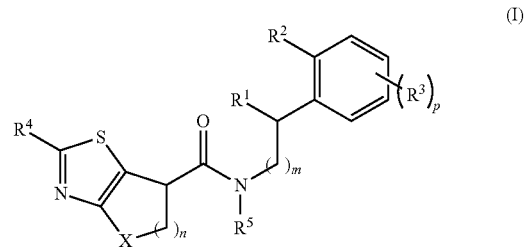

wherein $R^1$, $R^2$, $R^3$, $R^4$, $R^5$, n, m, p and X are as defined in the description, their preparation and their use as pharmaceutically active compounds.

19 Claims, No Drawings

(56) References Cited

FOREIGN PATENT DOCUMENTS

| WO | WO 2007/141269 | 12/2007 |
|---|---|---|
| WO | WO 2008/003697 | 1/2008 |
| WO | WO 2008/066789 | 6/2008 |
| WO | WO 2008/094473 | 8/2008 |
| WO | WO 2008/112205 | 9/2008 |
| WO | WO 2008/114002 | 9/2008 |
| WO | WO 2008/116814 | 10/2008 |
| WO | WO 2008/116845 | 10/2008 |
| WO | WO 2008/119685 | 10/2008 |
| WO | WO 2008/119825 | 10/2008 |
| WO | WO 2008/124153 | 10/2008 |
| WO | WO 2008/125600 | 10/2008 |
| WO | WO 2008/138876 | 11/2008 |
| WO | WO 2009/012482 | 1/2009 |
| WO | WO 2009/023623 | 2/2009 |
| WO | WO 2009/070116 | 6/2009 |
| WO | WO 2009/074518 | 6/2009 |
| WO | WO 2009/074519 | 6/2009 |
| WO | WO 2009/077362 | 6/2009 |
| WO | WO 2009/077559 | 6/2009 |
| WO | WO 2009/108551 | 9/2009 |
| WO | WO 2009/118175 | 10/2009 |
| WO | WO 2009/132000 | 10/2009 |
| WO | WO 2010/118921 | 10/2010 |
| WO | WO 2011/054947 | 5/2011 |
| WO | WO 2012/114268 | 8/2012 |
| WO | WO 2012/163792 | 12/2012 |
| WO | WO 2013/014587 | 1/2013 |
| WO | WO 2013/108227 | 7/2013 |
| WO | WO 2014/057078 | 4/2014 |
| WO | WO 2014/057080 | 4/2014 |
| WO | WO 2014/091415 | 6/2014 |
| WO | WO 2014/097140 | 6/2014 |
| WO | WO 2014/115078 | 7/2014 |

OTHER PUBLICATIONS

Abberley, et al. "Identification of 2-oxo-n-(phenylmethyl)-4-imidazolidinecarboxamide antagonists of the P2X7 receptor" Bioorganic & Medicinal Chemistry Letters, vol. 20, (Sep. 2010) pp. 6370-6374.

Abdi, et al. "Discovery and structure-activity relationships of a series of pyroglutamic acid amide antagonists of the P2X7 receptor" Bioorganic & Medicinal Chemistry Letters, vol. 20, (Jul. 2010) pp. 5080-5084.

Arbeloa, et al. "P2X7 receptor blockade prevents ATP excitotoxicity in neurons and reduces brain damage after ischemia" Neurobiol Dis vol. 45, No. 3 (2012) pp. 954-961.

Badarau, et. al. "Synthesis of 3-Amino-8-azachromans and 3-Amino-7-azabenzofurans via Inverse Electron Demand Diels-Alder Reaction" Eur. J. Org. Chem., vol. 20 (2009) pp. 3619-3627.

Bartlett, "The P2X7 Receptor Channel: Recent Developments and the Use of P2X7 Antagonists in Models of Disease" Pharmacol. Rev., vol. 66 (Jul. 2014) pp. 638-675.

Chambers, et al. "Synthesis and structure-activity relationships of a series of (1H-pyrazol-4-yl)a-cetamide antagonists of the P2X7 recepter" Bioorganic & Medicinal Chemistry Letters, vol. 20 (Mar. 2010) pp. 3161-3164.

Chen, et al. "Discovery of 2-chloro-n-((4,4-difluoro-1-hdroxycyclohexyl)methyl)-5-(5-fluoropyrimidin-2-yl)benzamide as a potent and CNS penetrable P2X7 receptor antagonist" Bioorganic & Medicinal Chemistry Letters, vol. 20, (Mar. 2010) pp. 3107-3111.

Chessell, et al. "Disruption of the P2X7 purinoceptor gene abolishes chronic inflammatory and neuropathic pain" Pain, vol. 114 (Jan. 2005) pp. 386-396.

Damia, "Contemporary pre-clinical development of anticancer agents—What are the optimal preclinical models?" European Journal of Cancer, vol. 45 (2009) pp. 2768-2781.

Dell'Antonio, et al. "Antinociceptive effect of a new P(2Z)/P2X7 antagonist, oxidized ATP, in arthritic rats" Neurosci Lett., vol. 327, No. 2 (2002) pp. 87-90.

D'Onofrio, "Advances in the identification of g-secretase inhibitors for the treatment of Alzheimer's disease" Expert Opinion on Drug Discovery, vol. 7 (2012) pp. 20-37.

Degraffenreid, et al. "An Efficient and Scalable One-Pot Double Michael Addition—Dieckmann Condensation for the Synthesis of 4,4-Disubstituted Cyclohexane β-keto Esters" J. Org. Chem., vol. 72, No. 19 (2007) pp. 7455-7458.

Deuchars, et al. "Neuronal P2x7 Receptors Are Targeted to Presynaptic Terminals in the Central and Peripheral Nervous Systems" The Journal of Neuroscience, vol. 21, No. 18 (Sep. 2001) pp. 7143-7152.

Duplantier, et al. "Optimization of the Physicochemical and Pharmacokinetic Attributes in a 6-azauracil Series of P2X7 Receptor Antagonists Leading to the Discovery of the Clinical Candidate ce-224,535" Bioorganic & Medicinal Chemistry Letters, vol. 21 (Apr. 2011) pp. 3708-3711.

Eltom, et al., "P2X7 receptor and caspase 1 activation are central to airway inflammation observed after exposure to tobacco smoke" PLoS One, vol. 6, No. 9 (2011) e24097.

Engel, et al. "P2X7 receptor in epilepsy; role in pathophysiology and potential targeting for seizure control" Int J Physiol Pathophysiol Pharmacol, vol. 4, No. 4 (2012) pp. 174-187.

Eser, et al. "Safety and Efficacy of an Oral Inhibitor of the Purinergic Receptor P2X7 in Adult Patients with Moderately to Severely Active Crohn's Disease: A Randomized Placebo-controlled, Double-blind, Phase IIa Study" Inflamm Bowel Dis. vol. 0, No. 0 (Mar. 2015).

Ferrari, et al. "ATP-Mediated Cytotoxicity in Microglial Cells" Neuropharmacology, vol. 36, No. 9 (Jul. 1997) pp. 1295-1301.

Furber, et al. "Discovery of Potent and Selective Adamantane-Based Small-Molecule P2X7 receptor Antagonists/Interleukin-1βInhibitors" Journal of Medicinal Chemistry, vol. 50 (Oct. 2007) pp. 5882-5885.

Gandelman, et al. "Extracellular ATP and the P2X7 receptor in astrocyte-mediated motor neuron death: implications for amyotrophic lateral sclerosis." J Neuroinflammation, vol. 7, No. 33 (2010), 31 pages.

Gulbransen, et al. "Activation of neuronal P2X7 receptor-pannexin-1 mediates death of enteric neurons during colitis" Nat Med, vol. 18 No. 4 (2012) pp. 600-604.

Gould, "Salt selection for basic drugs" International Journal of Pharmaceutics, vol. 33 (May 1986) pp. 201-217.

Greene, et al. "Protective Groups in Organic Synthesis" Wiley Interscience (1999).

Greenwood-Van Meerveld, "Animal models of gastrointestinal and liver diseases. Animal models of visceral pain: pathophysiology, translational relevance, and challenges" Am. J. Physiol. Gastrointest Liver Physiol., vol. 308 (2015) pp. G885-G903.

Guile, et al. "Antagonists of the P2X7 Receptor. From Lead Identification to Drug Development" Journal of Medicinal Chemistry, vol. 52, No. 10 (May 2009) pp. 3123-3141.

Honore, et al. "A-740003 [N-(1-{[(cyanoimino)(5-quinolinylamino) methyl]amino}-2,2-dimethylpropy1)-2-(3,4-dimethoxyphenyl)acetamide], a novel and selective P2X7 receptor antagonist, dose-dependently reduces neuropathic pain in the rat" J Pharmacol Exp Ther, vol. 319, No. 3 (2006) pp. 1376-1385.

Hook, "Neuroproteases in Peptide Neurotransmission and Neurodegenerative Diseases Applications to Drug Discovery Research" Biodrugs, vol. 20 (2006) pp. 105-119.

Hutchison, et al. "Stereoselective Synthesis of a Conformationally Defined Cyclohexyl Carnitine Analogue That Binds CPT-1 with High Affinity" Bioorganic & Medicinal Chemistry, vol. 7 (Dec. 1999) pp. 1505-1511.

Jhee, et al., "B-amyloid therapies in Alzheimer's disease" Expert Opinion on Ivestigational Drugs, vol. 10 (2001) pp. 593-605.

Johnson, et al., "Relationships between drug activity in NCI preclinical in vitro and in vivo models and early clinical trials" British Journal of Cancer, vol. 84 (2001) pp. 1424-1431.

Julien, "Transgenic mouse models of amyotrophic lateral sclerosis" Biochimica et Biophysica Acta 1762 (2006) pp. 1013-1024.

Keating, et al. (2011). "P2X7 receptor-dependent intestinal afferent hypersensitivity in a mouse model of postinfectious irritable bowel syndrome." J Immunol vol. 187, No. 3 (2011) pp. 1467-1474.

(56) References Cited

OTHER PUBLICATIONS

Kitamura, et al. "Powerful Chiral Phase-Transfer Catalysts for the Asymmetic Synthesis of α-Akyl and α,α-Dialkyl-α-amino Acids" Angewandte Chemie, vol. 44 (2005) pp. 1549-1551.
Lang, et al. "Oxidized ATP inhibits T-cell-mediated autoimmunity" Eur J Immunol., vol. 40, No. 9 (2010) pp. 2401-2408.
Le Bars, et al., "Animal Models of Nociception" Pharmacological Reviews, vol. 53, (2001) pp. 597-652.
Letavic, et al. "Synthesis and Pharmacological Characterization of Two Novel, Brain Penetrating P2X7 Antagonists" ACS Medicinal Chemistry Letters, vol. 4 (Mar. 2013) pp. 419-422.
Lovey, et al. "Isobenzofurans as Conformationally Constrained Miconazole Analogues with Improved Antifungal Potency" Journal of Medicinal Chemistry, vol. 35, No. 22 (1992) pp. 4221-4229.
Madsen-Duggan, et al. "Dihyrdo-pyrano[2,3-b] pyridines and tetrahydro-1,8-naphthyridines as CB1 receptor inverse agonists: Synthesis, SAR and biological evaluation" Bioorganic & Medicinal Chemistry Letters, vol. 20 (Apr. 2010) pp. 3750-3754.
Marcillo, "A reassessment of P2X7 receptor inhibition as a neuroprotective strategy in rat models of contusion injury" Experimental Neurology, vol. 233 (2012) pp. 687-692.
Mezzaroma, et al. "The inflammasome promotes adverse cardiac remodeling following acute myocardial infarction in the mouse" Proc Natl Acad Sci U S A, vol. 108, No. 49 (2011) pp. 19725-19730.
Morita, et al. "Furopyridines. VI. Preparation and Reactions of 2- and 3-Subsituted Furo [2,3-b] pyridines" J. Heterocyclic Chem., vol. 23 (1986) pp. 1465-1469.
Muller, et al. "A potential role for P2X7R in allergic airway inflammation in mice and humans" Am J Respir Cell Mol Biol vol. 44, No. 4 (2011) pp. 456-464.
North, "Molecular Physiology of P2X Receptors" Physiology Review, vol. 82 (Oct. 2002) pp. 1013-1067.
Ocana, "Preclinical development of molecular targeted agents for cancer" Nat. Rev. Clin. Oncol.vol. 8 (2011) pp. 200-209.
Online "DPT-Submission of Pure Compounds for Testing in the NCI Screen" and "NCI 60 Cell Line Screening On-Line Submission Flow Chart" http://dtp.nci.nih.gov/docs/misc/common_files/submit_compounds.html pp. 1-2 , Apr. 9, 2015.
Pastore, et al. "Stimulation of purinergic receptors modulates chemokine expression in human keratinocytes" J Invest Dermatol, vol. 127, No. 3 (2007) pp. 660-667.
Peng, et al. "Systemic administration of an antagonist of the ATP-sensitive receptor P2X7 improves recovery after spinal cord injury" Proc Natl Acad Sci U S A, vol. 106, No. 30 (2009) pp. 12489-12493.
Reid, "Epilepsy, energy deficiency and new therapeutic approaches including diet" Pharmacology & Therapeutics, vol. 144 (2014) pp. 192-201.
Remington, The Science and Practice of Pharmacy, 21$^{st}$ Edition (2005) Table of Contents.
Sanz, et al. "Activation of microglia by amyloid {beta} requires P2X7 receptor expression." J Immunol, vol. 182, No. 7 (2009) pp. 4378-4385.
Sharma, "Cell line-based platforms to evaluate the therapeutic efficacy of candidate anticancer agents" Nature Reviews Cancer, vol. 10 (Apr. 2010) pp. 241-253.
Simone, "Oncology: Introduction" Cecil Textbook of Medicine, 20$^{th}$ Edition, vol. 1 (1996) pp. 1004-1010.
Solle, et al. "Mechanisms of Signal Transduction: Altered Cytokine Production in Mice Lacking P2X7 receptors" The Journal of Biological Chemistry, vol. 276, No. 1 (Jan. 2001) pp. 125-132.
Sperlagh, et al. "Involvement of P2X7 Receptors in the regulation of neurotransmitter release in the rat hippocampus" Journal of Neurochemistry, vol. 81 (2002) pp. 1196-1211.
Sperlagh, "P2X7 receptor: and emerging target in central nervous system diseases" Trends in Pharmacological Sciences, vol. 35, No. 10 (Oct. 2014) pp. 537-547.
Stock, "Efficacy and Safety of CE-4224,535, an Antagonist of P2X7 Receptor, in Treatment of Patients with Rheumatoid Arthritis Inadequately Controlled by Methotrexate" The Journal of Rheumatology, vol. 39, No. 4 (2012) pp. 720-727.
Subramanyam, et al. "Discovery, Synthesis and SAR of azinyl- and azolylbenzamides Antagonists of the P2X7 receptor" Bioorganic & Medicinal Chemisty Letters, vol. 21 (2011) pp. 5475-5479.
Surprenant, et al. "The Cytolytic P2Z Receptor for Extracellular ATP Identified as a P2X Receptor (P2X7)" Science, vol. 272, No. 5262 ( May 1996) pp. 735-738.
Taylor, et al. "P2X7 deficiency attenuates renal injury in experimental glomerulonephritis" J Am Soc Nephrol vol. 20, No. 6 (2009) pp. 1275-1281.
Velcicky, et al. "Palladium-Catalyzed Cyanomethylation of Aryl Halides through Domino Suzuki Coupling-Isoxazole Fragmentation" Journal of the American Chemical Society, vol. 133 (Apr. 2011) pp. 6948-6951.
Virginio, et al. "Kinetics of cell lysis, dye uptake and permeability changes in cells expressing the rat P2X7 receptor" Journal of physiology, vol. 519.2 (May 1999) pp. 335-346.
Wang, et al. "Palladium-Catalyzed One-Pot Synthesis of 2-Alkyl-2-arylcyanoacetates" Journal Organic Chemistry, vol. 73, No. 4, (2008) pp. 1643-1645.
Wesselius, et al. "Role of purinergic receptor polymorphisms in human bone" Front Biosci (Landmark Ed) vol. 16 (2011) pp. 2572-2585.
Wiley, et al. "Transduction Mechanisms of P2Z Purinoceptors" Ciba Foundation Symposium, vol. 198 (1996) pp. 149-160 and 160-165.
Yu, et al. "Cellular localization of P2X7 receptor mRNA in the rat brain" Brain Research, vol. 1194 (2008) pp. 45-55.
Yuzwa, "O-GlcNAc and neurodegeneration: biochemical mechanisms and potential roles in Alzheimer's disease and beyond" Chem. Soc. Rev., vol. 43 (2014) 6839-6858.

* cited by examiner

HETEROCYCLIC AMIDE DERIVATIVES AS P2X7 RECEPTOR ANTAGONISTS

CROSS REFERENCE TO RELATED APPLICATIONS

This application is filed under 35 U.S.C. 371 as a U.S. National Phase Application of International Application No. PCT/IB2014/058424 filed Jan. 21, 2014, which claims the benefit of European application 13152217.9 filed Jan. 22, 2013.

The present invention relates to heterocyclic amide derivatives of formula (I) and their use as pharmaceuticals. The invention also concerns related aspects including processes for the preparation of the compounds, pharmaceutical compositions containing one or more compounds of formula (I), and especially their use as $P2X_7$ receptor antagonists.

The $P2X_7$ receptors (P2RX7) belong to the family of P2X ionotropic receptors that are activated by extracellular nucleotides, in particular adenosine triphosphate (ATP). P2RX7 is distinguished from other P2X family members by the high concentrations (mM range) of ATP required to activate it and its ability to form a large pore upon prolonged or repeated stimulation (North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). P2RX7 is present on many cell types, especially ones known to be involved in inflammatory and immune processes. This is reflected within both the periphery and the CNS as Lipopolysaccharide S (LPS) priming of monocytes and microglia followed by ATP stimulation has been shown to lead to the local release and processing of IL1β and other family members including IL18 through a P2RX7 mediated mechanism. Indeed mice lacking the P2X7 receptor are unable to release IL1β following LPS priming and ATP stimulation providing further evidence of its role in this pathway (Solle, M., Labasi, J. et al., J. Biol. Chem., 2001, 276(1), 125-32). In addition L-selectin shedding from monocytes, macrophages and lymphocytes, degranulation in mast cells and apoptosis in lymphocytes are all associated with P2RX7 stimulation. P2RX7 is also expressed on epithelial and endothelial cells (Ferrari, D., Chiozzi, P. et al., Neuropharmacology 1997, 36(9), 1295-301; Wiley, J. S., Chen, J. R. et al., Ciba Found Symp. 1996, 198, 149-60 and 160-5; North, R. A., Physiol. Rev. 2002, 82(4), 1013-67). In addition to its role in the periphery it may have an important function in neurotransmission within the CNS through its activation on postsynaptic and/or presynaptic central and peripheral neurons and glia (Deuchars, S. A., Atkinson, L. et al., J. Neurosci. 2001, 21(18), 7143-52; Sperlagh, B., Kofalvi, A. et al., J. Neurochem. 2002, 81(6), 1196-211). Recent data that has emerged using in situ hybridization demonstrated that P2X7 receptor mRNA was widely distributed throughout the rat brain. Specifically, among the areas of high P2X7mRNA expression noted were the piriform cortex, hippocampus, pontine nuclei and the anterior horn of the spinal cord (Yu, Y., Ugawa, S. et al., Brain. Res. 2008, 1194, 45-55). Hence there is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition a recent report suggests a link between P2RX7 and chronic, inflammatory and neuropathic pain (Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in treating neuropathic pain, chronic inflammatory pain, inflammation, and neurodegenerative conditions.

Indole carboxamide derivatives, which are also $P2X_7$ receptor antagonists, have been for instance disclosed in WO 2009/108551. Pyrazolyl-acetamide derivatives as $P2X_7$ receptor antagonists are described in WO 2008/138876 and in L. J. Chambers et al., Bioorg. Med. Chem. Lett., 2010, 20, 3161-3164; the article additionally discloses thiazolyl-acetamide derivatives. Other $P2X_7$ receptor antagonists with a heterocyclic amide structure have been disclosed in WO 2013/014587 and in WO 2013/108227.

Various embodiments of the invention are presented hereafter:

1) The present invention relates to heterocyclic amide derivatives of formula (I),

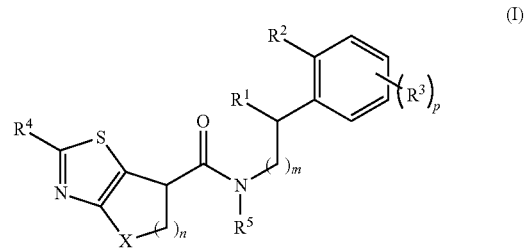

wherein
n represents 1, 2 or 3;
m represents 0, 1 or 2;
p represents 0, 1 or 2;
X represents —O— or —CH$_2$—;
$R^1$ represents hydrogen, (C$_1$-C$_2$)alkyl or hydroxy-(C$_1$-C$_2$)alkyl and $R^2$ represents hydrogen or halogen; or $R^1$ and $R^2$ together represent a —CH$_2$CH$_2$— or a —CH$_2$CH$_2$CH$_2$— group; each $R^3$ independently represents (C$_1$-C$_4$)alkyl, (C$_3$-C$_6$)cycloalkyl, (C$_1$-C$_4$)alkoxy, hydroxy-(C$_1$-C$_3$)alkyl, hydroxy-(C$_2$-C$_3$)alkoxy, hydroxy-(C$_2$-C$_3$)alkoxy(C$_1$-C$_2$) alkyl, (C$_1$-C$_2$)alkoxy-(C$_1$-C$_2$)alkyl, (C$_1$-C$_3$)fluoroalkyl, (C$_1$-C$_3$)fluoroalkoxy, cyano, halogen or phenoxy;
$R^4$ represents hydrogen, (C$_1$-C$_4$)alkyl, (C$_1$-C$_3$)fluoroalkyl, amino, halogen or phenyl; and
$R^5$ represents hydrogen or methyl;
and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

In this patent application, variably attached bonds may be used for substituents or groups. In such case it is meant that the substituent or group is attached to any carbon atom of the ring system to which the variable attached bond is drawn into, provided that said carbon atom is not already specifically substituted. For example, it is understood that any group $R^3$ may be attached to any carbon atom of the phenyl ring of formula (I) which is not already substituted. In case p represents 1, formula (I) therefore encompasses the following four formulas:

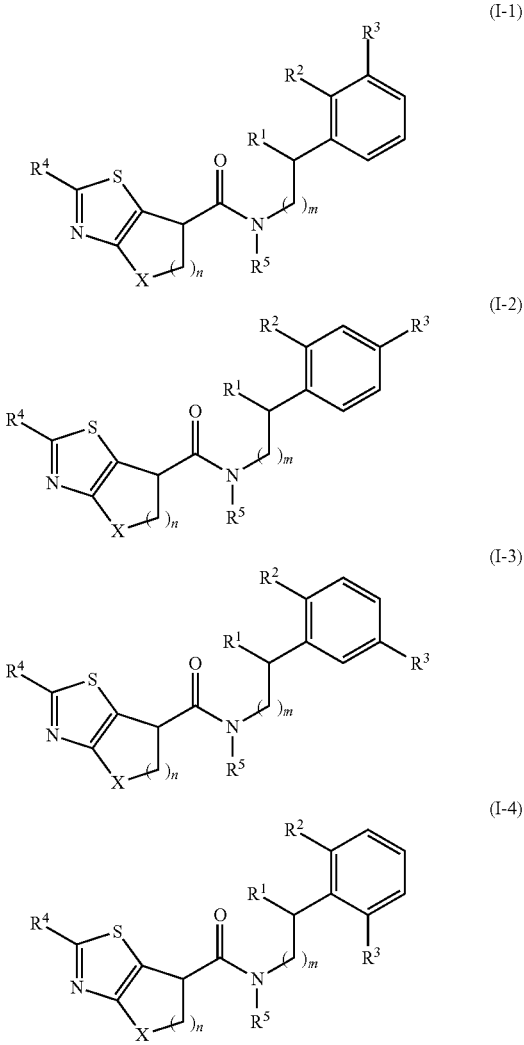

In case p represents 2, the second $R^3$ group may be attached to any carbon atom of the phenyl ring of any one of formulas (I-1), (I-2), (I-3) or (I-4), which carbon atom is not already substituted, wherein the two $R^3$ groups may be the same or different. In case p represents 0, the $R^3$ group is absent.

Definitions provided herein are intended to apply uniformly to the compounds of formulae (I), (I-1), (I-2), (I-3), (I-4), ($I_{Bn}$), ($I_{XO}$) and ($I_{XC}$), as defined in any one of embodiments 1) to 26), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a straight or branched chain alkyl group containing one to four carbon atoms. The term "($C_x$-$C_y$)alkyl" (x and y each being an integer), refers to an alkyl group as defined before containing x to y carbon atoms. For example a ($C_1$-$C_4$)alkyl group contains from one to four carbon atoms. Representative examples of alkyl groups include methyl, ethyl, n-propyl, iso-propyl, n-butyl, iso-butyl, sec.-butyl and tert.-butyl.

In case "$R^1$" represents "($C_1$-$C_2$)alkyl" the term means ($C_1$-$C_2$)alkyl groups as defined above. Examples of said groups are methyl and ethyl. Preferred is methyl.

In case "$R^3$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec.-butyl and tert.-butyl. Preferred is methyl.

In case "$R^4$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec.-butyl and tert.-butyl. Preferred is methyl.

The term "alkoxy", used alone or in combination, refers to an alkyl-O— group wherein the alkyl group is as defined above. The term "($C_x$-$C_y$)alkoxy" (x and y each being an integer) refers to an alkoxy group as defined before containing x to y carbon atoms. For example a ($C_1$-$C_4$)alkoxy group contains from one to four carbon atoms. Representative examples of alkoxy groups include methoxy, ethoxy, n-propoxy, iso-propoxy, n-butoxy, iso-butoxy, sec.-butoxy and tert.-butoxy.

In case "$R^3$" represents "($C_1$-$C_4$)alkoxy" the term means ($C_1$-$C_4$)alkoxy groups as defined above. Examples of said groups are methoxy, ethoxy, n-propoxy, iso-propoxy, n-butoxy, iso-butoxy, sec.-butoxy and tert.-butoxy. Preferred is methoxy.

The term "hydroxy($C_x$-$C_y$)alkyl" (x and y each being an integer), used alone or in combination, refers to an alkyl group as defined before containing x to y carbon atoms in which one hydrogen atom has been replaced with hydroxy. For example a hydroxy-($C_1$-$C_3$)alkyl group contains from one to three carbon atoms in which one hydrogen atom has been replaced with hydroxy. Examples of said groups are hydroxy-methyl, hydroxy-ethyl and hydroxy-propyl.

In case "$R^1$" represents "hydroxy-($C_1$-$C_2$)alkyl" the term means hydroxy-($C_1$-$C_2$)alkyl groups as defined above. Representative examples of said groups are hydroxy-methyl, 1-hydroxy-ethyl and 2-hydroxy-ethyl. Preferred is hydroxy-methyl.

In case "$R^3$" represents "hydroxy-($C_1$-$C_3$)alkyl" the term means hydroxy-($C_1$-$C_3$)alkyl groups as defined above. Representative examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl and 2-hydroxy-prop-2-yl. Preferred is hydroxy-methyl.

The term "($C_1$-$C_2$)alkoxy-($C_1$-$C_2$)alkyl", used alone or in combination, refers to an alkyl group as defined before containing one or two carbon atoms in which one hydrogen atom has been replaced with ($C_1$-$C_2$)alkoxy as defined before.

Examples of said groups are methoxy-methyl, methoxy-ethyl, ethoxy-methyl and ethoxy-ethyl.

In case "$R^3$" represents "$(C_1-C_2)$alkoxy-$(C_1-C_2)$alkyl" the term means "$(C_1-C_2)$alkoxy-$(C_1-C_2)$alkyl groups as defined above. Representative examples of said groups are methoxy-methyl, 1-methoxy-ethyl, 2-methoxy-ethyl, ethoxy-methyl, 1-ethoxy-ethyl and 2-ethoxy-ethyl. Preferred is methoxy-methyl.

The term "hydroxy-$(C_x-C_y)$alkoxy" (x and y each being an integer), used alone or in combination, refers to an alkoxy group as defined before containing x to y carbon atoms in which one hydrogen atom has been replaced with hydroxy. For example a hydroxy-$(C_2-C_3)$alkoxy group contains from two to three carbon atoms in which one hydrogen atom has been replaced with hydroxy. Examples of said groups are 2-hydroxy-ethoxy, 2-hydroxy-prop-1-oxy, 3-hydroxy-prop-1-oxy and 1-hydroxy-prop-2-oxy.

In case "$R^3$" represents "hydroxy-$(C_2-C_3)$alkoxy" the term means hydroxy-$(C_2-C_3)$alkoxy groups as defined above. Representative examples of said groups are 2-hydroxy-ethoxy, 2-hydroxy-prop-1-oxy, 3-hydroxy-prop-1-oxy and 1-hydroxy-prop-2-oxy. Preferred is 2-hydroxy-ethoxy.

The term "hydroxy-$(C_2-C_3)$alkoxy-$(C_1-C_2)$alkyl", used alone or in combination, refers to an alkyl group as defined before containing one or two carbon atoms in which one hydrogen atom has been replaced with hydroxy-$(C_2-C_3)$alkoxy as defined before. Examples of said groups are (2-hydroxy-ethoxy)-methyl, 1-(2-hydroxy-ethoxy)-ethyl, 2-(2-hydroxy-ethoxy)-ethyl, (2-hydroxy-prop-1-oxy)-methyl, (3-hydroxy-prop-1-oxy)-methyl, (1-hydroxy-prop-2-oxy)-methyl, 1-(2-hydroxy-prop-1-oxy)-ethyl, 1-(3-hydroxy-prop-1-oxy)-ethyl, 1-(1-hydroxy-prop-2-oxy)-ethyl, 2-(2-hydroxy-prop-1-oxy)-ethyl, 2-(3-hydroxy-prop-1-oxy)-ethyl, and 2-(1-hydroxy-prop-2-oxy)-ethyl.

In case "$R^3$" represents "hydroxy-$(C_2-C_3)$alkoxy-$(C_1-C_2)$alkyl" the term means hydroxy-$(C_2-C_3)$alkoxy-$(C_1-C_2)$alkyl groups as defined above. Representative examples of said groups are (2-hydroxy-ethoxy)-methyl, 1-(2-hydroxy-ethoxy)-ethyl, 2-(2-hydroxy-ethoxy)-ethyl, (2-hydroxy-prop-1-oxy)-methyl, (3-hydroxy-prop-1-oxy)-methyl, (1-hydroxy-prop-2-oxy)-methyl, 1-(2-hydroxy-prop-1-oxy)-ethyl, 1-(3-hydroxy-prop-1-oxy)-ethyl, 1-(1-hydroxy-prop-2-oxy)-ethyl, 2-(2-hydroxy-prop-1-oxy)-ethyl, 2-(3-hydroxy-prop-1-oxy)-ethyl, and 2-(1-hydroxy-prop-2-oxy)-ethyl. Preferred is (2-hydroxy-ethoxy)-methyl.

The term "$(C_3-C_6)$cycloalkyl", used alone or in combination, refers to a cycloalkyl group with 3 to 6 carbon atoms. Examples of $(C_3-C_6)$cycloalkyl groups are cyclopropyl, cyclobutyl, cyclopentyl and cyclohexyl.

In case "$R^3$" represents "$(C_3-C_6)$cycloalkyl" the term means $(C_3-C_6)$cycloalkyl groups as defined above. Representative examples of said groups are cyclopropyl, cyclobutyl, cyclopentyl and cyclohexyl. Preferred is cyclopropyl.

The term "$(C_x-C_y)$fluoroalkyl" (x and y each being an integer) refers to an alkyl group as defined before containing x to y carbon atoms in which one or more (and possibly all) hydrogen atoms have been replaced with fluoro. For example a $(C_1-C_3)$fluoroalkyl group contains from one to three carbon atoms in which one to seven hydrogen atoms have been replaced with fluoro.

In case "$R^3$" represents "$(C_1-C_3)$fluoroalkyl" the term means $(C_1-C_3)$fluoroalkyl groups as defined above. Representative examples of said groups are difluoromethyl, trifluoromethyl, 2,2-difluoroethyl and 2,2,2-trifluoroethyl. Preferred is trifluoromethyl.

In case "$R^4$" represents "$(C_1-C_3)$fluoroalkyl" the term means $(C_1-C_3)$fluoroalkyl groups as defined above. Representative examples of said groups are difluoromethyl, trifluoromethyl, 2,2-difluoroethyl and 2,2,2-trifluoroethyl. Preferred is trifluoromethyl.

The term "$(C_x-C_y)$fluoroalkoxy" (x and y each being an integer) refers to an alkoxy group as defined before containing x to y carbon atoms in which one or more (and possibly all) hydrogen atoms have been replaced with fluoro. For example a $(C_1-C_3)$fluoroalkoxy group contains from one to three carbon atoms in which one to seven hydrogen atoms have been replaced with fluoro.

In case "$R^3$" represents "$(C_1-C_3)$fluoroalkoxy" the term means $(C_1-C_3)$fluoroalkoxy groups as defined above. Representative examples of said groups are difluoromethoxy, trifluoromethoxy, 2,2-difluoroethoxy and 2,2,2-trifluoroethoxy. Preferred is trifluoromethoxy.

The term halogen means fluoro, chloro or bromo.

In case "$R^2$" represents "halogen" the term means fluoro, chloro or bromo. Preferred is chloro.

In case "$R^3$" represents "halogen" the term means fluoro, chloro or bromo. Preferred are chloro and bromo.

In case "$R^4$" represents "halogen" the term means fluoro, chloro or bromo. Preferred is bromo.

2) A further embodiment of the invention relates to compounds of formula (I) according to embodiment 1) that are also compounds of formula ($I_{Bn}$),

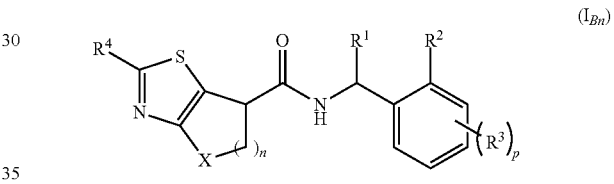

wherein
n represents 1, 2 or 3;
p represents 1 or 2;
X represents —O— or —CH$_2$—;
$R^1$ represents hydrogen, $(C_1-C_2)$alkyl or hydroxy-$(C_1-C_2)$alkyl and $R^2$ represents hydrogen or halogen; or $R^1$ and $R^2$ together represent a —CH$_2$CH$_2$— group;
each $R^3$ independently represents $(C_1-C_4)$alkyl, $(C_3-C_6)$cycloalkyl, $(C_1-C_4)$alkoxy, hydroxy-$(C_1-C_3)$alkyl, hydroxy-$(C_2-C_3)$alkoxy, hydroxy-$(C_2-C_3)$alkoxy-$(C_1-C_2)$alkyl, $(C_1-C_2)$alkoxy-$(C_1-C_2)$alkyl, $(C_1-C_3)$fluoroalkyl, cyano or halogen; and
$R^4$ represents hydrogen, $(C_1-C_4)$alkyl, $(C_1-C_3)$fluoroalkyl, amino or halogen; and to the salts (in particular pharmaceutically acceptable salts) of such compounds.

3) A further embodiment of the invention relates to compounds according to embodiment 2), wherein
n represents 1, 2 or 3;
p represents 1 or 2;
X represents —O— or —CH$_2$—;
$R^1$ represents hydrogen or methyl and $R^2$ represents chloro; or $R^1$ and $R^2$ together represent a —CH$_2$CH$_2$— group;
each $R^3$ independently represents $(C_1-C_4)$alkyl, $(C_3-C_6)$cycloalkyl, $(C_1-C_4)$alkoxy, hydroxy-$(C_1-C_3)$alkyl, hydroxy-$(C_2-C_3)$alkoxy, hydroxy-$(C_2-C_3)$alkoxy-$(C_1-C_2)$alkyl, $(C_1-C_2)$alkoxy-$(C_1-C_2)$alkyl, trifluoromethyl or halogen; and
$R^4$ represents hydrogen, $(C_1-C_4)$alkyl, trifluoromethyl, amino or halogen;
and to the salts (in particular pharmaceutically acceptable salts) of such compounds.

4) A further embodiment of the invention relates to compounds according to embodiment 2), wherein n represents 1, 2 or 3;
p represents 1 or 2;
X represents —O— or —CH$_2$—;
R$^1$ represents hydrogen or methyl and R$^2$ represents chloro; or R$^1$ and R$^2$ together represent a —CH$_2$CH$_2$— group;
each R$^3$ independently represents methyl, cyclopropyl, methoxy, hydroxy-methyl, 2-hydroxy-ethoxy, (2-hydroxy-ethoxy)-methyl, methoxy-methyl, trifluoromethyl, fluoro, chloro or bromo; and
R$^4$ represents hydrogen, methyl, trifluoromethyl, amino or bromo;
and to the salts (in particular pharmaceutically acceptable salts) of such compounds.

5) A further embodiment of the invention relates to compounds of formula (I) according to embodiment 1) that are also compounds of formula (I$_{XO}$), (I$_{XO}$)

wherein
n represents 1, 2 or 3;
m represents 0, 1 or 2;
p represents 1 or 2;
R$^1$ represents hydrogen, (C$_1$-C$_2$)alkyl or hydroxy-(C$_1$-C$_2$)alkyl and R$^2$ represents hydrogen or halogen; or R$^1$ and R$^2$ together represent a —CH$_2$CH$_2$— or a —CH$_2$CH$_2$CH$_2$— group;
each R$^3$ independently represents (C$_1$-C$_4$)alkyl, (C$_3$-C$_6$)cycloalkyl, (C$_1$-C$_4$)alkoxy, hydroxy-(C$_1$-C$_3$)alkyl, hydroxy-(C$_2$-C$_3$)alkoxy, hydroxy-(C$_2$-C$_3$)alkoxy-(C$_1$-C$_2$)alkyl, (C$_1$-C$_2$)alkoxy-(C$_1$-C$_2$)alkyl, (C$_1$-C$_3$)fluoroalkyl, (C$_1$-C$_3$)fluoroalkoxy, cyano, halogen or phenoxy; and
R$^5$ represents hydrogen or methyl;
and to the salts (in particular pharmaceutically acceptable salts) of such compounds.

6) A further embodiment of the invention relates to compounds according to embodiment 5), wherein n represents 1 or 2;
m represents 0;
p represents 1 or 2;
R$^1$ represents hydrogen and R$^2$ represents hydrogen or halogen; or R$^1$ and R$^2$ together represent a —CH$_2$CH$_2$— group;
each R$^3$ independently represents (C$_1$-C$_4$)alkyl, (C$_3$-C$_6$)cycloalkyl, hydroxy-(C$_1$-C$_3$)alkyl, hydroxy-(C$_2$-C$_3$)alkoxy, hydroxy-(C$_2$-C$_3$)alkoxy-(C$_1$-C$_2$)alkyl, trifluoromethyl, cyano or halogen; and
R$^5$ represents hydrogen;
and to the salts (in particular pharmaceutically acceptable salts) of such compounds.

7) A further embodiment of the invention relates to compounds according to embodiment 5), wherein n represents 1 or 2;
m represents 0;
p represents 1 or 2;
R$^1$ represents hydrogen and R$^2$ represents chloro; or R$^1$ and R$^2$ together represent a —CH$_2$CH$_2$— group;
each R$^3$ independently represents methyl, cyclopropyl, hydroxy-methyl, 2-hydroxy-ethoxy, (2-hydroxy-ethoxy)-methyl, trifluoromethyl, fluoro, chloro or bromo; and
R$^5$ represents hydrogen;
and to the salts (in particular pharmaceutically acceptable salts) of such compounds.

8) A further embodiment of the invention relates to compounds of formula (I) according to embodiment 1) that are also compounds of formula (I$_{XC}$), (I$_{XC}$)

wherein
n represents 1, 2 or 3;
m represents 0, 1 or 2;
p represents 1 or 2;
R$^1$ represents hydrogen, (C$_1$-C$_2$)alkyl or hydroxy-(C$_1$-C$_2$)alkyl and R$^2$ represents hydrogen or halogen; or R$^1$ and R$^2$ together represent a —CH$_2$CH$_2$— or a —CH$_2$CH$_2$CH$_2$— group;
each R$^3$ independently represents (C$_1$-C$_4$)alkyl, (C$_3$-C$_6$)cycloalkyl, (C$_1$-C$_4$)alkoxy, hydroxy-(C$_1$-C$_3$)alkyl, (C$_1$-C$_2$)alkoxy-(C$_1$-C$_2$)alkyl, (C$_1$-C$_3$)fluoroalkyl, (C$_1$-C$_3$)fluoroalkoxy, cyano, halogen or phenoxy;
R$^4$ represents hydrogen, (C$_1$-C$_4$)alkyl, (C$_1$-C$_3$)fluoroalkyl, amino, halogen or phenyl; and
R$^5$ represents hydrogen or methyl;
and to the salts (in particular pharmaceutically acceptable salts) of such compounds.

9) A further embodiment of the invention relates to compounds according to embodiment 8), wherein n represents 1, 2 or 3;
m represents 0;
p represents 1 or 2;
R$^1$ represents hydrogen, (C$_1$-C$_2$)alkyl or hydroxy-(C$_1$-C$_2$)alkyl and R$^2$ represents hydrogen or halogen; or R$^1$ and R$^2$ together represent a —CH$_2$CH$_2$— group;
each R$^3$ independently represents (C$_1$-C$_4$)alkyl, (C$_1$-C$_4$)alkoxy, hydroxy-(C$_1$-C$_3$)alkyl, (C$_1$-C$_2$)alkoxy-(C$_1$-C$_2$)alkyl, trifluoromethyl or halogen;
R$^4$ represents hydrogen, (C$_1$-C$_4$)alkyl, trifluoromethyl, amino or halogen; and
R$^5$ represents hydrogen;
and to the salts (in particular pharmaceutically acceptable salts) of such compounds.

10) A further embodiment of the invention relates to compounds according to embodiment 8), wherein n represents 1, 2 or 3;
m represents 0;
p represents 1 or 2;
R$^1$ represents hydrogen or methyl and R$^2$ represents chloro; or R$^1$ and R$^2$ together represent a —CH$_2$CH$_2$— group;

each $R^3$ independently represents methyl, methoxy, hydroxy-methyl, methoxy-methyl, trifluoromethyl, fluoro, chloro or bromo;

$R^4$ represents hydrogen, methyl, trifluoromethyl, amino or bromo; and $R^5$ represents hydrogen;

and to the salts (in particular pharmaceutically acceptable salts) of such compounds.

11) A further embodiment of the invention relates to compounds according to any one of embodiments 1) to 10), wherein n represents 1;

and to the salts (in particular pharmaceutically acceptable salts) of such compounds.

12) A further embodiment of the invention relates to compounds according to any one of embodiments 1) to 10), wherein n represents 2;

and to the salts (in particular pharmaceutically acceptable salts) of such compounds.

13) A further embodiment of the invention relates to compounds according to any one of embodiments 1) to 5) or 8) to 10), wherein n represents 3;

and to the salts (in particular pharmaceutically acceptable salts) of such compounds.

14) A further embodiment of the invention relates to compounds according to any one of embodiments 1), 5), 8) or 11) to 13), wherein m represents 0;

and to the salts (in particular pharmaceutically acceptable salts) of such compounds.

15) A further embodiment of the invention relates to compounds according to any one of embodiments 1) to 14), wherein p represents 2;

and to the salts (in particular pharmaceutically acceptable salts) of such compounds.

16) A further embodiment of the invention relates to compounds according to any one of embodiments 1), 2), 5), 8), 9) or 11) to 15), wherein $R^1$ represents hydrogen, methyl or hydroxy-methyl and $R^2$ represents chloro; and to the salts (in particular pharmaceutically acceptable salts) of such compounds.

17) A further embodiment of the invention relates to compounds according to any one of embodiments 1) to 15), wherein $R^1$ represents hydrogen and $R^2$ represents chloro;

and to the salts (in particular pharmaceutically acceptable salts) of such compounds.

18) A further embodiment of the invention relates to compounds according to any one of embodiments 1) to 15), wherein $R^1$ and $R^2$ together represent a —$CH_2CH_2$— group;

and to the salts (in particular pharmaceutically acceptable salts) of such compounds.

19) A further embodiment of the invention relates to compounds according to any one of embodiments 1) to 5) or 11) to 18), wherein a first $R^3$ group is attached in para-position relative to the $R^1$-bearing carbon atom and represents chloro; and a second $R^3$ group is absent, or is attached in ortho-position relative to the $R^1$-bearing carbon atom and represents methyl, cyclopropyl, methoxy, hydroxy-methyl, 2-hydroxy-ethoxy, (2-hydroxy-ethoxy)-methyl, methoxy-methyl, chloro or bromo;

and to the salts (in particular pharmaceutically acceptable salts) of such compounds.

20) A further embodiment of the invention relates to compounds according to any one of embodiments 1) to 18), wherein a first $R^3$ group is attached in para-position relative to the $R^1$-bearing carbon atom and represents chloro; and a second $R^3$ group is attached in ortho-position relative to the $R^1$-bearing carbon atom and represents methyl, hydroxy-methyl, chloro or bromo;

and to the salts (in particular pharmaceutically acceptable salts) of such compounds.

21) A further embodiment of the invention relates to compounds according to any one of embodiments 1) to 4) or 8) to 20), wherein $R^4$ represents hydrogen;

and to the salts (in particular pharmaceutically acceptable salts) of such compounds.

22) A further embodiment of the invention relates to compounds according to any one of embodiments 1) to 4) or 8) to 20), wherein $R^4$ represents methyl or amino;

and to the salts (in particular pharmaceutically acceptable salts) of such compounds.

23) A further embodiment of the invention relates to compounds according to any one of embodiments 1), 5), 8) or 11) to 22), wherein $R^5$ represents hydrogen;

and to the salts (in particular pharmaceutically acceptable salts) of such compounds.

24) A further embodiment of the invention relates to compounds according to any one of embodiments 1) to 23), wherein the stereogenic center in the heterocyclic ring system is (S)-configured;

and to the salts (in particular pharmaceutically acceptable salts) of such compounds.

25) A further embodiment of the invention relates to compounds according to any one of embodiments 1) to 23), wherein the stereogenic center in the heterocyclic ring system is (R)-configured;

and to the salts (in particular pharmaceutically acceptable salts) of such compounds.

26) Preferred compounds of formula (I) as defined in embodiment 1) are selected from the group consisting of:

N-(4-chlorobenzyl)-5,6-dihydrofuro[2,3-d]thiazole-6-carboxamide;

N-(2,4-dichlorobenzyl)-5,6-dihydrofuro[2,3-d]thiazole-6-carboxamide;

N-(2-chloro-4-fluorobenzyl)-5,6-dihydrofuro[2,3-d]thiazole-6-carboxamide;

N-(3,4-dichlorobenzyl)-5,6-dihydrofuro[2,3-d]thiazole-6-carboxamide;

N-(2-bromo-4,6-dichlorobenzyl)-5,6-dihydrofuro[2,3-d]thiazole-6-carboxamide;

N-(2,4-dichloro-6-methylbenzyl)-5,6-dihydrofuro[2,3-d]thiazole-6-carboxamide;

N-(2,4-dichlorophenethyl)-5,6-dihydrofuro[2,3-d]thiazole-6-carboxamide;

N-(3-(2,4-dichlorophenyl)propyl)-5,6-dihydrofuro[2,3-d]thiazole-6-carboxamide;

N-(1-(2,4-dichlorophenyl)-2-hydroxyethyl)-5,6-dihydrofuro[2,3-d]thiazole-6-carboxamide;

N-(2,4-dichloro-6-(hydroxymethyl)benzyl)-5,6-dihydrofuro[2,3-d]thiazole-6-carboxamide;

N-(5,7-dichloro-2,3-dihydro-1H-inden-1-yl)-5,6-dihydrofuro[2,3-d]thiazole-6-carboxamide;

N-(2,4-dichloro-6-cyclopropylbenzyl)-5,6-dihydrofuro[2,3-d]thiazole-6-carboxamide;
N-(2-chloro-3-(trifluoromethyl)benzyl)-5,6-dihydrofuro[2,3-d]thiazole-6-carboxamide;
N-(3-chloro-2-(trifluoromethyl)benzyl)-5,6-dihydrofuro[2,3-d]thiazole-6-carboxamide;
N-(2,4-dichloro-6-((2-hydroxyethoxy)methyl)benzyl)-5,6-dihydrofuro[2,3-d]thiazole-6-carboxamide;
N-(4-phenoxybenzyl)-5,6-dihydrofuro[2,3-d]thiazole-6-carboxamide;
N-(2,4-dichlorobenzyl)-5,6-dihydro-4H-cyclopenta[d]thiazole-6-carboxamide;
N-(2-chloro-4-fluorobenzyl)-5,6-dihydro-4H-cyclopenta[d]thiazole-6-carboxamide;
N-(2-bromo-4,6-dichlorobenzyl)-5,6-dihydro-4H-cyclopenta[d]thiazole-6-carboxamide;
N-(2,4-dichloro-6-methylbenzyl)-5,6-dihydro-4H-cyclopenta[d]thiazole-6-carboxamide;
N-(2,4-dichlorophenethyl)-5,6-dihydro-4H-cyclopenta[d]thiazole-6-carboxamide;
N-(2-chloro-3-cyanobenzyl)-5,6-dihydro-4H-cyclopenta[d]thiazole-6-carboxamide;
N-(3-(2,4-dichlorophenyl)propyl)-5,6-dihydro-4H-cyclopenta[d]thiazole-6-carboxamide;
N-(1-(2,4-dichlorophenyl)-2-hydroxyethyl)-5,6-dihydro-4H-cyclopenta[d]thiazole-6-carboxamide;
N-(2,4-dichloro-6-(hydroxymethyl)benzyl)-5,6-dihydro-4H-cyclopenta[d]thiazole-6-carboxamide;
N-(2,4-dichloro-6-methoxybenzyl)-5,6-dihydro-4H-cyclopenta[d]thiazole-6-carboxamide;
N-(5,7-dichloro-2,3-dihydro-1H-inden-1-yl)-5,6-dihydro-4H-cyclopenta[d]thiazole-6-carboxamide;
N-(2-chloro-3-(trifluoromethyl)benzyl)-5,6-dihydro-4H-cyclopenta[d]thiazole-6-carboxamide;
N-(3-fluoro-4-(trifluoromethoxy)benzyl)-5,6-dihydro-4H-cyclopenta[d]thiazole-6-carboxamide;
N-(4-chlorobenzyl)-N-methyl-6,7-dihydro-5H-pyrano[2,3-d]thiazole-7-carboxamide;
N-(2,4-dichlorobenzyl)-6,7-dihydro-5H-pyrano[2,3-d]thiazole-7-carboxamide;
N-(2-chloro-4-fluorobenzyl)-6,7-dihydro-5H-pyrano[2,3-d]thiazole-7-carboxamide;
N-(2,3-dichlorobenzyl)-6,7-dihydro-5H-pyrano[2,3-d]thiazole-7-carboxamide;
N-(2,4-dichloro-6-methylbenzyl)-6,7-dihydro-5H-pyrano[2,3-d]thiazole-7-carboxamide;
N-(2,4-dichlorophenethyl)-6,7-dihydro-5H-pyrano[2,3-d]thiazole-7-carboxamide;
N-(2-chloro-3-cyanobenzyl)-6,7-dihydro-5H-pyrano[2,3-d]thiazole-7-carboxamide;
N-(4-(trifluoromethyl)benzyl)-6,7-dihydro-5H-pyrano[2,3-d]thiazole-7-carboxamide;
N-(3-(2,4-dichlorophenyl)propyl)-6,7-dihydro-5H-pyrano[2,3-d]thiazole-7-carboxamide;
N—((S)-1-(2,4-dichlorophenyl)-2-hydroxyethyl)-6,7-dihydro-5H-pyrano[2,3-d]thiazole-7-carboxamide;
N-(2,4-dichloro-6-(hydroxymethyl)benzyl)-6,7-dihydro-5H-pyrano[2,3-d]thiazole-7-carboxamide;
N—((S)-5,7-dichloro-2,3-dihydro-1H-inden-1-yl)-6,7-dihydro-5H-pyrano[2,3-d]thiazole-7-carboxamide;
N-(2-chloro-3-(trifluoromethyl)benzyl)-6,7-dihydro-5H-pyrano[2,3-d]thiazole-7-carboxamide;
N-(2,4-dichloro-6-(2-hydroxyethoxy)benzyl)-6,7-dihydro-5H-pyrano[2,3-d]thiazole-7-carboxamide;
N-(3-fluoro-4-(trifluoromethoxy)benzyl)-6,7-dihydro-5H-pyrano[2,3-d]thiazole-7-carboxamide;
N-(4-phenoxybenzyl)-6,7-dihydro-5H-pyrano[2,3-d]thiazole-7-carboxamide;
N-(4-chlorobenzyl)-4,5,6,7-tetrahydrobenzo[d]thiazole-7-carboxamide;
N-(4-chlorobenzyl)-N-methyl-4,5,6,7-tetrahydrobenzo[d]thiazole-7-carboxamide;
N-(3-chloro-2-methyl benzyl)-4,5,6,7-tetrahydrobenzo[d]thiazole-7-carboxamide;
2-amino-N-(2,4-dichlorobenzyl)-4,5,6,7-tetrahydrobenzo[d]thiazole-7-carboxamide;
N-(2,4-dichlorobenzyl)-2-methyl-4,5,6,7-tetrahydrobenzo[d]thiazole-7-carboxamide;
2-bromo-N-(2,4-dichlorobenzyl)-4,5,6,7-tetrahydrobenzo[d]thiazole-7-carboxamide;
N-(2,4-dichlorobenzyl)-4,5,6,7-tetrahydrobenzo[d]thiazole-7-carboxamide;
N-(2-chloro-4-fluorobenzyl)-4,5,6,7-tetrahydrobenzo[d]thiazole-7-carboxamide;
N-(2,3-dichlorobenzyl)-4,5,6,7-tetrahydrobenzo[d]thiazole-7-carboxamide;
N-(2,3-dihydro-1H-inden-1-yl)-4,5,6,7-tetrahydrobenzo[d]thiazole-7-carboxamide;
N—((R)-1-(2,4-dichlorophenyl)ethyl)-4,5,6,7-tetrahydrobenzo[d]thiazole-7-carboxamide;
N-(2,4-dichloro-6-methylbenzyl)-2-phenyl-4,5,6,7-tetrahydrobenzo[d]thiazole-7-carboxamide;
N-(2,4-dichloro-6-methylbenzyl)-2-(trifluoromethyl)-4,5,6,7-tetrahydrobenzo[d]thiazole-7-carboxamide;
2-amino-N-(2,4-dichloro-6-methylbenzyl)-4,5,6,7-tetrahydrobenzo[d]thiazole-7-carboxamide;
N-(2,4-dichloro-6-methylbenzyl)-2-methyl-4,5,6,7-tetrahydrobenzo[d]thiazole-7-carboxamide;
2-bromo-N-(2,4-dichloro-6-methylbenzyl)-4,5,6,7-tetrahydrobenzo[d]thiazole-7-carboxamide;
N-(2,4-dichloro-6-methylbenzyl)-4,5,6,7-tetrahydrobenzo[d]thiazole-7-carboxamide;
N-(2,4-dichlorophenethyl)-4,5,6,7-tetrahydrobenzo[d]thiazole-7-carboxamide;
N—((S)-1-(2,4-dichlorophenyl)-2-hydroxyethyl)-4,5,6,7-tetrahydrobenzo[d]thiazole-7-carboxamide;
N-(2,4-dichloro-6-(hydroxymethyl)benzyl)-4,5,6,7-tetrahydrobenzo[d]thiazole-7-carboxamide;
2-bromo-N-(2-chloro-3-(trifluoromethyl)benzyl)-4,5,6,7-tetrahydrobenzo[d]thiazole-7-carboxamide;
N-(2-chloro-3-(trifluoromethyl)benzyl)-4,5,6,7-tetrahydrobenzo[d]thiazole-7-carboxamide;
N-(2,4-dichloro-6-(methoxymethyl)benzyl)-4,5,6,7-tetrahydrobenzo[d]thiazole-7-carboxamide;
N-(3-fluoro-4-(trifluoromethoxy)benzyl)-4,5,6,7-tetrahydrobenzo[d]thiazole-7-carboxamide;
N-(4-phenoxybenzyl)-4,5,6,7-tetrahydrobenzo[d]thiazole-7-carboxamide;
2-amino-N-(2,4-dichlorobenzyl)-5,6,7,8-tetrahydro-4H-cyclohepta[d]thiazole-8-carboxamide;
N-(2,4-dichlorobenzyl)-5,6,7,8-tetrahydro-4H-cyclohepta[d]thiazole-8-carboxamide;
2-amino-N-(2,4-dichloro-6-methylbenzyl)-5,6,7,8-tetrahydro-4H-cyclohepta[d]thiazole-8-carboxamide;
N-(2,4-dichloro-6-methylbenzyl)-5,6,7,8-tetrahydro-4H-cyclohepta[d]thiazole-8-carboxamide;
(R)—N—((S)-1-(2,4-dichlorophenyl)-2-hydroxyethyl)-5,6,7,8-tetrahydro-4H-cyclohepta[d]thiazole-8-carboxamide; and
(S)—N—((S)-1-(2,4-dichlorophenyl)-2-hydroxyethyl)-5,6,7,8-tetrahydro-4H-cyclohepta[d]thiazole-8-carboxamide;
or salts (in particular pharmaceutically acceptable salts) of such compounds;

it is to be understood for any of the above listed compounds, that a stereogenic center, which is not specifically assigned, may be in absolute (R)- or absolute (S)-configuration; for example a compound listed as N-(2-bromo-4,6-dichlorobenzyl)-5,6-dihydrofuro[2,3-d]thiazole-6-carboxamide may be (R)—N-(2-bromo-4,6-dichlorobenzyl)-5,6-dihydrofuro[2,3-d]thiazole-6-carboxamide, (S)—N-(2-bromo-4,6-dichlorobenzyl)-5,6-dihydrofuro[2,3-d]thiazole-6-carboxamide or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 26) as disclosed hereinabove and which are therefore intended and herewith specifically disclosed in individualized form are:

1, 2+1, 3+2+1, 4+2+1, 5+1, 6+5+1, 7+5+1, 8+1, 9+8+1, 10+8+1, 11+3+2+1, 11+6+5+1, 11+9+8+1, 12+3+2+1, 12+6+5+1, 12+9+8+1, 13+3+2+1, 13+9+8+1, 14+1, 15+1, 15+2+1, 15+3+2+1, 15+4+2+1, 15+5+1, 15+6+5+1, 15+7+5+1, 15+8+1, 15+9+8+1, 15+10+8+1, 16+1, 16+2+1, 16+5+1, 16+9+8+1, 17+1, 17+3+2+1, 17+6+5+1, 17+9+8+1, 17+15+1, 17+15+2+1, 17+15+3+2+1, 17+15+4+2+1, 17+15+5+1, 17+15+6+5+1, 17+15+7+5+1, 17+15+8+1, 17+15+9+8+1, 17+15+10+8+1, 18+1, 18+3+2+1, 18+6+5+1, 18+9+8+1, 18+15+1, 18+15+2+1, 18+15+3+2+1, 18+15+4+2+1, 18+15+5+1, 18+15+6+5+1, 18+15+7+5+1, 18+15+8+1, 18+15+9+8+1, 18+15+10+8+1, 19+1, 19+3+2+1, 19+5+1, 19+14+1, 19+15+1, 19+15+2+1, 19+15+3+2+1, 19+15+4+2+1, 19+15+5+1, 19+15+6+5+1, 19+15+7+5+1, 19+15+8+1, 19+15+9+8+1, 19+15+10+8+1, 19+16+1, 19+16+2+1, 19+16+5+1, 19+16+9+8+1, 20+1, 20+2+1, 20+3+2+1, 20+4+2+1, 20+5+1, 20+6+5+1, 20+7+5+1, 20+8+1, 20+9+8+1, 20+10+8+1, 21+1, 21+2+1, 21+3+2+1, 21+4+2+1, 21+8+1, 21+9+8+1, 21+10+8+1, 21+20+1, 21+20+2+1, 21+20+3+2+1, 21+20+4+2+1, 21+20+5+1, 21+20+6+5+1, 21+20+7+5+1, 21+20+8+1, 21+20+9+8+1, 21+20+10+8+1, 22+1, 22+2+1, 22+3+2+1, 22+4+2+1, 22+8+1, 22+9+8+1, 22+10+8+1, 22+20+1, 22+20+2+1, 22+20+3+2+1, 22+20+4+2+1, 22+20+5+1, 22+20+6+5+1, 22+20+7+5+1, 22+20+8+1, 22+20+9+8+1, 22+20+10+8+1, 23+1, 23+5+1, 23+8+1, 24+1, 24+2+1, 24+3+2+1, 24+4+2+1, 24+5+1, 24+6+5+1, 24+7+5+1, 24+8+1, 24+9+8+1, 24+10+8+1, 24+17+1, 24+17+3+2+1, 24+17+6+5+1, 24+17+9+8+1, 24+17+15+1, 24+17+15+2+1, 24+17+15+3+2+1, 24+17+15+4+2+1, 24+17+15+5+1, 24+17+15+6+5+1, 24+17+15+7+5+1, 24+17+15+8+1, 24+17+15+9+8+1, 24+17+15+10+8+1, 25+1, 25+2+1, 25+3+2+1, 25+4+2+1, 25+5+1, 25+6+5+1, 25+7+5+1, 25+8+1, 25+9+8+1, 25+10+8+1, 25+17+1, 25+17+3+2+1, 25+17+6+5+1, 25+17+9+8+1, 25+17+15+1, 25+17+15+2+1, 25+17+15+3+2+1, 25+17+15+4+2+1, 25+17+15+5+1, 25+17+15+6+5+1, 25+17+15+7+5+1, 25+17+15+8+1, 25+17+15+9+8+1, 25+17+15+10+8+1, and 26+1;

wherein the list above is not to be construed as limiting with respect to further embodiments which are also possible based on the dependencies of the embodiments 1) to 26) as disclosed hereinabove and which are also intended. In the list above the numbers refer to the embodiments according to their numbering provided hereinabove whereas "+" indicates the dependency from another embodiment. The different individualized embodiments are separated by commas. In other words, "3+2+1" for example refers to embodiment 3) depending on embodiment 2) depending on embodiment 1), i.e. embodiment "3+2+1" corresponds to embodiment 1) further limited by the features of embodiments 2) and 3).

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 26), or pharmaceutically acceptable salts thereof, are suitable for use as medicaments. In particular, compounds of formula (I) modulate the P2X$_7$ receptor, i.e. they act as P2X$_7$ receptor antagonists, and are useful for the prevention or treatment of diseases which are associated with the activation of the P2X$_7$ receptor such as pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; other auto-immune and allergic disorders; and other disorders with an inflammatory or immunological component.

In particular, the compounds of formula (I) according to any one of embodiments 1) to 26), or pharmaceutically acceptable salts thereof, are suitable for the prevention or treatment of pain. Pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain.

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Chronic articular pain conditions include especially rheumatoid arthritis, osteoarthritis, rheumatoid spondylitis, gouty arthritis and juvenile arthritis.

Pain associated with functional bowel disorders includes especially non-ulcer dyspepsia, non-cardiac chest pain and irritable bowel syndrome.

Further, the compounds of formula (I) according to any one of embodiments 1) to 26), or pharmaceutically acceptable salts thereof, are suitable for the prevention or treatment of neurodegenerative and neuroinflammatory diseases. Neurodegenerative and neuro-inflammatory diseases include Alzheimer's disease and other dementing disorders including, but not limited to, Creutzfeldt-Jakob disease (CJD) and new variant Creutzfeldt-Jakob disease (nvCJD); Amyotrophic lateral sclerosis, amyloidosis; multiple sclerosis and other demyelinating syndromes; cerebral atherosclerosis and vasculitis; temporal arteritis; myasthenia gravis; Huntington's disease; Lewy Body dementia; and Parkinson's disease.

Further, the compounds of formula (I) according to any one of embodiments 1) to 26), or pharmaceutically acceptable salts thereof, are suitable for the prevention or treatment of bone and joint diseases. Bone and joint diseases include arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; arthritides associated with or including osteoarthritis/osteoarthrosis, both primary and secondary to, for example, congenital hip dysplasia; cervical and lumbar spondylitis; Still's disease; seronegative spondyloarthropathies including ankylosing spondylitis, psoriatic arthritis, reactive arthritis and undifferentiated spondyloarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Familial Mediterranean fever, Muckle-Wells syndrome, and Familial Hibernian Fever, Kikuchi disease; and drug-induced arthalgias, tendonitis, and myopathies including dystrophies and other inflammatory myopathies.

Further, the compounds of formula (I) according to any one of embodiments 1) to 26), or pharmaceutically acceptable salts thereof, are suitable for the prevention or treatment of obstructive diseases of the airways. Obstructive diseases of the airways include asthma, including bronchial, allergic, intrinsic, and extrinsic asthma, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; and acute viral infection including the common cold, and infection due to respiratory syncytial virus, influenza, coronavirus (including SARS) and adenovirus.

Further, the compounds of formula (I) according to any one of embodiments 1) to 26), or pharmaceutically acceptable salts thereof, are suitable for the prevention or treatment of cardiovascular diseases. Cardiovascular diseases include atherosclerosis, affecting the coronary and peripheral circulation; pericarditis; myocarditis; inflammatory and auto-immune cardiomyopathies including myocardial sarcoid; ischaemic reperfusion injuries; endocarditis, valvulitis, and aortitis including infective (for example syphilitic); vasculitides; and disorders of the proximal and peripheral veins including phlebitis and thrombosis, including deep vein thrombosis and complications of varicose veins.

Further, the compounds of formula (I) according to any one of embodiments 1) to 26), or pharmaceutically acceptable salts thereof, are suitable for the prevention or treatment of eye diseases. Eye diseases include blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; and infections of the eyes including viral, fungal, and bacterial infections.

Further, the compounds of formula (I) according to any one of embodiments 1) to 26), or pharmaceutically acceptable salts thereof, are suitable for the prevention or treatment of skin diseases. Skin diseases include psoriasis, skin burn, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber—Christian syndrome, erythema multiforme; cellulitis, both infective and non-infective; panniculitis; cutaneous lymphomas, non-melanoma skin cancer and other dysplastic lesions; and drug-induced disorders including fixed drug eruptions.

Further, the compounds of formula (I) according to any one of embodiments 1) to 26), or pharmaceutically acceptable salts thereof, are suitable for the prevention or treatment of abdominal and gastrointestinal tract diseases. Abdominal and gastrointestinal tract diseases include hepatitis, including autoimmune, alcoholic and viral hepatitis; fibrosis and cirrhosis of the liver; cholecystitis; pancreatitis, both acute and chronic; non-inflammatory diarrhea; glossitis, gingivitis, periodontitis; oesophagitis, including reflux; eosinophilic gastro-enteritis, mastocytosis, Crohn's disease, colitis including ulcerative colitis, proctitis, pruritis ani; Coeliac disease, irritable bowel disease/syndrome, and food-related allergies which may have effects remote from the gut, for example migraine, rhinitis or eczema; allograft rejection including acute and chronic allograft rejection following, for example, transplantation of kidney, heart, liver, lung, bone marrow, skin or cornea or following blood transfusion; and chronic graft versus host disease;

Further, the compounds of formula (I) according to any one of embodiments 1) to 26), or pharmaceutically acceptable salts thereof, are suitable for the prevention or treatment of genitourinary diseases. Genitourinary diseases include nephritis including interstitial and glomerulonephritis; nephrotic syndrome; cystitis including acute and chronic (interstitial) cystitis and Hunner's ulcer; acute and chronic urethritis, hemorrhagic cystitis, prostatitis, epididymitis, oophoritis and salpingitis; vulvovaginitis; Peyronie's disease; and erectile dysfunction, both male and female.

Further, the compounds of formula (I) according to any one of embodiments 1) to 26), or pharmaceutically acceptable salts thereof, are suitable for the prevention or treatment of cancer. The treatment of cancer includes the treatment of brain tumors, prostate, lung, breast, ovarian, bowel and colon, stomach, pancreatic, skin and bone marrow (including leukaemias) and lymphoproliferative systems, such as non-Hodgkin's and Hodgkin's lymphoma; including the prevention and treatment of metastatic disease and tumor recurrences, and paraneoplastic syndromes.

Further, the compounds of formula (I) according to any one of embodiments 1) to 26), or pharmaceutically acceptable salts thereof, are suitable for the prevention or treatment of other auto-immune and allergic disorders. Other auto-immune and allergic disorders include Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Further, the compounds of formula (I) according to any one of embodiments 1) to 26), or pharmaceutically acceptable salts thereof, are suitable for the prevention or treatment of other disorders with an inflammatory or immunological component. Other disorders with an inflammatory or immunological component include acquired immune deficiency syndrome (AIDS), leprosy, Sezary syndrome, and paraneoplastic syndromes.

Further, the compounds of formula (I) according to any one of embodiments 1) to 26), or pharmaceutically acceptable salts thereof, are suitable for the prevention or treatment of mood, depression, sleep and anxiety disorders.

Further, the compounds of formula (I) according to any one of embodiments 1) to 26), or pharmaceutically acceptable salts thereof, are suitable for the prevention or treatment of injury induced trauma and spinal cord injury.

Especially, compounds of formula (I) according to any one of embodiments 1) to 26), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Neurodegenerative and neuro-inflammatory diseases such as Alzheimer's disease and other dementing disorders including, but not limited to, Creutzfeldt-Jakob disease (CJD) and new variant Creutzfeldt-Jakob disease (nvCJD); amyloidosis; Amyotrophic lateral sclerosis, multiple sclerosis and other demyelinating syndromes; cerebral atherosclerosis and vasculitis; temporal arteritis; myasthenia gravis; Huntington's disease; Lewy Body dementia; and Parkinson's disease;

3) Bone and joint diseases such as arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Muckle-Wells syndrome, and Familial Hibernian Fever, Kikuchi disease; and drug-induced arthalgias, tendonitis, and myopathies;

4) Obstructive diseases of the airways such as chronic obstructive pulmonary disease (COPD); cystic fibrosis; lung emphysema; sarcoidosis; farmer's lung and related diseases; lung fibrosis, including fibrosis complicating tuberculosis; and chronic cough associated with inflammatory and secretory conditions of the airways;

5) Cardiovascular diseases such as inflammatory and autoimmune cardio-myopathies;

6) Eye diseases such as degenerative or inflammatory disorders affecting the retina;

7) Skin diseases such as psoriasis, skin burn, atopic dermatitis, contact dermatitis or other eczematous dermatoses; and discoid lupus erythematosus;

8) Abdominal and gastrointestinal tract diseases such as fibrosis and cirrhosis of the liver; cholecystitis; pancreatitis, both acute and chronic; Crohn's disease; colitis including ulcerative colitis; and irritable bowel disease/syndrome;

9) Genitourinary diseases such as nephritis including interstitial and glomerulonephritis; nephrotic syndrome; and cystitis including acute and chronic (interstitial) cystitis; and 10) Other auto-immune and allergic disorders such as Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Most preferably, compounds of formula (I) according to any one of embodiments 1) to 26), or pharmaceutically acceptable salts thereof, are suitable for the prevention or treatment of diseases selected from one, several or all of the following groups of diseases and disorders:

1) Pain, wherein pain refers to acute pain; chronic pain; pain associated with sprains and strains; chronic articular pain; pain associated with rheumatic fever; musculoskeletal pain (preferred); lower back and neck pain; inflammatory pain; neuropathic pain (preferred); visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis; Pain associated with functional bowel disorders includes especially non-ulcer dyspepsia, non-cardiac chest pain and irritable bowel syndrome;

2) Rheumatoid arthritis and osteoarthritis;
3) Chronic obstructive pulmonary disease (COPD); and
4) Crohn's disease.

The invention also relates to the use of a compound of formula (I) according to any one of embodiments 1) to 26) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 26).

A pharmaceutical composition according to the present invention contains at least one compound of formula (I) according to any one of embodiments 1) to 26) (or a pharmaceutically acceptable salt thereof) as the active agent and optionally carriers and/or diluents and/or adjuvants.

The compounds of formula (I) according to any one of embodiments 1) to 26) and their pharmaceutically acceptable salts can be used as medicaments, e.g. in the form of pharmaceutical compositions for enteral (such as especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 26), or a pharmaceutically acceptable salt thereof.

Any reference to a compound of formula (I), (I-1), (I-2), (I-3), (I-4), ($I_{Bn}$), ($I_{XO}$) and ($I_{XC}$) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula (I-1), of formula (I-2), of formula (I-3), of formula (I-4), of formula ($I_{Bn}$), of formula ($I_{XO}$) and of formula ($I_{XC}$) as well as to the salts and pharmaceutically acceptable salts of the compounds of formula (I), of formula (I-1), of formula (I-2), of formula (I-3), of formula (I-4), of formula ($I_{Bn}$), of formula ($I_{XO}$) and of formula ($I_{XC}$). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (RT) as used herein refers to a temperature of about 25° C. Whenever the word "between" is used to describe a numerical range, it is to be understood that the end points of the indicated range are explicitly included in the range.

For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, $R^5$, n, m, p and X are as defined for formula (I). Other abbreviations used are defined in the experimental section.

In some instances the generic groups $R^1$, $R^2$, $R^3$, $R^4$, $R^5$, n, m, p and X might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

Preparation of Compounds of Formula (I)

Compounds of formula (I) can be prepared by reaction of a carboxylic acid (II) with an amine (III) using standard amide coupling reagents such as EDC.HCl/HOBt, SiliaBond® carbodiimide/HOAt, HATU/HOAt or PyBOP and a base like DIPEA in a solvent like DCM, THF or DMF preferably at temperatures between RT and 45° C. (scheme 1).

Scheme 1: Synthesis of compounds of formula (I)

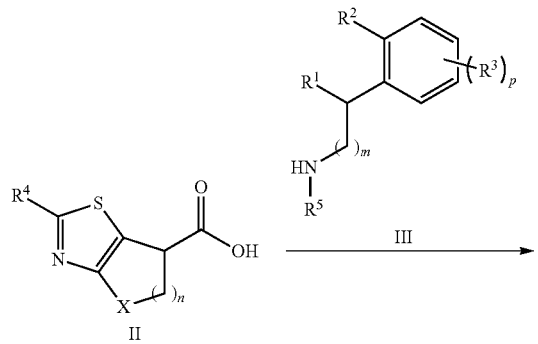

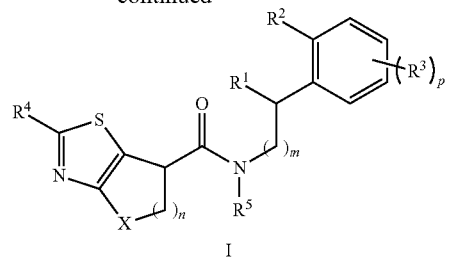

Compounds of formula (I), wherein $R^4$ represents $CF_3$, can be prepared via a Pd(0) mediated procedure from compounds of formula (I), wherein $R^4$ represents bromo, using $Pd_2(dba)_3$, CuI, $Ph_3As$ and methyl 2,2-difluoro-2-(fluorosulfonyl)acetate in a degassed solvent, such as DMF at temperatures between 80° C. and 120° C.

Compounds of formula (II), if not commercially available, can be prepared following the procedures outlined in the schemes below and in the experimental part.

Compounds of formula (II), wherein X represents —$CH_2$— and $R^4$ represents hydrogen, ($C_1$-$C_4$)alkyl, phenyl, or amino can be prepared from a methyl ester (IV) like, for instance, methyl cyclohex-2-enecarboxylate (Bioorg. Med. Chem. 1999, 7, 1505-1511) by a bromohydrin-formation/oxidation sequence using (1) NBS in a THF/$H_2O$ mixture at temperatures around RT and (2) an oxidant such as DMP in a solvent like DCM at temperatures around RT to form α-bromoketone (V) (scheme 2). Condensation with thiourea or a thioamide derivative (VI) ($R^4$ represents hydrogen, ($C_1$-$C_4$) alkyl, phenyl or $NH_2$), in a solvent such as dioxane or EtOH at temperatures between 60° C. and 110° C. provide thiazoles (VII). If not commercially available, thioamides (VI) can be prepared from the corresponding amides with $P_4S_{10}$ or Lawesson's reagent in a solvent such as dioxane or toluene at temperatures between 60° C. and 110° C. Saponification of the methyl ester (VII) can be performed under standard conditions such as LiOH in a THF/MeOH/$H_2O$ mixture, preferably at temperatures between 0° C. and 45° C. to form compounds of formula (IIa).

Scheme 2: Synthesis of compounds of formula (IIa)
($R^4$ represents hydrogen, ($C_1$—$C_4$)alkyl, phenyl, amino or halogen)

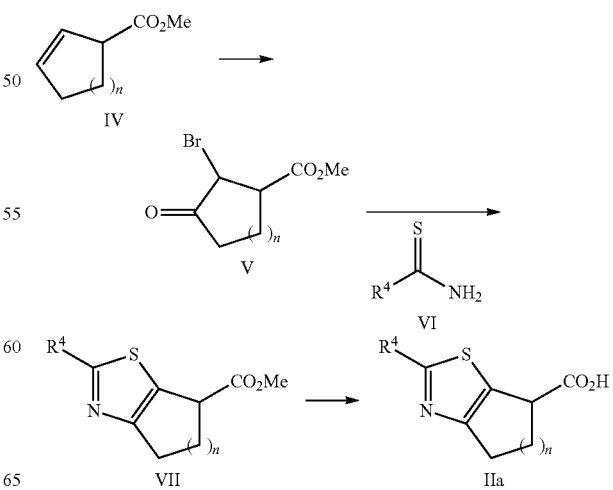

Compounds of formula (II), wherein $R^4$ represents chloro or bromo, respectively, can be prepared via a Sandmeyer type reaction of compounds of formula (VII), wherein $R^4$ represents amino using $Cu(II)Cl_2$ or $Cu(II)Br_2$, respectively, and tBu-nitrite in MeCN at temperatures between RT and 60° C., followed by saponification with a base, such as LiOH in a solvent mixture like THF/MeOH/$H_2O$ at temperatures around RT (scheme 2).

Compounds of formula (II), wherein $R^4$ represents fluoro can be prepared by treating compounds of formula (VII), wherein $R^4$ represents amino with $HBF_4$ and $NOBF_4$ in a solvent like $Et_2O$ at temperatures between −50° C. and RT, followed by saponification with a base, such as LiOH in a solvent mixture like THF/MeOH/$H_2O$ at temperatures around RT (scheme 2).

Alternatively, compounds of formula (II), wherein X represents —$CH_2$— and $R^4$ represents hydrogen or amino, can be prepared from the corresponding cycloalk-2-enone (VIII) by (1) addition of TMS—CN, catalyzed by $Ni(cod)_2$ and $Gd(OTf)_3$ in the presence of norbornadiene in a solvent such as THF at temperatures around RT and (2) bromination of the resulting silylenolether using an electrophilic bromine source such as NBS in a THF/$H_2O$ mixture at temperatures around 0° C. to form α-bromoketone (IX) (scheme 3). The aminothiazoles (X) are prepared by condensation of the corresponding α-bromoketone (IX) with thiourea in a solvent such as dioxane at temperatures between 60° C. and 100° C. Hydrolysis using aq. conc. HCl at temperatures between 60° C. and 100° C. form carboxylic acids (IIb), wherein $R^4$ represents amino. Optionally, aminothiazoles of formula (X) can be diazotized utilizing tBu-nitrite in THF at temperatures between 60° C. and 80° C. to provide the corresponding thiazoles. Hydrolysis of the nitrile group using aq. conc. HCl at temperatures between 60° C. and 100° C. form carboxylic acids (IIb), wherein $R^4$ represents hydrogen.

Scheme 3: Synthesis of compounds of formula (IIb)
($R^4$ represents hydrogen or amino)

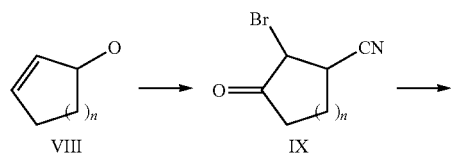

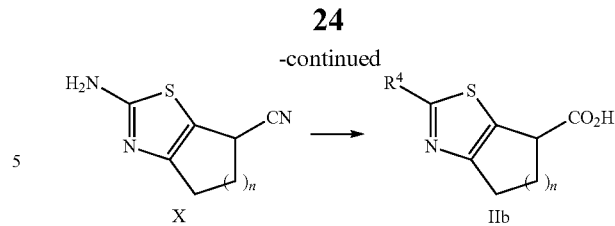

Compounds of formula (II), wherein X represents —O—, n represents 2 or 3, and $R_4$ represents hydrogen, can be prepared by (1) addition of 3-(tert-butyldimethylsilyloxy)propanal or 4-(tert-butyldimethylsilyloxy)butanal, respectively to 5-lithiated 2,4-dichlorothiazole (obtained from 2,4-dichlorothiazole and a strong non-nucleophilic base like LDA in a solvent like THF at temperatures between −20° C. and RT) in a solvent such as THF at −78° C. and (2) protection of the resulting hydroxy group using DHP and a catalyst like PPTS in a solvent such as DCM at temperatures between RT and reflux to form intermediate (XII) (scheme 4). Cyclization precursor (XIII) can be prepared by (1) dechlorination using an alkyllithium species such as nBuLi in a solvent like THF at temperatures between −100° C. and −40° C. and (2) treatment with a fluoride source such as TBAF in a solvent like THF at temperatures between 0° C. and RT. Cyclization to compounds of formula (XIV) can be performed with a base such as NaH or KOtBu in a solvent like DMF or tBuOH, respectively, or through a palladium mediated procedure using $Pd(OAc)_2$, rac-2-(di-tert-butylphosphino)-1,1'-binaphthyl and a base like $Cs_2CO_3$ in a solvent such as toluene at temperatures between 80° C. and 110° C. Compounds of formula (IIc) are obtained by (1) removal of the THP protecting group under acidic conditions using, for instance, catalytic amounts of PTSA in a solvent mixture like THF/$H_2O$ at temperatures around RT, (2) a Mitsunobu reaction, and (3) hydrolysis of the nitrile using aq. conc. HCl at temperatures between 60° C. and 100° C. The Mitsunobu reaction can be carried out with acetone cyanohydrin, $(nBu)_3P$ and 1,1'-(azodicarbonyl)dipiperidine in a solvent like THF at temperatures between 0° C. and RT.

Scheme 4: Synthesis of compounds of formula (IIc) wherein n represents 2 or 3

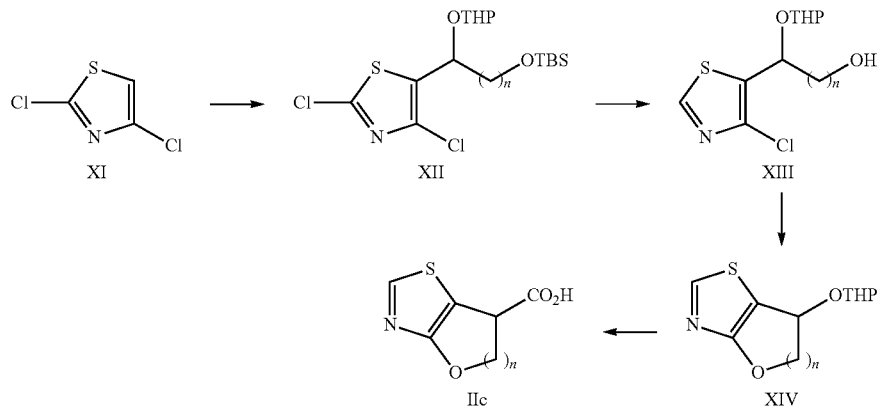

Compound of formula (II), wherein X represents —O—, n represents 1, and R⁴ represents hydrogen, can be prepared by reaction of 4-bromothiazole (XV) with the sodium salt of DL-1,2-isoproylideneglycerol at temperatures between 120° C. and 150° C. and subsequent bromination with an electrophilic bromine source such as NBS in a solvent like MeCN at temperatures between 0° C. and RT (scheme 5). The resulting 5-bromothiazole (XVI) is sequentially treated with (1) catalytic amounts of an acid such as PPTS in a solvent like MeOH at temperatures around reflux, (2) trimethyl orthoformate in a solvent like DCM at temperatures around RT, (3) AcBr in a solvent like DCM at temperatures around RT, and (4) a carbonate base such as $K_2CO_3$ in a solvent like MeOH at temperatures around RT to form oxirane (XVII). At temperatures between −78° C. and RT, a soln. of oxirane (XVII) in an ether solvent like THF is consecutively treated with an alkyl lithium reagent like nBuLi, a trialkylsilyl chloride like TIPSCl, and again with an alkyl lithium reagent like nBuLi to form dihydrofurothiazole (XVIII). A two-step oxidation procedure utilizing (1) Dess Martin's reagent in a solvent like DCM at temperatures between 0° C. and RT and (2) sodium chlorite in a buffered aq. solution with tBuOH as co-solvent and 2-methyl-2-butene as scavenger at temperatures around 0° C. provides carboxylic acid (XIX). Removal of the silyl protecting group to form a compound of formula (IId) can be performed with a fluoride source such as TBAF in a solvent like THF at temperatures between 0° C. and RT.

Scheme 5: Synthesis of compound of formula (IId)

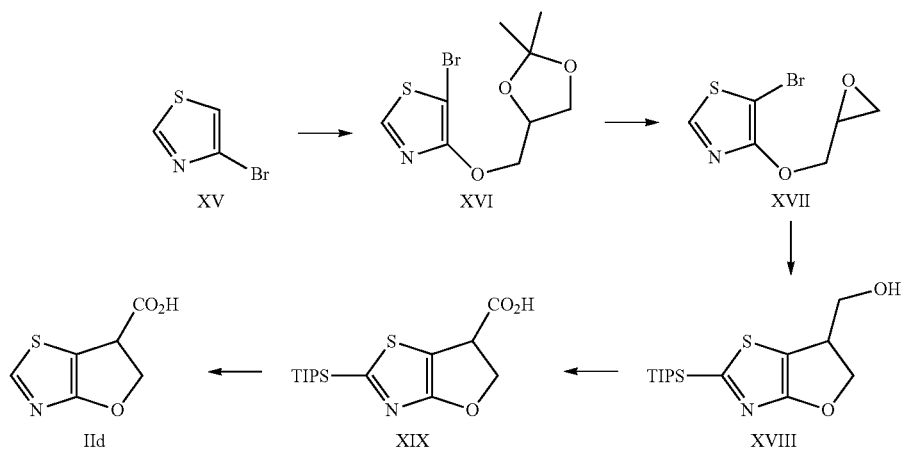

Compounds of formula (III), if not commercially available, can be prepared following the procedures outlined in the schemes below and in the experimental part.

Compounds of formula (III), wherein R⁵ represents hydrogen and m represents 1 or 2 can be prepared from halides (XX), wherein X is preferably bromide or iodide and $R^a$ represents substituted phenyl-($C_1$-$C_2$)alkyl, via a cyanation with NaCN or KCN in a solvent like $CH_3CN$, EtOH or DMF preferably at temperatures between RT and 65° C. (scheme 6). The formed nitriles (XXI) can be reduced by hydrogenation with Raney Nickel as catalyst in a solvent such as $NH_3$ in MeOH. Alternatively, a reducing agent such as $BH_3$ in THF preferably at temperatures between 0° C. and 65° C. or such as $LiAlH_4$ in a solvent like THF or $Et_2O$ preferably at temperatures between 0° C. and RT can be used to form amines (IIIa). In analogy, compounds of formula (III), wherein R¹ and R⁵ represent hydrogen and m represents 0 (such as benzyl) can be prepared by reduction of nitriles (XXI) wherein $R^a$ represents substituted phenyl (and notably by reduction with $BH_3$ in THF).

Scheme 6: Synthesis of compounds of formula (IIIa) and (IIIb)

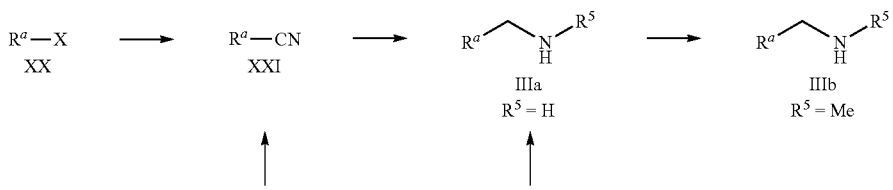

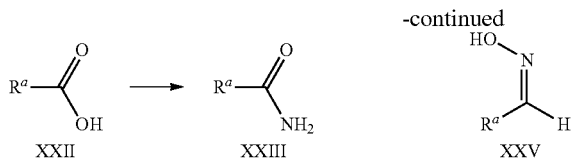
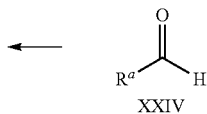

Alternatively, nitriles of formula (XXI) can be synthesized starting from carboxylic acids of formula (XXII), wherein $R^a$ represents substituted phenyl-($C_1$-$C_2$)alkyl or substituted phenyl, by preparing the corresponding carboxamides (XXIII) under standard amide formation conditions, such as EDC.HCl/HOBt in a solvent like DCM or DMF and ammonia (scheme 6). The carboxamides (XXIII) can be dehydrated to nitriles (XXI) using TFAA as dehydrating agent in the presence of $Et_3N$ in a solvent such as DCM preferably at temperatures between 0° C. and RT.

Alternatively, compounds of formula (III), wherein $R^5$ represents hydrogen and m represents 0, 1, or 2 can be prepared in two steps from aldehydes of formula (XXIV), wherein $R^a$ represents substituted phenyl-($C_1$-$C_2$)alkyl or substituted phenyl, via formation of the corresponding oximes (XXV) using hydroxylamine hydrochloride under standard conditions such as in a solvent like EtOH at temperatures between RT and 60° C. followed by a reduction of the respective oximes using zinc dust in a solvent like acetic acid preferably at temperatures between 0° C. and RT or by using $BH_3$ in a solvent like THF preferably at temperatures between RT and 60° C. (scheme 6).

Compounds of formula (III), wherein $R^5$ represents methyl, can be synthesized by a reductive amination reaction of a primary amine of formula (IIIa) using formaldehyde via catalytic hydrogenation in the presence of a suitable catalyst such as $PtO_2$ or Raney Nickel in a solvent like EtOH preferably at temperatures between RT and 45° C. or in the presence of a reducing agent such as $NaBH_4$ or $NaBH(OAc)_3$ in a solvent like MeOH or $ClCH_2CH_2Cl$ at temperatures between RT and 65° C. Alternatively, methylation with MeI in the presence of a base such as NaH in a suitable solvent like THF or DMF at temperatures between 0° C. and RT can be done (scheme 6).

Compounds of formula (XXVI), wherein $R^3$ is a ($C_1$-$C_4$) alkyl, ($C_3$-$C_6$)cycloalkyl, ($C_1$-$C_4$)alkoxy, hydroxy-($C_2$-$C_3$) alkoxy, hydroxy-($C_1$-$C_3$)alkyl, ($C_1$-$C_2$)alkoxy-($C_1$-$C_2$)alkyl or hydroxy-($C_2$-$C_3$)alkoxy-($C_1$-$C_2$)alkyl substituent and wherein "aryl" means a phenyl group as depicted in formula (III), which phenyl is (1) optionally substituted with one further $R^3$ group, (2) substituted with $R^2$ and (3) substituted with $R^b$, can be prepared following the procedures outlined in scheme 7. $R^b$ represents a precursor to the $R^5NH$—$(CH_2)_m$— $CHR^1$-moiety of compounds of formula (III) such as cyano, cyano-($C_1$-$C_2$)alkyl, formyl, or PGN-($C_1$-$C_3$)alkyl wherein PG represents an amine protecting group. In case $R^b$ represents a cyano or cyano-($C_1$-$C_2$)alkyl group, compounds of formula (III) may be prepared from compounds of formula (XXVI) according to the procedure described for the transformation of compounds of formula (XXI) to compounds of formula (IIIa) (scheme 6). In case $R^b$ represents a formyl group, compounds of formula (III) may be prepared from compounds of formula (XXVI) according to the procedure described for the transformation of compounds of formula (XXIV) to compounds of formula (IIIa) (scheme 6). In case $R^b$ represents a PGN-($C_1$-$C_3$)alkyl group wherein PG represents a phthalimide protecting group, compounds of formula (III) may be prepared from compounds of formula (XXVI) by removal of the phthalimide group with, for instance, hydrazine in a solvent like EtOH at temperatures around RT.

Compounds of formula (XXVI), wherein $R^3$ is ($C_1$-$C_4$) alkyl or ($C_3$-$C_6$)cycloalkyl and wherein "aryl" means a phenyl group as depicted in formula (III), which phenyl is (1) optionally substituted with one further $R^3$ group, (2) substituted with $R^2$ and (3) substituted with $R^b$, wherein $R^b$ represents PGN-($C_1$-$C_3$)alkyl and PG represents an amine protecting group such as a phthalimide protecting group, can be prepared from compounds of formula (XXVII) wherein X, as a precursor of $R^3$, is a halogen atom (preferably bromide) by a Suzuki type coupling reaction. The Suzuki reaction can be carried out for instance with ($C_1$-$C_4$)alkylboronic acid derivatives or ($C_3$-$C_6$)cycloalkylboronic acid derivatives (e.g. ethylboronic acid) in the presence of a suitable base such as $K_3PO_4$ and a palladium catalyst like palladium acetate with triphenylphosphine in a solvent such as toluene or dioxane preferably at temperatures between RT and 100° C.

Compounds of formula (XXVI), wherein $R^3$ is ($C_1$-$C_4$) alkoxy or hydroxy-($C_2$-$C_3$)alkoxy and wherein "aryl" means a phenyl group as depicted in formula (III), which phenyl is (1) optionally substituted with one further $R^3$ group, (2) substituted with $R^2$ and (3) substituted with $R^b$, wherein $R^b$ represents formyl, cyano or cyano-($C_1$-$C_2$)alkyl, can be prepared from the respective phenols of formula (XXVIII) by an alkylation reaction using a base like $K_2CO_3$ or $Cs_2CO_3$ in a solvent such as DMF in the presence of the appropriate alkylating agent such as ($C_1$-$C_4$)alkyl-L or hydroxy-($C_2$-$C_3$)alkyl-L, wherein L represents a leaving group such as bromide or iodide (e.g., iodomethane).

Compounds of formula (XXVI), wherein $R^3$ is hydroxymethyl, ($C_1$-$C_2$)alkoxymethyl, or hydroxy-($C_2$-$C_3$)alkoxymethyl and wherein "aryl" means a phenyl group as depicted in formula (III), which phenyl is (1) optionally substituted with one further $R^3$ group, (2) substituted with $R^2$ and (3) substituted with $R^b$, wherein $R^b$ represents cyano or cyano-($C_1$-$C_2$) alkyl, can be prepared from the respective methylated compounds of formula (XXIX) by (1) a Wohl-Ziegler type bromination reaction using standard conditions like NBS in the presence of catalytical amounts of AIBN in a solvent such as chlorobenzene preferably at temperatures between 40° C. and 80° C. and (2) followed by a substitution reaction of the respective benzyl bromide with for instance NaOH, NaOMe, NaOEt or AcO—($C_2$-$C_3$)alkyl-ONa.

Compounds of formula (XXVI), wherein $R^3$ is hydroxyethyl, ($C_1$-$C_2$)alkoxyethyl or hydroxy-($C_2$-$C_3$)alkoxyethyl and wherein "aryl" means a phenyl group as depicted in formula (III), which phenyl is (1) optionally substituted with one further $R^3$ group, (2) substituted with $R^2$ and (3) substituted with $R^b$, wherein $R^b$ represents cyano or cyano-($C_1$-$C_2$) alkyl, can be prepared from compounds of formula (XXVII), wherein X represents halogen by (1) a Stille type coupling reaction using for instance ethyl tributylstannylacetate in the presence of a suitable catalyst such as dichlorobis(tri-o-tolylphosphine)palladium optionally in combination with zinc bromide in a solvent such as DMF preferably at temperatures between RT and 80° C. and (2) followed by a reduction of the corresponding ester with $NaBH_4$ in a solvent such as diglyme or with $LiAlH_4$ in a solvent such as THF preferably at temperatures between 0° C. and RT and optionally, (3) followed by an alkylation reaction using a base like $K_2CO_3$ or $Cs_2CO_3$ in a solvent such as DMF in the presence of the appropriate alkylating agent such as ($C_1$-$C_2$)alkyl-L or hydroxy-($C_2$-$C_3$)alkyl-L, wherein L represents a leaving group such as bromide or iodide (e.g., iodomethane).

Compounds of formula (XXVI), wherein $R^3$ is hydroxypropyl and wherein "aryl" means a phenyl group as depicted in formula (III), which phenyl is (1) optionally substituted with one further $R^3$ group, (2) substituted with $R^2$ and (3) substituted with $R^b$, wherein $R^b$ represents cyano or cyano-$(C_1-C_2)$alkyl, can be prepared from compounds of formula (XXVII), wherein X represents halogen by (1) a Heck type coupling using for instance methyl acrylate in the presence of a base such as $Et_3N$ and a suitable palladium catalyst like tetrakis(triphenylphosphine)palladium in a solvent such as DMF preferably at temperatures between RT and 100° C. and (2) followed by a reduction of the corresponding unsaturated ester with $NaBH_4$ in a solvent such as diglyme or with $LiAlH_4$ in a solvent such as THF preferably at temperatures between 0° C. and RT.

Scheme 7: Synthesis of compounds of formula (XXVI)

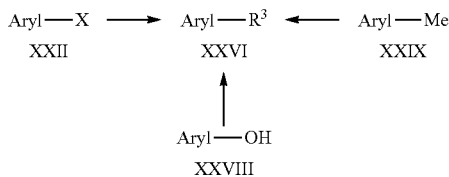

Compounds of formula (III), wherein $R^5$ represents hydrogen, m represents 0, and $R^1$ represents hydroxy-$(C_1-C_2)$alkyl can be prepared from amino acid derivatives (XXX), wherein $R^c$ represents phenyl, which is substituted with $R^2$ and optionally substituted with one or two $R^3$, and R represents $(C_1-C_4)$alkyl (preferably methyl or ethyl), via reduction with $LiAlH_4$ or $BH_3$ in a solvent such as THF or by using $NaBH_4$ in MeOH preferably at temperatures between 0° C. and RT to form the respective aminoalcohols (scheme 8). Compounds of formula (IIId), wherein $R^5$ represents methyl, can be synthesized under the methylation conditions as described for the synthesis of compounds of formula (IIIb).

Scheme 8: Synthesis of compounds of formula (IIIc) and (IIId)

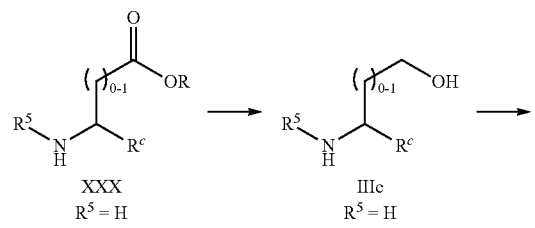

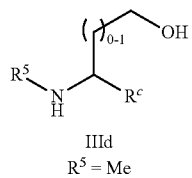

Compounds of formula (III), wherein $R^5$ represents hydrogen, m represents 0, and $R^1$ and $R^2$ together represent —$CH_2CH_2$— or —$CH_2CH_2CH_2$— can be prepared in two steps from ketones (XXXI), wherein $R^3$ represents halogen and p represents 0, 1, or 2 via (1) oxime formation using standard conditions such as O-methylhydroxylamine in a solvent like MeOH optionally in the presence of NaOAc to form compounds of formula (XXXII) and (2) a hydrogenation reaction in the presence of a reducing agent such as $BH_3$ in a solvent like THF preferably at temperatures between RT and 60° C. to form amines of formula (IIIe), wherein m represents 0 and $R^3$ represents halogen (scheme 9). Compounds of formula (IIIf), wherein $R^5$ represents methyl, can be prepared under the methylation conditions mentioned above.

Compounds of formula (III), wherein $R^5$ represents hydrogen, m represents 1 or 2, and $R^1$ and $R^2$ together represent —$CH_2CH_2$— or —$CH_2CH_2CH_2$— can be prepared by reduction of nitriles (XXXIII), wherein q represents 0 or 1 and $R^3$ represents halogen with $H_2$ and Raney Nickel as catalyst in a solvent such as $NH_3$ in MeOH (scheme 9). Alternatively, a reducing agent such as $BH_3$ in THF preferably at temperatures between 0° C. and 65° C. or such as $LiAlH_4$ in a solvent like THF or $Et_2O$ preferably at temperatures between 0° C. and RT can be used to form amines of formula (IIIe), wherein m represents 1 or 2. Compounds of formula (IIIf), wherein $R^5$ represents methyl, can be prepared under the methylation conditions mentioned above. Nitriles (XXXIII), wherein q represents 0 can be prepared from ketones (XXXI), wherein $R^3$ represents halogen via a van Leusen reaction utilizing TosMIC and a base like tBuOK in a solvent such as DME/EtOH at temperatures between 0° C. and RT. Nitriles (XXXIII), wherein q represents 1 can be prepared in two steps from ketones (XXXI), wherein $R^3$ represents halogen via (1) Homer-Wadsworth-Emmons reaction utilizing $(EtO)_2P(=O)CH_2CN$ and a base such as NaH or tBuOK in a solvent like THF at temperatures between 0° C. and RT and (2) reduction with $H_2$ and a catalyst like Pd on charcoal in a solvent like MeOH at temperatures between RT and 65° C.

Scheme 9: Synthesis of compounds of formula (IIIe) and (IIIf)

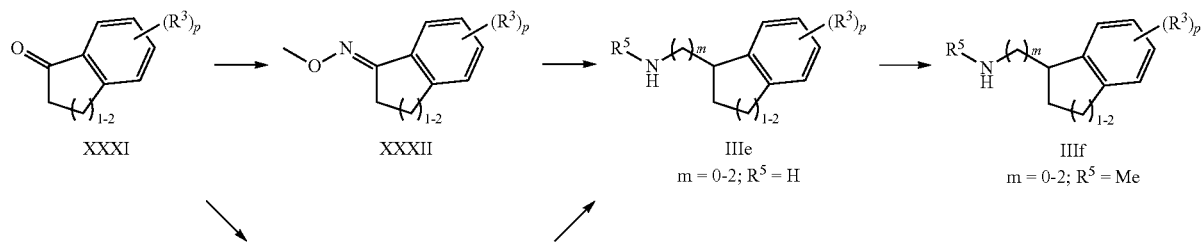

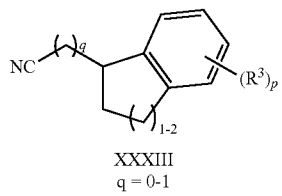

XXXIII
q = 0-1

Alternatively, compounds of formula (III), wherein $R^1$ and $R^5$ represent hydrogen and m represents 0 can be prepared from aniline derivatives (XXXIV), wherein aryl means phenyl which is substituted with $R^2$ and optionally substituted with $R^3$ by a Meerwein arylation type reaction using a Cu(II) salt like $CuCl_2$, tBu-nitrite and 1,1-dichloroethylene in a solvent like MeCN followed by refluxing in MeOH in the presence of sodium methoxide and subsequent treatment with concentrated $H_2SO_4$, preferably at a temperature between RT and 90° C. (scheme 10). Hydrolysis of the obtained ester derivatives using standard conditions such as NaOH or LiOH in a mixture of water and a suitable organic solvent such as MeOH, EtOH or THF gives the corresponding compounds of formula (XXXV). A Curtius rearrangement using DPPA in a suitable solvent like toluene preferably at temperatures around 100° C. followed by treatment with water or potassium trimethylsilanolate at temperatures around 0° C. leads to compounds of formula (IIIg), wherein $R^5$ is hydrogen. Compounds of formula (IIIh), wherein $R^5$ represents methyl can be prepared under the methylation conditions mentioned above.

Scheme 10: Synthesis of compounds of formula (IIIg) and (IIIh)

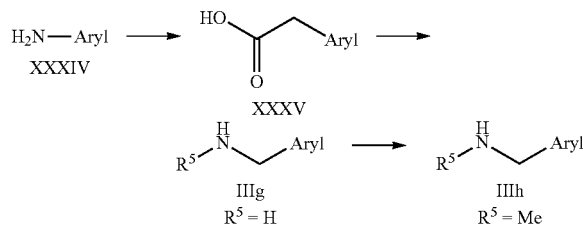

Experimental Part

Abbreviations (as used herein and in the description above)
Ac acetyl
AIBN azobisisobutyronitrile
anh. anhydrous
aq aqueous
Ar argon
nBu butyl
tBu tert-butyl
CC column chromatography
cod 1,5-cyclooctadiene
conc. concentrated
comb. combined
dba dibenzylideneacetone
DCM dichloromethane
DHP 3,4-dihydro-2H-pyran
DIPA diisopropylamine
DIPEA diisopropylethylamine
DME dimethoxyethane
DMF dimethylformamide
DMP Dess-Martin periodinane
DMSO dimethyl sulfoxide
DPPA diphenylphosphoryl azide
Et ethyl
EDC. HCl N-(3-dimethylaminopropyl)-N'-ethylcarbodiimide hydrochloride
h hour(s)
HATU O-(7-azabenzotriazol-1-yl)-N,N,N',N'-tetramethyluronium hexafluorophosphate
Hept heptane
HOAt 1-hydroxy-7-azabenzotriazole
HOBt 1-hydroxybenzotriazole hydrate
HV high vacuum
LC-MS liquid chromatography-mass spectrometry
LDA lithium diisopropylamide
M molar
Me methyl
MeCN acetonitrile
min minute(s)
NBS N-bromosuccinimide
NMR nuclear magnetic resonance
org. organic
PG protecting group
Ph phenyl
PPTS pyridinium p-toluenesulfonate
PTSA p-Toluenesulfonic acid
PyBOP (benzotriazol-1-yloxy)tripyrrolidinophosphonium hexafluorophosphate
RT room temperature
sat. saturated
soln. solution
TBAF tetra-n-butylammonium fluoride
TBS tert-butyldimethylsilyl
Tf trifluoromethanesulfonyl
TFA trifluoroacetic acid
TFAA trifluoroacetic anhydride
THF tetrahydrofuran
THP tetrahydropyran
TIPS triisopropylsilyl
TMS trimethylsilyl
TosMIC toluenesulfonylmethyl isocyanide
$t_R$ retention time
UV ultra-violet
Vis visible A. Characterization Methods Used
Nuclear Magnetic Resonance:
Brucker Avance 400, 400 MHz; chemical shifts are given in ppm relative to the solvent used; multiplicities: s=singlet, d=doublet, t=triplet, q=quadruplet, m=multiplet, br=broad, coupling constants are given in Hz.
Analytical HPLC-MS Methods:
HPLC-MS analyses were performed on a Thermo MSQ mass spectrometer with a Dionex Ultimate HPG-3000 pump and a Dionex Ultimate 3000 photodiode array detector.
(1) eluents: A: $H_2O$+0.05% HCOOH, $CH_3CN$; gradient: 5% B→95% B (0.0 min-2.0 min), 95% B (2.0 min-2.3 min);

flow: 1.8 mL/min; detection: UV/Vis+MS; $t_R$ is given in min; column: Ascentis Express C18; 2.7 um, 2.1×50 mm.

(2) eluents: A: $H_2O$+0.05% $NH_4OH$, $CH_3CN$; gradient: 5% B→95% B (0.0 min-2.0 min), 95% B (2.0 min-2.3 min); flow: 1.8 mL/min; detection: UV/Vis+MS, $t_R$ is given in min; column: Ascentis Express C18, 2.7 um, 2.1×50 mm.

HPLC-MS analyses were performed on a Thermo MSQ Plus mass spectrometer with a Dionex HPG-3200RS pump (or Agilent G4220A) and a Dionex DAD-3000RS photodiode array detector (or Agilent G4212A).

(3) eluents: A: $H_2O$+0.04% TFA, $CH_3CN$; gradient: 5% B→95% B (0.0 min-1.0 min), 95% B (1.0 min-1.5 min); flow: 4.5 mL/min; detection: UV/Vis+MS, $t_R$ is given in min; column: Waters XBridge C18, 2.5 um, 4.6×30 mm.

(4) eluents: A: $H_2O$+0.04% TFA, B: $CH_3CN$; gradient: 2% B→40% B (0.0 min-0.8 min), 40% B→95% B (0.8 min-1.2 min), 95% B (1.2 min-1.5 min); flow: 4.5 mL/min; detection: UV/Vis+MS, $t_R$ is given in min; column: Waters XBridge C18, 2.5 um, 4.6×30

(5) eluents: A: $H_2O$+0.04% TFA, B: $CH_3CN$; gradient: 5% B→95% B (0.0 min-1.0 min), 95% B (1.0 min-1.5 min); flow: 4.5 mL/min; detection: UV/Vis+MS, $t_R$ is given in min; column: Waters Atlantis T3, 5 um, 4.6×30 mm.

Purification Methods Used
Preparative LC-MS Methods:

Preparative HPLC/MS purifications were performed on a Waters system, equipped with a binary gradient module (2545), a HPLC pump (515), a photodiode array detector (2998) and a mass detector (3100).

eluents acidic: A: $H_2O$+0.1% HCOOH, B: $CH_3CN$+0.1% HCOOH; eluents basic: A: $H_2O$+0.1% $NH_4OH$, B: $CH_3CN$+0.1% $NH_4OH$; flow: 40 mL/min; column: Waters XBridge C18, 5 um 19×50 mm.

normal gradient: 75% A (0.0 min-0.2 min), 75% A→65% A (0.2 min-0.3 min), 65% A→35% A (0.3 min-3.2 min), 35% A 5% A (3.2 min-3.3 min), 5% A (3.3 min-4.3 min).

polar gradient: 90% A (0.0 min-0.2 min), 90% A→80% A (0.2 min-0.3 min), 80% A→50% A (0.3 min-3.2 min), 50% A→5% A (3.2 min-3.3 min), 5% A (3.3 min-4.3 min).

|  | acidic | basic |
|---|---|---|
| polar gradient | (A) | (C) |
| normal gradient | (B) | (D) |

Preparative HPLC/MS purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector.

eluents acidic: A: $CH_3CN$, B: $H_2O$+0.5% HCOOH; eluents basic: A: $CH_3CN$, B: $H_2O$+0.5% $NH_4OH$; flow: 75 mL/min; column: Waters XBridge C18, 10 um, 30×75 mm.

normal gradient: 80% B→5% B (0.0 min-4.0 min), 5% B (4.0 min-6.0 min).

polar gradient: 90% B→5% B (0.0 min-4.0 min), 5% B (4.0 min-6.0 min).

|  | acidic | basic |
|---|---|---|
| polar gradient | (E) | (G) |
| normal gradient | (F) | (H) |

Method (I): eluents: A: $CH_3CN$, B: $H_2O$+0.5% HCOOH; gradient: 100% B (0.0 min-1.0 min), 100% B 80% B (1.0 min-3.5 min), 80% B→5% B (3.5 min-4.0 min), 5% B (4.0 min-6.0 min); flow: 75 mL/min; column: Waters Atlantis T3 OBD, 10 um, 30×75 mm.

Method (J): eluents: A: $CH_3CN$, B: $H_2O$+0.5% HCOOH gradient: 90% B→5% B (0.0 min-4.0 min), 5% B (4.0 min-6.0 min); flow: 75 mL/min; column: Waters Atlantis T3 OBD, 10 um, 30×75 mm.

Column Chromatography (CC) (Method K):

CC was performed using silica gel 60 Merck (0.063-0200 mm) or using pre-packed cartridges (SNAP KP-Sil™) from Biotage®.

Extraction (Method L, M):

(L): the reaction mixture was diluted with DCM, washed with aq. sat. $NaHCO_3$ and brine, dried over $MgSO_4$, and conc. in vacuo. The residue was suspended in DCM and filtrated.

(M): the reaction mixture was filtrated, the residue was dissolved in DCM, washed with aq. sat. $NaHCO_3$, aq. citric acid and brine, dried over $MgSO_4$, and conc. in vacuo.

Trituration (Method N):

(N): the residue was suspended in DCM and filtrated.

Racemates can be separated into their enantiomers by preparative chiral HPLC.

The following examples illustrate the invention but do not at all limit the scope thereof.

A. Preparation of Precursors and Intermediates

A.1. Synthesis of Carboxylic Acid Derivatives (II)

A.1.1. Synthesis of 4,5,6,7-tetrahydrobenzo[d]thiazole-7-carboxylic acid

A.1.1.1. Methyl 2-bromo-3-oxocyclohexanecarboxylate

At 0° C., NBS (9.08 g, 51.0 mmol) was added to a soln. of methyl cyclohex-2-enecarboxylate (5.96 g, 42.5 mmol) [Bioorg. Med. Chem. 1999, 7, 1505-1511] in $THF/H_2O$ (500 mL, 9:1). The mixture was allowed to warm to RT and stirred for 2 h. Subsequently, aq. sat. $Na_2S_2O_3$ and aq. sat. $NaHCO_3$ were added and the mixture was conc. in vacuo.

The residue was partitioned between EtOAc and aq. sat. $NaHCO_3$. The org. layer was washed multiple times with aq. sat. $NaHCO_3$ and brine, dried over $MgSO_4$, and conc. in vacuo.

The residue was dissolved in DCM (386 mL) and DMP (24.54 g, 57.9 mmol) was added at 0° C. The mixture was allowed to warm to RT and stirred for 2 h. Subsequently, the mixture was quenched by the addition of aq. sat. $Na_2S_2O_3$ and aq. sat. $NaHCO_3$, diluted with $H_2O$, and extracted with DCM. The comb. org. layers were washed with brine, dried over $MgSO_4$, and conc. in vacuo. Purification by means of CC (0-0.5% MeOH/DCM) provided a yellow oil.

$^1$H-NMR ($CDCl_3$) δ: 4.75 (dd, J=6.7, 1.0 Hz, 0.2H), 4.65 (d, J=3.7 Hz, 0.8H), 3.75, 3.75 (2s, 3H), 3.16-3.01, 2.85-2.79, 2.47-2.39, 2.35-2.29 (4m, 3H), 2.28-1.95, 1.88-1.79, 1.72-1.59 (3m, 4H).

A.1.1.2. Methyl 4,5,6,7-tetrahydrobenzo[d]thiazole-7-carboxylate

At 0° C., finely crushed $P_4S_{10}$ (9.35 g, 21.0 mmol) was added to a mixture of formamide (4.73 g, 105.0 mmol) in dioxane (28.5 mL). Subsequently, the mixture was stirred in a sealed vial at 100° C. for 1.5 h, cooled to RT and filtrated. The filtrate was added to a mixture of methyl 2-bromo-3-oxocyclohexanecarboxylate (2.06 g, 8.76 mmol) in dioxane (16.5 mL) and stirred in a sealed vial at 80° C. overnight. The mixture was quenched by the addition of aq. sat. NaHCO$_3$ and extracted with EtOAc. The comb. org. layers were washed with brine, dried over MgSO$_4$, and conc. in vacuo. Purification by means of CC (10-40% EtOAc/Hept) provided a yellow oil.

LC-MS (3): $t_R$=0.47 min; [M+H]+: 198.16.

A.1.1.3. 4,5,6,7-Tetrahydrobenzo[d]thiazole-7-carboxylic acid

A mixture of methyl 4,5,6,7-tetrahydrobenzo[d]thiazole-7-carboxylate (1.22 g, 6.11 mmol) and LiOH.H$_2$O (0.39 g, 9.17 mmol) in THF/MeOH/H$_2$O (60 mL, 3:1:1) was stirred at RT for 75 min. The mixture was acidified to pH=3 and extracted with DCM. The comb. org. layers were dried over MgSO$_4$ and conc. in vacuo to provide a yellow solid.

LC-MS (3): $t_R$=0.32 min; [M+H]+: 184.21.

A.1.2. Synthesis of 2-amino-4,5,6,7-tetrahydrobenzo[d]thiazole-7-carboxylic acid

A.1.2.1. Methyl 2-amino-4,5,6,7-tetrahydrobenzo[d]thiazole-7-carboxylate

A soln. of methyl 2-bromo-3-oxocyclohexanecarboxylate (1.00 g, 4.25 mmol) and thiourea (0.36 g, 4.68 mmol) in EtOH (16 mL) was stirred at 70° C. overnight. Subsequently, the mixture was quenched with aq. sat. NaHCO$_3$ and extracted with EtOAc. The comb. org. layers were washed with brine, dried over MgSO$_4$, and conc. in vacuo. Purification by means of CC (0-1% MeOH/DCM) provided a yellow solid.

LC-MS (3): $t_R$=0.37 min; [M+H]+: 213.19.

A.1.2.2. 2-Amino-4,5,6,7-tetrahydrobenzo[d]thiazole-7-carboxylic acid

A mixture of methyl 2-amino-4,5,6,7-tetrahydrobenzo[d]thiazole-7-carboxylate (52 mg, 0.24 mmol) and LiOH.H$_2$O (12 mg, 0.29 mmol) in THF/MeOH/H$_2$O (2.5 mL, 3:1:1) was stirred at RT for 2 h. The mixture was neutralized with aq. HCl and conc. in vacuo. The crude yellow solid was used without any further purification.

LC-MS (3): $t_R$=0.28 min; [M+H]+: 199.14.

A.1.3. Synthesis of 2-methyl-4,5,6,7-tetrahydrobenzo[d]thiazole-7-carboxylic acid

A.1.3.1. Methyl 2-methyl-4,5,6,7-tetrahydrobenzo[d]thiazole-7-carboxylate

A soln. of methyl 2-bromo-3-oxocyclohexanecarboxylate (150 mg, 0.64 mmol) and thioacetamide (53 mg, 0.70 mmol) in EtOH (3 mL) was stirred at 85° C. overnight. Subsequently, the mixture was quenched with aq. sat. NaHCO$_3$ and extracted with EtOAc. The comb. org. layers were washed with brine, dried over MgSO$_4$, and conc. in vacuo. Purification by means of CC (0-40% EtOAc/Hept) provided a yellow oil.

LC-MS (3): $t_R$=0.44 min; [M+H]+: 212.17.

A.1.3.2. 2-Methyl-4,5,6,7-tetrahydrobenzo[d]thiazole-7-carboxylic acid

A mixture of methyl 2-methyl-4,5,6,7-tetrahydrobenzo[d]thiazole-7-carboxylate (59 mg, 0.28 mmol) and LiOH.H$_2$O (14 mg, 0.33 mmol) in THF/MeOH/H$_2$O (2.5 mL, 3:1:1) was stirred at RT for 2 h. The mixture was acidified to pH=3 and extracted with EtOAc. The comb. org. layers were dried over MgSO$_4$, and conc. in vacuo.

LC-MS (3): $t_R$=0.30 min; [M+H]+: 198.17.

A.1.4. Synthesis of 2-phenyl-4,5,6,7-tetrahydrobenzo[d]thiazole-7-carboxylic acid

A.1.4.1. Synthesis of methyl 2-phenyl-4,5,6,7-tetrahydrobenzo[d]thiazole-7-carboxylate A soln. of methyl 2-bromo-3-oxocyclohexanecarboxylate (100 mg, 0.43 mmol) and thiobenzamide (64 mg, 0.47 mmol) in EtOH (2 mL) was stirred at 85° C. overnight. Subsequently, the mixture was quenched with aq. sat. NaHCO$_3$ and extracted with EtOAc. The comb. org. layers were washed with brine, dried over MgSO$_4$, and conc. in vacuo. Purification by means of CC (2-15% EtOAc/Hept) provided a yellow oil.

LC-MS (3): $t_R$=0.83 min; [M+H]+: 273.85.

A.1.4.2. Synthesis of 2-phenyl-4,5,6,7-tetrahydrobenzo[d]thiazole-7-carboxylic acid A mixture of methyl 2-phenyl-4,5,6,7-tetrahydrobenzo[d]thiazole-7-carboxylate (12.0 mg, 0.044 mmol) and LiOH.H$_2$O (2.7 mg, 0.065 mmol) in THF/MeOH/H$_2$O (1 mL, 3:1:1) was stirred at RT for 45 min. The mixture was acidified to pH=3 and extracted with DCM. The comb. org. layers were dried over MgSO$_4$, and conc. in vacuo.

LC-MS (3): $t_R$=0.66 min; [M+H]+: 260.13.

A.1.5. Synthesis of 2-bromo-4,5,6,7-tetrahydrobenzo[d]thiazole-7-carboxylic acid

A.1.5.1. Methyl 2-bromo-4,5,6,7-tetrahydrobenzo[d]thiazole-7-carboxylate

At RT methyl 2-amino-4,5,6,7-tetrahydrobenzo[d]thiazole-7-carboxylate (735 mg, 3.46 mmol) was added portionwise to a mixture of copper(II)bromide (1160 mg, 5.19 mmol), tert-butyl nitrite (595 mg, 5.19 mmol) and MeCN (65 mL) under an Ar-atmosphere. The mixture was stirred at RT for 20 min, then, for 15 min at 55° C. The mixture was conc. in vacuo and purified by CC (0-30% EtOAc/Hept) to provide a yellow solid.

LC-MS (3): $t_R$=0.74 min; [M+H]+: 275.98.

A.1.5.2. 2-Bromo-4,5,6,7-tetrahydrobenzo[d]thiazole-7-carboxylic acid

A mixture of methyl 2-bromo-4,5,6,7-tetrahydrobenzo[d]thiazole-7-carboxylate (150 mg, 0.54 mmol) and LiOH.H$_2$O (34 mg, 0.81 mmol) in THF/MeOH/H$_2$O (5 mL, 3:1:1) was stirred at RT for 90 min. The mixture was diluted with H$_2$O and extracted with DCM. The aq. layer was acidified to pH=3 and extracted with DCM. The comb. org. layers were washed with brine, dried over MgSO4, and conc. in vacuo.

LC-MS (3): $t_R$=0.57 min; [M+H]+: 262.03.

A.1.6. Synthesis of 5,6-dihydro-4H-cyclopenta[d]thiazole-6-carboxylic acid

A.1.6.1. 2-Bromo-3-oxocyclopentanecarbonitrile

Bicyclo[2.2.1]hepta-2,5-diene (0.84 g, 9.14 mmol), followed by Gd(OTf)$_3$ (1.84 g, 3.05 mmol), 2-cyclopenten-1- one (5.00 g, 60.9 mmol) and TMS—CN (9.25 g, 91.4 mmol) were added to a degassed solution of Ni(cod)$_2$ (0.84 g, 3.04 mmol) in THF (160 mL) and the mixture was stirred at RT for 4 h. Subsequently, the mixture was quenched with solid NaHCO$_3$ and aq. sat. NaHCO$_3$ and extracted with EtOAc. The comb. org. layers were washed with brine, dried over MgSO$_4$ and conc. in vacuo. The residue, a yellow oil, was dissolved in THF/H$_2$O (450 mL, 9:1). At 0° C., NBS (11.98 g, 67.3 mmol) was added and the mixture was stirred at 0° C. for 30 min. Subsequently, the mixture was quenched with aq. sat. Na$_2$SO$_3$ and extracted with EtOAc. The comb. org. layers were washed with aq. 5% NaHCO$_3$ and brine, dried over Na$_2$SO$_4$, and conc. in vacuo. The residue was re-dissolved in EtOAc, washed multiple times with aq. 5% NaHCO$_3$ and brine, the combined org. layer were dried over Na$_2$SO$_4$, and conc. in vacuo to provide a brown liquid.

$^1$H-NMR (CDCl$_3$) δ: 4.42 (d, J=7.7 Hz, 0.5; H), 4.34 (d, J=5.8 Hz, 0.5; H), 3.43-3.40 (m, 0.5; H), 3.33-3.28 (m, 0.5; H), 2.72-2.26 (m, 4H).

A.1.6.2. 2-Amino-5,6-dihydro-4H-cyclopenta[d]thiazole-6-carbonitrile

A mixture of 2-bromo-3-oxocyclopentanecarbonitrile (crude from A.1.7.1.; ca. 13 g) and thiourea (13.77 g, 181 mmol) in dioxane (600 mL) was stirred at 80° C. for 1 h. The mixture was allowed to cool to RT, quenched with aq. sat. NaHCO$_3$ and extracted with EtOAc. The comb. org. layers were washed with brine, dried over MgSO$_4$, and conc. in vacuo. Purification by means of CC (2-20% MeOH (0.5% Et$_3$N)/DCM) provided a brown solid.

LC-MS (3): t$_R$=0.19 min; [M+H]+: 166.06.

A.1.6.3. 5,6-Dihydro-4H-cyclopenta[d]thiazole-6-carbonitrile

To a soln. of 2-amino-5,6-dihydro-4H-cyclopenta[d]thiazole-6-carbonitrile (1.00 g, 6.05 mmol) in THF (54 mL) was added tert-butyl nitrite (1.04 g, 9.08 mmol) and the mixture was stirred at 65° C. for 3 h. Subsequently, the mixture was quenched with aq. sat. NaHCO$_3$ and extracted with EtOAc. The comb. org. layers were washed with brine, dried over MgSO$_4$, and conc. in vacuo. Purification by means of CC (10-80% EtOAc/Hept) provided a yellow oil.

LC-MS (4): t$_R$=0.52 min; [M+H]+: 151.13.

A.1.6.4. 5,6-Dihydro-4H-cyclopenta[d]thiazole-6-carboxylic acid

A soln. of 5,6-dihydro-4H-cyclopenta[d]thiazole-6-carbonitrile (265 mg, 1.59 mmol) in aq. conc. HCl was stirred at 90° C. for 45 min in a sealed tube. The mixture was adjusted to pH=3 and extracted with EtOAc. The comb. org. layers were washed with brine, dried over MgSO$_4$, and conc. in vacuo to provide a yellow oil LC-MS (3): t$_R$=0.33 min; [M+H]+: 170.03.

A.1.7. Synthesis of 5,6,7,8-tetrahydro-4H-cyclohepta[d]thiazole-8-carboxylic acid

A.1.7.1. 2-Amino-5,6,7,8-tetrahydro-4H-cyclohepta[d]thiazole-8-carbonitrile Bicyclo[2.2.1]hepta-2,5-diene (0.50 g, 5.45 mmol), followed by Gd(OTf)$_3$ (1.10 g, 1.82 mmol), 2-cyclohepten-1-one (5.00 g, 36.3 mmol) and TMS—CN (5.51 g, 54.5 mmol) were added to a degassed solution of Ni(cod)$_2$ (0.50 g, 1.82 mmol) in THF (100 mL) and the mixture was stirred at RT for 4 h. Subsequently, the mixture was quenched with solid NaHCO$_3$ and aq. sat. NaHCO$_3$ and extracted with EtOAc. The comb. org. layers were washed with brine, dried over MgSO$_4$ and conc. in vacuo.

The residue, a yellow oil, was dissolved in THF/H$_2$O (200 mL, 9:1). At 0° C., NBS (5.53 g, 31.0 mmol) was added and the mixture was stirred at 0° C. for 30 min. Subsequently, the mixture was quenched with aq. sat. Na$_2$SO$_3$ and extracted with EtOAc. The comb. org. layers were washed with aq. 5% NaHCO$_3$ and brine, dried over Na$_2$SO$_4$, and conc. in vacuo. The residue was re-dissolved in EtOAc, washed multiple times with aq. 5% NaHCO$_3$ and brine, the combined org. layer were dried over Na$_2$SO$_4$, conc. in vacuo and the residue was filtrated over a plug of SiO$_2$ with EtOAc/Hept (1:1) as eluent.

After conc. In vacuo, the residue, a brown oil, and thiourea (6.34 g, 83.2 mmol) were dissolved in dioxane (330 mL) and the mixture was stirred at 80° C. for 2 h. Subsequently, the mixture was quenched with aq. sat. NaHCO$_3$ and extracted with EtOAc. The comb. org. layers were washed with brine, dried over MgSO$_4$, and conc. in vacuo. Purification by means of CC (2-20% MeOH/DCM) provided a brown oil.

LC-MS (3): t$_R$=0.34 min; [M+H]+: 194.21.

A.1.7.2. 5,6,7,8-Tetrahydro-4H-cyclohepta[d]thiazole-8-carbonitrile

To a soln. of 2-amino-5,6,7,8-tetrahydro-4H-cyclohepta[d]thiazole-8-carbonitrile (1.00 g, 5.17 mmol) in THF (46 mL) was added tert-butyl nitrite (0.65 g, 5.68 mmol) and the mixture was stirred at 65° C. for 2.5 h. Subsequently, the mixture was quenched with aq. sat. NaHCO$_3$ and extracted with EtOAc. The comb. org. layers were washed with brine, dried over MgSO$_4$, and conc. in vacuo. Purification by means of CC (2-40% EtOAc/Hept), CC (0-1.5% MeOH/DCM) and prep. HPLC (F) provided a yellow oil.

LC-MS (3): t$_R$=0.51 min; [M+H]+: 179.23.

A.1.7.3. 5,6,7,8-Tetrahydro-4H-cyclohepta[d]thiazole-8-carboxylic acid

A soln. of 5,6,7,8-tetrahydro-4H-cyclohepta[d]thiazole-8-carbonitrile (151 mg, 0.84 mmol) in aq. conc. HCl (2 mL) was stirred at 90° C. for 1 h in a sealed tube. The mixture was adjusted to pH=3 and extracted with EtOAc. The combined org. layers were washed with brine, dried over MgSO$_4$, and conc. in vacuo to provide a beige solid.

LC-MS (3): t$_R$=0.36 min; [M+H]+: 198.20.

A.1.8. Synthesis of 2-amino-5,6,7,8-tetrahydro-4H-cyclohepta[d]thiazole-8-carboxylic acid A soln. of 2-amino-5,6,7,8-tetrahydro-4H-cyclohepta[d]thiazole-8-carbonitrile (300 mg, 1.40 mmol) in aq. conc. HCl (7 mL) was stirred at 90° C. for 1 h in a sealed tube. The mixture was adjusted to pH=3, conc. in vacuo, re-dissolved in a DMF/MeCN/H$_2$O mixture and filtrated. The filtrate was purified by prep. HPLC (J) to provide a yellow solid.

LC-MS (3): t$_R$=0.34 min; [M+H]+: 213.20.

A.1.9. Synthesis of 6,7-dihydro-5H-pyrano[2,3-d]thiazole-7-carboxylic acid

A.1.9.1. 3-((tert-Butyldimethylsilyl)oxy)-1-(2,4-dichlorothiazol-5-yl)propan-1-ol At −20° C., a soln. of n-BuLi in hexanes (2.3 M, 10.9 mL, 25.0 mmol) was added to a soln. of DIPA (3.5 mL, 25.0 mmol)

in THF (102 mL). The soln. was stirred at −20° C. for 30 min, then, it was cooled to −78° C. and a soln. of 2,4-dichlorothiazole (3.50 g, 22.7 mmol) in THF (16 mL) was added. The mixture was stirred at −78° C. for 30 min, then, 3-[(tert-butyldimethylsilyl)oxy]-1-propanal (4.51 g, 22.7 mmol) was added and the mixture was stirred at −78° C. for 1 h. Subsequently, the mixture was quenched with aq. sat. NH$_4$Cl and extracted with EtOAc. The comb. org. layers were washed with brine, dried over MgSO$_4$, and conc. in vacuo. Purification by means of CC (2-15% EtOAc/Hept) provided a yellow oil.

LC-MS (3): $t_R$=1.08 min; [M+H]+: 342.08.

A.1.9.2. 5-(3-((tert-Butyldimethylsilyl)oxy)-1-((tetrahydro-2H-pyran-2-yl)oxy)propyl)-2,4-dichlorothiazole A soln. of 3-((tert-butyldimethylsilyl)oxy)-1-(2,4-dichlorothiazol-5-yl)propan-1-ol (6.62 g, 19.3 mmol), 3,4-dihydro-2H-pyran (8.9 mL, 96.7 mmol) and PPTS (0.49 g, 1.93 mmol) in DCM (75 mL) was stirred under reflux for 2 h. Subsequently, the volatiles were removed in vacuo and the residue was purified by means of CC (1-10% EtOAc/Hept) to provide the product as colorless oil as an isomeric mixture.

LC-MS (3): $t_R$=1.27 min; 1.28 min; [M+H]+: 426.11; 426.10.

A.1.9.3. 5-(3-((tert-Butyldimethylsilyl)oxy)-1-((tetrahydro-2H-pyran-2-yl)oxy)propyl)-4-chlorothiazole At −78° C., a soln. of n-BuLi in hexanes (2.2 M, 9.6 mL, 21.0 mmol) was added to a soln. of 5-(3-((tert-butyldimethylsilyl)oxy)-1-((tetrahydro-2H-pyran-2-yl)oxy)propyl)-2,4-dichlorothiazole (6.89 g, 16.2 mmol) in THF (125 mL). The mixture was stirred at −78° C. for 45 min, then, quenched by the addition of aq. sat. NaHCO$_3$ and extracted with EtOAc. The comb. org. layers were washed with brine, dried over MgSO$_4$, and conc. in vacuo. Purification by means of CC (2-20% EtOAc/Hept) provided the product as a yellow oil as an isomeric mixture.

LC-MS (3): $t_R$=1.15 min; 1.16 min; [M+H]+: 392.17; 392.17.

A.1.9.4. 3-(4—Chlorothiazol-5-yl)-3-((tetrahydro-2H-pyran-2-yl)oxy)propan-1-ol At 0° C., a soln. of TBAF in THF (1 M, 19.2 mL, 19.2 mmol) was added to a. soln. of 5-(3-((tert-butyldimethylsilyl)oxy)-1-((tetrahydro-2H-pyran-2-yl)oxy)propyl)-4-chlorothiazole (6.27 g, 16.0 mmol) in THF (80 mL). The mixture was allowed to warm to RT and stirred overnight. Then, the mixture was quenched by the addition of aq. sat. NaHCO$_3$ and extracted with EtOAc. The comb. org. layers were washed with brine, dried over MgSO$_4$, and conc. in vacuo. Purification by means of CC (20-85% EtOAc/Hept) provided the product as a yellow oil as an isomeric mixture.

LC-MS (3): $t_R$=0.55 min; 0.57 min; [M+H]+: 278.11; 278.10.

A.1.9.5. 7-((Tetrahydro-2H-pyran-2-yl)oxy)-6,7-dihydro-5H-pyrano[2,3-d]thiazole A soln. of 3-(4-chlorothiazol-5-yl)-3-((tetrahydro-2H-pyran-2-yl)oxy)propan-1-ol (520 mg, 1.87 mmol) in MePh (10 mL) was added to a Ar-filled vial charged with Pd(OAc)$_2$ (63 mg, 0.28 mmol), 2-(di-tert-butylphosphino)-1,1'-binaphthyl (140 mg, 0.35 mmol) and (Cs$_2$CO$_3$ 915 mg, 2.81 mmol). The vial was sealed and placed in a preheated oilbath (100° C.) overnight. Subsequently, the mixture was diluted with DCM, filtrated over Celite, and conc. in vacuo. Purification by means of CC (20-80% EtOAc/Hept) provided the product as a yellow oil as an isomeric mixture.

LC-MS (3): $t_R$=0.60 min; 0.64 min; [M+H]+: 241.94; 241.94.

A.1.9.6. 6,7-Dihydro-5H-pyrano[2,3-d]thiazol-7-ol

A soln. of 7-((tetrahydro-2H-pyran-2-yl)oxy)-6,7-dihydro-5H-pyrano[2,3-d]thiazole (895 mg, 3.71 mmol) and PTSA (141 mg, 0.74 mmol) in THF/H$_2$O (7.4 mL, 1:1) was stirred at RT overnight. The mixture was diluted with DCM, dried over Na$_2$SO$_4$, and conc. in vacuo. Purification by means of CC (40-100% EtOAc/Hept) provided a yellow oil.

LC-MS (3): $t_R$=0.23 min; [M+H]+: 158.15.

A.1.9.7. 6,7-Dihydro-5H-pyrano[2,3-d]thiazole-7-carbonitrile

To a mixture of 6,7-dihydro-5H-pyrano[2,3-d]thiazol-7-ol (0.65 g, 4.14 mmol), acetone cyanohydrin (880 mg, 10.3 mmol) and (n-Bu)$_3$P (1.67 g, 8.27 mmol) in THF (79 mL) was added at 0° C. 1,1'-(azodicarbonyl)dipiperidine (2.09 g, 8.27 mmol). The mixture was stirred at 0° C. for 30 min, then, it was allowed to warm to RT and was stirred for 2 h. Subsequently, the reaction mixture was diluted with diisopropyl ether, filtrated and the filtrate was conc. in vacuo. Purification by means of CC (5-70% EtOAc/Hept) provided a yellow solid.

LC-MS (3): $t_R$=0.36 min; [M+H]+: 167.13.

A.1.9.8. 6,7-Dihydro-5H-pyrano[2,3-d]thiazole-7-carboxylic acid

A soln. of 6,7-dihydro-5H-pyrano[2,3-d]thiazole-7-carbonitrile (462 mg, 2.78 mmol) in aq. HCl (32%, 13.9 mL) was stirred at 60° C. for 30 min. Under ice-bath cooling, the pH of the mixture was adjusted to ca. 3, and the mixture was extracted with EtOAc. The comb. org. layers were dried over MgSO$_4$ and conc. in vacuo to provide a beige solid.

LC-MS (3): $t_R$=0.33 min; [M+H]+: 186.18.

A.1.10. Synthesis of 5,6-dihydrofuro[2,3-d]thiazole-6-carboxylic acid

A.1.10.1. 4-((2,2-Dimethyl-1,3-dioxolan-4-yl)methoxy)thiazole

NaH (60% dispersion in mineral oil, 12.19 g, 305.3 mmol) was added portionwise to DL-1,2-isoproylideneglycerol (16.11 g, 1218 mmol) and the mixture was stirred until gas evolution had ceased (ca. 30 min RT, followed by 2 h at 60° C.). Subsequently, 4-bromothiazole (20.00 g, 121.9 mmol) was added and the mixture was stirred at 140° C. for 45 min. Subsequently, the reaction mixture was quenched with aq. sat. NH$_4$Cl and extracted with EtOAc. The comb. org. layers were washed with brine, dried over MgSO$_4$, and conc. in vacuo. The residue was subjected to distillation and the volatiles (HV, 60° C.) were removed. The residue was purified by means of CC (5-40% EtOAc/Hept) to provide a yellow oil.

LC-MS (3): $t_R$=0.52 min; [M+H]+: 216.20.

A.1.10.2. 5-Bromo-4-((2,2-dimethyl-1,3-dioxolan-4-yl)methoxy)thiazole

At 0° C., NBS (11.94 g, 67.1 mmol) was added over 90 min to a soln. of 4-((2,2-dimethyl-1,3-dioxolan-4-yl)methoxy)

thiazole (13.75 g, 63.9 mmol) in MeCN (320 mL). The mixture was further stirred at 0° C. for 30 min, then, it was quenched by the addition of aq. 5% NaHCO$_3$ and extracted with EtOAc. The comb. org. layers were washed with aq. 5% NaHCO$_3$ and brine, dried over MgSO$_4$, and conc. in vacuo.

LC-MS (3): t$_R$=0.74 min; [M+H]+: 294.13.

A.1.10.3. 5-Bromo-4-(oxiran-2-ylmethoxy)thiazole

A soln. of 5-bromo-4-((2,2-dimethyl-1,3-dioxolan-4-yl)methoxy)thiazole (18.80 g, 63.9 mmol) and PPTS (0.80 g, 3.19 mmol) in MeOH (256 mL) was stirred under reflux for 3 h. More PPTS (0.40 g, 1.60 mmol) was added and the mixture was stirred under reflux for additional 2 h. The mixture was conc. in vacuo, the residue was dissolved in MeOH (256 mL) and stirred under reflux for 2 h. The mixture was conc. in vacuo, the residue was dissolved in DCM (256 mL) and treated with trimethyl orthoformate (10.5 mL, 95.8 mmol). The mixture was stirred overnight at RT. Subsequently, additional trimethyl orthoformate (3.5 mL, 31.9 mmol) was added and the mixture was stirred at RT for 1 h. Then, the mixture was conc. in vacuo, the residue was dissolved in DCM (256 mL), treated with AcBr (5.73 mL, 76.7 mmol) and stirred at RT for 90 min. Subsequently, the mixture was conc. in vacuo, the residue was dissolved in MeOH (320 mL) and K$_2$CO$_3$ (17.66 g, 128 mmol) was added to the mixture. After the mixture was stirred at RT for 90 min, the mixture was filtrated and the filtrate was poured into cold aq. sat. NH$_4$Cl. The mixture was extracted with EtOAc, the comb. org. layers were washed with brine, dried over MgSO$_4$, and conc. in vacuo. The residue was purified by means of CC (2-40% EtOAc/Hept) to provide a yellow oil.

LC-MS (3): t$_R$=0.60 min; [M+H]+: 236.06.

A.1.10.4. (2-(Triisopropylsilyl)-5,6-dihydrofuro[2,3-d]thiazol-6-yl)methanol At −78° C., a soln. of n-BuLi in hexanes (2.18 M, 16.7 mL, 36.4 mmol) was added over 30 min to a soln. of 5-bromo-4-(oxiran-2-ylmethoxy)thiazole (7.17 g, 30.4 mmol) in THF (564 mL). The mixture was stirred at −78° C. for 2 h, then, TIPSCl (6.63 mL, 31.0 mmol) was added, the mixture was allowed to warm to RT and stirred at RT for 30 min. Subsequently, the mixture was cooled to −78° C. and treated with a soln. of n-BuLi in hexanes (2.18 M, 13.9 mL, 30.4 mmol). The mixture was stirred at 0° C. for 2 h, then, it was quenched with aq. sat. NaHCO$_3$ and extracted with EtOAc. The comb. org. layers were washed with brine, dried over MgSO$_4$, and conc. in vacuo. The residue was purified by means of CC (100 g KP-Sil, EtOAc/Hept 5-50%), followed by CC (5-50% EtOAc/Hept) to provide a yellow oil.

LC-MS (3): t$_R$=1.01 min; [M+H]+: 314.13.

A.1.10.5. 2-(Triisopropylsilyl)-5,6-dihydrofuro[2,3-d]thiazole-6-carboxylic acid A soln. of (2-(triisopropylsilyl)-5,6-dihydrofuro[2,3-d]thiazol-6-yl)methanol (1.77 g, 5.64 mmol)) in DCM (56 mL) was treated at 0° C. with DMP (2.87 g, 6.77 mmol) portionwise over 1 h. The mixture was stirred at 0° C. for 2 h, then, it was allowed to warm to RT and stirred for 2 h. Subsequently, the mixture was quenched with aq. sat. Na$_2$S$_2$O$_3$ and aq. sat. NaHCO$_3$ and was extracted with DCM. The comb. org. layers were washed with brine, dried over MgSO$_4$, and conc. in vacuo. The residue was dissolved in tert-BuOH (16 mL) and 2-methyl-2-butene (4 mL) and treated at 0° C. dropwise over 30 min with a soln. of NaH$_2$PO$_4$ (2.64 g, 16.9 mmol) and NaClO$_2$ (0.96 g, 8.46 mmol) in H$_2$O (5 mL). The mixture was stirred at RT for 45 min, then, the volatiles were removed in vacuo, the residue was diluted with H$_2$O and extracted with EtOAc. The comb. org. layers were dried over MgSO$_4$ and conc. in vacuo.

LC-MS (3): t$_R$=0.99 min; [M+H]+: 328.24.

A.1.10.6. 5,6-Dihydrofuro[2,3-d]thiazole-6-carboxylic acid

A soln. of TBAF in THF (1 M, 4.9 mL, 4.90 mmol) was added at 0° C. to soln. of 2-(triisopropylsilyl)-5,6-dihydrofuro[2,3-d]thiazole-6-carboxylic acid (1.62 mg, 4.90 mmol) in THF (25 mL). The mixture was stirred at 0° C. for 30 min, AcOH (0.42 mL, 7.35 mmol) was added, and the volatiles were removed in vacuo. The residue was purified by means of prep. HPLC (I) to provide a colorless solid.

LC-MS (3): t$_R$=0.30 min; [M+H]+: 172.05.

A.2. Synthesis of Amines (III)

A.2.1. Synthesis of 2,4-dichloro-6-cyclopropylbenzylamine

A.2.1.1. Synthesis of 2-(2-bromo-4,6-dichlorobenzyl)isoindoline-1,3-dione To a soln. of 1-bromo-2-(bromomethyl)-3,5-dichlorobenzene (1.98 mmol) [J. Med. Chem. 1992, 35, 4221-4229] in 10 mL CH$_3$CN were added phthalimide (1.98 mmol) and K$_2$CO$_3$ (5.93 mmol). The reaction mixture was stirred at 50° C. for 6 h and then at RT overnight. Sat. aq. NaHCO$_3$ soln. was added and the mixture was extracted 3 times with DCM. The comb. org. phases were dried over MgSO$_4$ and conc. in vacuo to obtain the desired product as beige solid.

LC-MS (3): t$_R$=0.99 min; $^1$H NMR (CDCl$_3$) δ: 7.91-7.71 (m, 4H), 7.57 (s, 1H), 7.41 (s, 1H), 5.13 (s, 2H).

A.2.1.2. Synthesis of 2,4-dichloro-6-cyclopropylbenzylamine

To a soln. of 2-(2-bromo-4,6-dichlorobenzyl)isoindoline-1,3-dione (1.96 mmol) in 16 mL toluene and 0.8 mL water were added K$_3$PO$_4$ (6.85 mmol), PPh$_3$ (0.23 mmol), cyclopropylboronic acid (2.35 mmol) and Pd(OAc)$_2$ (0.15 mmol). The mixture was stirred at 80° C. for 24 h when another portion of cyclopropylboronic acid (1.96 mmol) and Pd(OAc)$_2$ (0.15 mmol) were added. The reaction mixture was stirred at 80° C. for further 4 days, cooled to RT, quenched with sat. aq. NaHCO$_3$ solution and extracted with EtOAc. The comb. org. layers were dried over MgSO$_4$ and conc. in vacuo to give a crude white solid. This solid was dissolved in 15 mL EtOH and 12.6 mL of hydrazine monohydrate was added. After stirring at RT for 30 min, EtOAc was added. The aq. phase was basified with 1M NaOH soln. and extracted 3 times with EtOAc. The comb. org. layers were dried over MgSO$_4$ and conc. Purification with CC (KP-NH™ from Biotage) gives the desired compound as red/brown oil.

LC-MS (3): t$_R$=0.60 min; [M+H]+: 216.15.

A.2.2. Synthesis of (2-(aminomethyl)-3,5-dichlorophenyl)methanol

A.2.2.1. Synthesis of 2-(bromomethyl)-4,6-dichlorobenzonitrile

A soln. of 2,4-dichloro-6-methylbenzonitrile (16.9 mmol) in 34 mL chlorobenzene was heated to 50° C. when NBS (18.6 mmol) was added. The flask was purged with Ar before AIBN (1.69 mmol) was added at once still at 50° C. The reaction mixture was then stirred at 78° C. After 2 h and 4 h, another portion of AIBN (1.69 mmol) was added and heating to 78° C. was continued overnight. The solvent was then evaporated off, the resulting residue was redissolved in $Et_2O$ and the remaining solid was removed by filtration. The filtrate was washed twice with 2N HCl solution and brine, it was dried over $MgSO_4$ and conc. in vacuo. Purification with CC (0-100% EtOAc/Hept) gives the desired compound as yellowish solid.

LC-MS (3): $t_R$=0.88 min; $^1$H NMR ($(CD_3)_2SO$) δ: 8.02 (s, 1H), 7.92 (s, 1H), 4.79 (s, 2H).

A.2.2.2. Synthesis of 3,5-dichloro-2-cyanobenzyl acetate

To a soln. of 2-(bromomethyl)-4,6-dichlorobenzonitrile (15.1 mmol) in 30 mL AcOH was added NaOAc (75.7 mmol). The suspension was heated to 100° C. for 2 h. The solvent was evaporated off and the residue partitioned between DCM and water. The org. phase was washed with water, dried over $MgSO_4$ and conc. in vacuo. Purification with CC (5-70% EtOAc/Hept) gives the desired compound as white solid.

LC-MS (5): $t_R$=0.88 min; $^1$H NMR ($(CD_3)_2SO$) δ: 8.02 (s, 1H), 7.76 (s, 1H), 5.23 (s, 2H), 2.12 (s, 3H).

A.2.2.3. Synthesis of (2-(aminomethyl)-3,5-dichlorophenyl)methanol

To a soln. of 3,5-dichloro-2-cyanobenzyl acetate (11.7 mmol) in 50 mL THF was added a soln. of $BH_3$ (50 mmol, 1M in THF). The reaction mixture was heated to 75° C. for 7 h and then cooled to 0° C. Water was added followed by MeOH and the mixture was conc. The residue was taken up in water and EtOAc, acidified with 1N HCl solution and extracted with DCM. The aq. phase was then basified with 1M NaOH soln. and extracted with DCM. The comb. org. layers were dried over $MgSO_4$ and conc. in vacuo. Purification with CC (0-10% MeOH/DCM; 1% $Et_3N$) gives the desired compound as pinkish solid.

LC-MS (5): $t_R$=0.42 min; $^1$H NMR ($(CD_3)_2SO$) δ: 7.46 (s, 1H), 7.38 (s, 1H), 4.60 (s, 2H), 3.76 (s, 2H).

A.2.3. Synthesis of 2,4-dichloro-6-methoxybenzylamine

A.2.3.1. Synthesis of 2,4-dichloro-6-methoxybenzaldehyde

To a soln. of 4,6-dichlorosalicylaldehyde (2.69 mmol) in 5 mL DMF was added $K_2CO_3$ (5.39 mmol) followed by iodomethane (2.96 mmol). The reaction mixture was heated to 50° C. for 3.5 h. At RT, the mixture was diluted with EtOAc and washed 3 times with water and then with brine. The comb. org. layers were dried over $MgSO_4$ and conc. in vacuo to give the desired product as beige solid.

LC-MS (3): $t_R$=0.78 min; $^1$H NMR ($(CD_3)_2SO$) δ: 10.30 (s, 1H), 7.36 (s, 1H), 7.32 (s, 1H), 3.39 (s, 3H).

A.2.3.2. Synthesis of 2,4-dichloro-6-methoxybenzaldehyde oxime

A sol. of 2,4-dichloro-6-methoxybenzaldehyde (2.39 mmol) in 5 mL DMF was cooled to 0° C. and NaOAc (2.63 mmol) followed by hydroxylamine HCl (2.63 mmol) were added. The ice bath was removed and the reaction mixture was stirred at RT for 10 min. The mixture was diluted with EtOAc and washed once with water and brine. The comb. org. layers were dried over $MgSO_4$ and conc. in vacuo to give the desired compound as white solid.

LC-MS (3): $t_R$=0.73 min; [M+H]+: 220.14.

A.2.3.3. Synthesis of 2,4-dichloro-6-methoxybenzylamine

A suspension of 2,4-dichloro-6-methoxybenzaldehyde oxime (2.24 mmol) in 3 mL AcOH was cooled to 0° C. and zinc dust (8.53 mmol) was added. The reaction mixture was stirred at RT for 2 h. It was filtered over a pad of celite and washed with EtOAc and MeOH. The filtrate was conc. and redissolved in water (pH 4 with 2N HCl solution). It was washed once with EtOAc, the aqeous phase was basified with 1M NaOH solution, extracted 3 times with EtOAc and DCM. The comb. org. layers were dried over $MgSO_4$ and conc. in vacuo to give the desired product as yellow solid.

LC-MS (3): $t_R$=0.47 min; [M+$CH_3CN$+H]+: 246.99.

A.2.4. Synthesis of 2-(2-(aminomethyl)-3,5-dichlorophenoxy)ethanol

A.2.4.1. Synthesis of 2-(3,5-dichloro-2-formylphenoxy)ethyl acetate

To a soln. of 4,6-dichlorosalicylaldehyde (3.72 mmol) in 5 mL DMF was added $Cs_2CO_3$ (3.72 mmol) followed by KI (3.72 mmol) and 2-bromoethylacetate (8.68 mmol). The reaction mixture was heated to 100° C. for 4 h and then stirred at RT for 3 days. The mixture was diluted with EtOAc and washed 3 times with water and then with brine. The comb. org. layers were dried over $MgSO_4$ and conc. in vacuo. Purification with CC (20-100% EtOAc/Hept) gives the desired compound as beige solid.

LC-MS (5): $t_R$=0.86 min; [M+H]+: 227.12.

A.2.4.2. Synthesis of 2-(3,5-dichloro-2-((hydroxyimino)methyl)phenoxy)ethyl acetate A soln. of 2-(3,5-dichloro-2-formylphenoxy)ethyl acetate (1.48 mmol) in 2.5 mL DMF was cooled to 0° C. and NaOAc (1.62 mmol) followed by hydroxylamine HCl (1.62 mmol) were added. The ice bath was removed and the reaction mixture was stirred at RT for 1.5 h. The mixture was diluted with EtOAc and washed once with water and brine. The comb. org. layers were dried over $MgSO_4$ and conc. in vacuo. Purification with CC using Hept and EtOAc gives the desired compound as white solid.

LC-MS (5): $t_R$=0.81 min; [M+H]+: 292.25.

A.2.4.3. Synthesis of 2-(2-(aminomethyl)-3,5-dichlorophenoxy)ethanol

A suspension of 2-(3,5-dichloro-2-((hydroxyimino)methyl)phenoxy)ethyl acetate (1.15 mmol) in 2 mL AcOH was cooled to 0° C. and zinc dust (4.36 mmol) was added. The reaction mixture was stirred at RT for 1 h. It was filtered over a pad of celite and washed with EtOAc and MeOH. The filtrate was conc. and redissolved in water (pH 4 with 2N HCl solution). It was washed once with EtOAc, the aqeous phase was basified with 1M NaOH solution, extracted 3 times with EtOAc and DCM. The comb. org. layers were dried over $MgSO_4$ and concentrated in vacuo to give the desired product as white solid.

LC-MS (5): $t_R$=0.46 min; [M+H]+: 236.01.

A.2.5. Synthesis of 2-chloro-3-cyanobenzylamine

A.2.5.1. Synthesis of 3-(bromomethyl)-2-chlorobenzonitrile

A soln. of 2-chloro-3-methylbenzonitrile (6.6 mmol) in 25 mL chlorobenzene was heated to 50° C. when NBS (7.9 mmol) was added. The flask was purged with Ar before AIBN (0.66 mmol) was added at once still at 50° C. The reaction mixture was stirred at 80° C. for 2 h. The solvent was evaporated off, the resulting residue was redissolved in $Et_2O$ and washed 3 times with 1N HCl soln. and brine. It was dried over $MgSO_4$ and conc. in vacuo. Purification with CC (0-15% EtOAc/Hept) gives the desired compound as white solid.

LC-MS (3): $t_R$=0.78 min; $^1$H NMR (($CD_3$)$_2$SO) δ: 7.98 (m, 2H), 7.58 (t, 1H), 4.80 (s, 2H).

A.2.5.2. Synthesis of 2-chloro-3-cyanobenzylamine

To a soln. of 3-(bromomethyl)-2-chlorobenzonitrile (0.87 mmol) in 9 mL DMF was added $NaN_3$ (1.3 mmol) and the resulting brown solution was stirred at RT for 20 min. The reaction mixture was diluted with EtOAc, washed twice with water and brine, dried over $MgSO_4$ and concentrated in vacuo. The crude azide was redissolved in 4.3 mL THF and 0.1 mL water. Triphenylphosphine (1.04 mmol) was added and the mixture was stirred at RT overnight. The reaction mixture was acidified with 0.1; N HCl soln. until pH 3 and it was extracted 3 times with $Et_2O$. The aq. phase was basified with 1M NaOH soln. and extracted 3 times with DCM. The comb. org. layers were dried over $MgSO_4$ and conc. in vacuo to give the desired product as yellowish oil.

LC-MS (3): $t_R$=0.31 min; [M+$CH_3$CN+H]+: 208.04.

A.2.6. Synthesis of 2,4-dichloro-6-methoxymethylbenzylamine

A.2.6.1. Synthesis of 2,4-dichloro-6-(methoxymethyl)benzonitrile

To a suspension of 2-(bromomethyl)-4,6-dichlorobenzonitrile (1.04 mmol) (A.2.2.1.) in 2.5 mL MeOH was added a solution of NaOMe (1.27 mmol, 0.5M in MeOH). The reaction mixture was heated to 50° C. for 1 h. The mixture was conc. in vacuo, redissolved in EtOAc and it was then washed twice with an aq. soln. of $KHSO_4$, twice with a sat. aq. $NaHCO_3$ soln. and once with brine. The org. layer was dried over $MgSO_4$ and conc. in vacuo to give the desired product as orange oil.

LC-MS (3): $t_R$=0.84 min; $^1$H NMR (($CD_3$)$_2$SO) δ: 7.97 (s, 1H), 7.67 (s, 1H), 4.59 (s, 2H), 3.37 (s, 3H).

A.2.6.2. Synthesis of 2,4-dichloro-6-methoxymethylbenzylamine

A soln. of $BH_3$ (3.5 mL, 1M in THF) was added to a solution of 2,4-dichloro-6-(methoxymethyl)benzonitrile (0.88 mmol) in 3 mL THF. The reaction mixture was heated to 60° C. for 2 h. At 0° C., 3.5 mL MeOH was dropwise added and the mixture was stirred until gaz evolution was finished. An aq. soln. of 10% NaOH was added still under cooling. The solvent was removed under vacuo, the residue was diluted with water and extracted 3 times with EtOAc. The comb. org. layers were dried over $MgSO_4$ and conc. in vacuo to give the desired product as orange oil.

LC-MS (3): $t_R$=0.45 min; [M+H]+: 220.26.

A.2.7. Synthesis of 2-trifluoromethyl-3-chlorobenzylamine

This compound was prepared using a method analogous to that of 2-chloro-3-cyanobenzylamine (A.2.5.), 1-chloro-3-methyl-2-(trifluoromethyl)benzene replacing 2-chloro-3-methylbenzonitrile.

LC-MS (3): $t_R$=0.44 min; [M+$CH_3$CN+H]+: 250.99.

A.2.8. Synthesis of 5,7-dichloro-2,3-dihydro-1H-inden-1-amine

A.2.8.1. Synthesis of 5,7-dichloro-2,3-dihydro-1H-inden-1-one O-methyl oxime To a soln. of 5,7-dichloro-1-indanone (0.34 mmol) in 2 mL MeOH was added O-methylhydroxylamine HCl (0.34 mmol). The reaction mixture was stirred at RT for 17 h and then heated to 50° C. for 24 h. The mixture was cooled to RT, diluted with water and extracted 3 times with EtOAc. The comb. org. layers were dried over $MgSO_4$ and conc. in vacuo to give the desired product as white solid.

LC-MS (3): $t_R$=0.99 min; [M+H]+: 229.96.

A.2.8.2. Synthesis of 5,7-dichloro-2,3-dihydro-1H-inden-1-amine

A soln. of $BH_3$ (0.6 mL, 1M in THF) was added to a soln. of 5,7-dichloro-2,3-dihydro-1H-inden-1-one O-methyl oxime (0.31 mmol) in 1 mL THF. The reaction mixture was heated to 60° C. for 3 days. An aq. 1M NaOH soln was added and heating to 60° C. was continued for another 24 h. The solvent was removed under vacuo, the residue was diluted with a sat. aq. $NaHCO_3$ soln. and extracted 3 times with EtOAc. The comb. org. layers were dried over $MgSO_4$ and conc. in vacuo to give the desired product as colorless oil.

LC-MS (3): $t_R$=0.46 min; [M+H]+: 202.03.

A.2.8.3. Chiral separation of 5,7-dichloro-2,3-dihydro-1H-inden-1-amine rac 5,7-Dichloro-2,3-dihydro-1H-inden-1-amine was separated into the respective enantiomers using prep. chiral HPLC (Daicel, ChiralPak AY-H, 5 μm, 20×250 mm; Hept/EtOH 90/10 0.1% DEA, flow 16 mL/min), detection: UV 210 nm Chiral analytic HPLC (Daicel, ChiralPak AY-H, 5 μm, 250×4.6 mm, Hept 0.05% DEA/EtOH 0.05% DEA 90/10, flow 0.8 mL/min), detection: UV 210 nm Enantiomer A: $t_R$=7.57 min;

Enantiomer B: $t_R$=8.59 min.

A.2.9. Synthesis of 2-bromo-4,6-dichlorobenzylamine

This compound was prepared using a method analogous to that of 2-chloro-3-cyanobenzylamine (A.2.5.), 1-bromo-2-(bromomethyl)-3,5-dichlorobenzene [J. Med. Chem. 1992, 35, 4221] replacing 3-(bromomethyl)-2-chlorobenzonitrile.

LC-MS (3): $t_R$=0.45 min; [M+$CH_3$CN+H]+: 294.83.

A.2.10. Synthesis of 2-((2-(aminomethyl)-3,5-dichlorobenzyl)oxy)ethanol

A.2.10.1. Synthesis of 2-((3,5-dichloro-2-cyanobenzyl)oxy)ethyl acetate

To a soln. of 2-(bromomethyl)-4,6-dichlorobenzonitrile (1.3 mmol) (A.2.2.1.) and 2-hydroxyethyl acetate (1.43 mmol) in 7 mL THF was added NaH (1.95 mmol, 60% suspension in oil). The reaction mixture was stirred at RT overnight and then poured into a 1M HCl soln. The mixture was extracted twice with EtOAc. The comb. org. layers were washed with brine, dried over MgSO$_4$ and conc. in vacuo. Purification with CC (0-25% EtOAc/Hept) gives the desired compound as orange oil.

LC-MS (3): $t_R$=0.82 min; [M+H]+: 287.89.

A.2.10.2 Synthesis of 2-((2-(aminomethyl)-3,5-dichlorobenzyl)oxy)ethanol

A soln. of BH$_3$ (1.46 mL, 1M in THF) was added to a soln. of 2-((3,5-dichloro-2-cyanobenzyl)oxy)ethyl acetate (0.36 mmol) in 1.5 mL MeOH. The reaction mixture was heated to 60° C. for 3 h. At 0° C., 1.5 mL MeOH was dropwise added and the mixture was stirred until gaz evolution was finished. An aq. soln. of 10% NaOH was added still under cooling. The solvent was removed under vacuo, the residue was diluted with water and extracted 3 times with EtOAc. The comb. org. layers were dried over MgSO$_4$ and conc. in vacuo to give the desired product as yellow solid.

LC-MS (3): $t_R$=0.43 min; [M+H]+: 250.20.

B. Preparation of Examples

B.1. Synthesis of compounds of formula (I) (general procedure)

A mixture of the respective carboxylic acid (II) (0.30 mmol), the respective amine (III) (0.36 mmol), HOBt (0.45 mmol), EDC.HCl (0.45 mmol) and DIPEA (0.90 mmol) in DMF (1.2 mL) was stirred at RT overnight. The mixture was filtrated and the filtrate was purified by purification methods listed beforehand to give the desired amides (I).

For the syntheses of N-(5,7-dichloro-2,3-dihydro-1H-inden-1-yl)-5,6-dihydrofuro[2,3-d]thiazole-6-carboxamide (example 11), N-(5,7-dichloro-2,3-dihydro-1H-inden-1-yl)-5,6-dihydro-4H-cyclopenta[d]thiazole-6-carboxamide (example 27) and N-(5,7-dichloro-2,3-dihydro-1H-inden-1-yl)-6,7-dihydro-5H-pyrano[2,3-d]thiazole-7-carboxamide (example 41) enantiomer B of 5,7-dichloro-2,3-dihydro-1H-inden-1-amine which was obtained by chiral separation as described in A.2.8.3. was used as amine of formula (III).

B.2. Synthesis of N-(2,4-dichloro-6-methylbenzyl)-2-(trifluoromethyl)-4,5,6,7-tetrahydrobenzo[d]thiazole-7-carboxamide (Example 58)

To a degassed solution of 2-bromo-N-(2,4-dichloro-6-methylbenzyl)-4,5,6,7-tetrahydrobenzo[d]thiazole-7-carboxamide (12 mg, 0.0276 mmol) (example 61) in DMF (0.5 mL) were sequentially added copper(I)iodide (26 mg, 0.1380 mmol), triphenylarsine (3.4 mg, 0.0111 mmol), tris(dibenzylideneacetone)dipalladium(0)chloroform adduct (1.4 mg, 0.0014 mmol) and methyl 2,2-difluoro-2-(fluorosulfonyl)acetate (26 mg, 0.1380 mmol). The resulting suspension was stirred at 100° C. for 4.5 h. The mixture was filtrated and the filtrate purified by prep. HPLC (F).

LC-MS (3): $t_R$=0.97 min; [M+H]+: 422.97.

EXAMPLE LIST

| Compound | Name | Purification method | LC-MS | $t_R$ [min] | [M + H]+ |
|---|---|---|---|---|---|
| Example 1 | N-(4-chlorobenzyl)-5,6-dihydrofuro[2,3-d]thiazole-6-carboxamide | A | 1 | 0.88 | 294.9 |
| Example 2 | N-(2,4-dichlorobenzyl)-5,6-dihydrofuro[2,3-d]thiazole-6-carboxamide | E | 3 | 0.70 | 329.0 |
| Example 3 | N-(2-chloro-4-fluorobenzyl)-5,6-dihydrofuro[2,3-d]thiazole-6-carboxamide | A | 1 | 0.89 | 312.9 |
| Example 4 | N-(3,4-dichlorobenzyl)-5,6-dihydrofuro[2,3-d]thiazole-6-carboxamide | A | 1 | 1.01 | 328.9 |
| Example 5 | N-(2-bromo-4,6-dichlorobenzyl)-5,6-dihydrofuro[2,3-d]thiazole-6-carboxamide | B | 1 | 1.12 | 406.5 |
| Example 6 | N-(2,4-dichloro-6-methylbenzyl)-5,6-dihydrofuro[2,3-d]thiazole-6-carboxamide | F | 3 | 0.75 | 343.0 |
| Example 7 | N-(2,4-dichlorophenethyl)-5,6-dihydrofuro[2,3-d]thiazole-6-carboxamide | A | 1 | 1.07 | 342.6 |
| Example 8 | N-(3-(2,4-dichlorophenyl)propyl)-5,6-dihydrofuro[2,3-d]thiazole-6-carboxamide | B | 1 | 1.18 | 356.9 |
| Example 9 | N-((S)-1-(2,4-dichlorophenyl)-2-hydroxyethyl)-5,6-dihydrofuro[2,3-d]thiazole-6-carboxamide (mixture of epimers) | A | 1 | 0.84 | 358.7 |

-continued

| Compound | Name | Purification method | LC-MS | $t_R$ [min] | $[M + H]^+$ |
|---|---|---|---|---|---|
| Example 10 | N-(2,4-dichloro-6-(hydroxymethyl)benzyl)-5,6-dihydrofuro[2,3-d]thiazole-6-carboxamide | A | 1 | 0.86 | 358.7 |
| Example 11 | N-(5,7-dichloro-2,3-dihydro-1H-inden-1-yl)-5,6-dihydrofuro[2,3-d]thiazole-6-carboxamide (mixture of epimers) | B | 1 | 1.09 | 354.9 |
| Example 12 | N-(2,4-dichloro-6-cyclopropylbenzyl)-5,6-dihydrofuro[2,3-d]thiazole-6-carboxamide | B | 1 | 1.23 | 368.9 |
| Example 13 | N-(2-chloro-3-(trifluoromethyl)benzyl)-5,6-dihydrofuro[2,3-d]thiazole-6-carboxamide | A | 1 | 1.06 | 362.9 |
| Example 14 | N-(3-chloro-2-(trifluoromethyl)benzyl)-5,6-dihydrofuro[2,3-d]thiazole-6-carboxamide | A | 1 | 1.05 | 362.9 |
| Example 15 | N-(2,4-dichloro-6-((2-hydroxyethoxy)methyl)benzyl)-5,6-dihydrofuro[2,3-d]thiazole-6-carboxamide | A | 1 | 0.90 | 402.9 |
| Example 16 | N-(4-phenoxybenzyl)-5,6-dihydrofuro[2,3-d]thiazole-6-carboxamide | B | 1 | 1.11 | 353.0 |
| Example 17 | N-(2,4-dichlorobenzyl)-5,6-dihydro-4H-cyclopenta[d]thiazole-6-carboxamide | F | 3 | 0.70 | 327.0 |
| Example 18 | N-(2-chloro-4-fluorobenzyl)-5,6-dihydro-4H-cyclopenta[d]thiazole-6-carboxamide | A | 1 | 0.91 | 311.0 |
| Example 19 | N-(2-bromo-4,6-dichlorobenzyl)-5,6-dihydro-4H-cyclopenta[d]thiazole-6-carboxamide | B | 1 | 1.14 | 404.8 |
| Example 20 | N-(2,4-dichloro-6-methylbenzyl)-5,6-dihydro-4H-cyclopenta[d]thiazole-6-carboxamide | F | 3 | 0.74 | 341.0 |
| Example 21 | N-(2,4-dichlorophenethyl)-5,6-dihydro-4H-cyclopenta[d]thiazole-6-carboxamide | B | 1 | 1.08 | 341.1 |
| Example 22 | N-(2-chloro-3-cyanobenzyl)-5,6-dihydro-4H-cyclopenta[d]thiazole-6-carboxamide | A | 1 | 0.78 | 318.1 |
| Example 23 | N-(3-(2,4-dichlorophenyl)propyl)-5,6-dihydro-4H-cyclopenta[d]thiazole-6-carboxamide | B | 1 | 1.19 | 354.9 |
| Example 24 | N-((S)-1-(2,4-dichlorophenyl)-2-hydroxyethyl)-5,6-dihydro-4H-cyclopenta[d]thiazole-6-carboxamide (mixture of epimers) | A | 1 | 0.85 | 357.1 |
| Example 25 | N-(2,4-dichloro-6-(hydroxymethyl)benzyl)-5,6-dihydro-4H-cyclopenta[d]thiazole-6-carboxamide | A | 1 | 0.88 | 357.1 |
| Example 26 | N-(2,4-dichloro-6-methoxybenzyl)-5,6-dihydro-4H-cyclopenta[d]thiazole-6-carboxamide | A | 1 | 1.07 | 357.1 |
| Example 27 | N-(5,7-dichloro-2,3-dihydro-1H-inden-1-yl)-5,6-dihydro-4H-cyclopenta[d]thiazole-6-carboxamide (mixture of epimers) | B | 1 | 1.11 | 353.1 |
| Example 28 | N-(2-chloro-3-(trifluoromethyl)benzyl)-5,6-dihydro-4H-cyclopenta[d]thiazole-6-carboxamide | F | 3 | 0.71 | 361.0 |
| Example 29 | N-(3-fluoro-4-(trifluoromethoxy)benzyl)-5,6-dihydro-4H-cyclopenta[d]thiazole-6-carboxamide | A | 1 | 1.07 | 361.1 |
| Example 30 | N-(4-chlorobenzyl)-N-methyl-6,7-dihydro-5H-pyrano[2,3-d]thiazole-7-carboxamide | A | 1 | 0.99 | 323.0 |

-continued

| Compound | Name | Purification method | LC-MS | $t_R$ [min] | $[M + H]^+$ |
|---|---|---|---|---|---|
| Example 31 | N-(2,4-dichlorobenzyl)-6,7-dihydro-5H-pyrano[2,3-d]thiazole-7-carboxamide | E | 3 | 0.70 | 343.0 |
| Example 32 | N-(2-chloro-4-fluorobenzyl)-6,7-dihydro-5H-pyrano[2,3-d]thiazole-7-carboxamide | A | 1 | 0.89 | 326.7 |
| Example 33 | N-(2,3-dichlorobenzyl)-6,7-dihydro-5H-pyrano[2,3-d]thiazole-7-carboxamide | A | 1 | 0.98 | 342.7 |
| Example 34 | N-(2,4-dichloro-6-methylbenzyl)-6,7-dihydro-5H-pyrano[2,3-d]thiazole-7-carboxamide | F | 3 | 0.74 | 357.0 |
| Example 35 | N-(2,4-dichlorophenethyl)-6,7-dihydro-5H-pyrano[2,3-d]thiazole-7-carboxamide | B | 1 | 1.07 | 356.9 |
| Example 36 | N-(2-chloro-3-cyanobenzyl)-6,7-dihydro-5H-pyrano[2,3-d]thiazole-7-carboxamide | A | 1 | 0.77 | 333.9 |
| Example 37 | N-(4-(trifluoromethyl)benzyl)-6,7-dihydro-5H-pyrano[2,3-d]thiazole-7-carboxamide | A | 1 | 0.98 | 342.8 |
| Example 38 | N-(3-(2,4-dichlorophenyl)propyl)-6,7-dihydro-5H-pyrano[2,3-d]thiazole-7-carboxamide | B | 1 | 1.17 | 370.9 |
| Example 39 | N-((S)-1-(2,4-dichlorophenyl)-2-hydroxyethyl)-6,7-dihydro-5H-pyrano[2,3-d]thiazole-7-carboxamide (mixture of epimers) | A | 1 | 0.85 | 372.9 |
| Example 40 | N-(2,4-dichloro-6-(hydroxymethyl)benzyl)-6,7-dihydro-5H-pyrano[2,3-d]thiazole-7-carboxamide | A | 1 | 0.86 | 372.9 |
| Example 41 | N-(5,7-dichloro-2,3-dihydro-1H-inden-1-yl)-6,7-dihydro-5H-pyrano[2,3-d]thiazole-7-carboxamide (mixture of epimers) | B | 1 | 1.10 | 368.9 |
| Example 42 | N-(2-chloro-3-(trifluoromethyl)benzyl)-6,7-dihydro-5H-pyrano[2,3-d]thiazole-7-carboxamide | A | 1 | 1.05 | 376.9 |
| Example 43 | N-(2,4-dichloro-6-(2-hydroxyethoxy)benzyl)-6,7-dihydro-5H-pyrano[2,3-d]thiazole-7-carboxamide | A | 1 | 0.94 | 402.9 |
| Example 44 | N-(3-fluoro-4-(trifluoromethoxy)benzyl)-6,7-dihydro-5H-pyrano[2,3-d]thiazole-7-carboxamide | A | 1 | 1.06 | 376.9 |
| Example 45 | N-(4-phenoxybenzyl)-6,7-dihydro-5H-pyrano[2,3-d]thiazole-7-carboxamide | B | 1 | 1.11 | 367.0 |
| Example 46 | N-(4-chlorobenzyl)-4,5,6,7-tetrahydrobenzo[d]thiazole-7-carboxamide | C | 2 | 0.94 | 307.0 |
| Example 47 | N-(4-chlorobenzyl)-N-methyl-4,5,6,7-tetrahydrobenzo[d]thiazole-7-carboxamide | C | 2 | 1.07 | 321.0 |
| Example 48 | N-(3-chloro-2-methylbenzyl)-4,5,6,7-tetrahydrobenzo[d]thiazole-7-carboxamide | C | 2 | 1.03 | 321.0 |
| Example 49 | 2-amino-N-(2,4-dichlorobenzyl)-4,5,6,7-tetrahydrobenzo[d]thiazole-7-carboxamide | H | 3 | 0.58 | 356.0 |
| Example 50 | N-(2,4-dichlorobenzyl)-2-methyl-4,5,6,7-tetrahydrobenzo[d]thiazole-7-carboxamide | F | 3 | 0.66 | 355.0 |
| Example 51 | 2-bromo-N-(2,4-dichlorobenzyl)-4,5,6,7-tetrahydrobenzo[d]thiazole-7-carboxamide | F | 3 | 0.86 | 418.9 |
| Example 52 | N-(2,4-dichlorobenzyl)-4,5,6,7-tetrahydrobenzo[d]thiazole-7-carboxamide | F, H | 3 | 0.69 | 340.9 |

-continued

| Compound | Name | Purification method | LC-MS | $t_R$ [min] | $[M + H]^+$ |
|---|---|---|---|---|---|
| Example 53 | N-(2-chloro-4-fluorobenzyl)-4,5,6,7-tetrahydrobenzo[d]thiazole-7-carboxamide | C | 2 | 0.97 | 325.0 |
| Example 54 | N-(2,3-dichlorobenzyl)-4,5,6,7-tetrahydrobenzo[d]thiazole-7-carboxamide | C | 2 | 1.04 | 341.0 |
| Example 55 | N-(2,3-dihydro-1H-inden-1-yl)-4,5,6,7-tetrahydrobenzo[d]thiazole-7-carboxamide (mixture of 4 stereoisomers) | C | 2 | 0.93 | 299.1 |
| Example 56 | N-((R)-1-(2,4-dichlorophenyl)ethyl)-4,5,6,7-tetrahydrobenzo[d]thiazole-7-carboxamide (mixture of epimers) | D | 2 | 1.15 | 355.0 |
| Example 57 | N-(2,4-dichloro-6-methylbenzyl)-2-phenyl-4,5,6,7-tetrahydrobenzo[d]thiazole-7-carboxamide | F, H | 3 | 0.95 | 430.9 |
| Example 58 | N-(2,4-dichloro-6-methylbenzyl)-2-(trifluoromethyl)-4,5,6,7-tetrahydrobenzo[d]thiazole-7-carboxamide | F | 3 | 0.96 | 423.0 |
| Example 59 | 2-amino-N-(2,4-dichloro-6-methylbenzyl)-4,5,6,7-tetrahydrobenzo[d]thiazole-7-carboxamide | L | 3 | 0.62 | 369.8 |
| Example 60 | N-(2,4-dichloro-6-methylbenzyl)-2-methyl-4,5,6,7-tetrahydrobenzo[d]thiazole-7-carboxamide | M | 3 | 0.71 | 368.9 |
| Example 61 | 2-bromo-N-(2,4-dichloro-6-methyl benzyl)-4,5,6,7-tetrahydrobenzo[d]thiazole-7-carboxamide | F | 3 | 0.91 | 432.9 |
| Example 62 | N-(2,4-dichloro-6-methylbenzyl)-4,5,6,7-tetrahydrobenzo[d]thiazole-7-carboxamide | F | 3 | 0.75 | 355.2 |
| Example 63 | N-(2,4-dichlorophenethyl)-4,5,6,7-tetrahydrobenzo[d]thiazole-7-carboxamide | D | 2 | 1.12 | 355.0 |
| Example 64 | N-((S)-1-(2,4-dichlorophenyl)-2-hydroxyethyl)-4,5,6,7-tetrahydrobenzo[d]thiazole-7-carboxamide (mixture of epimers) | F, K, N | 3 | 0.59 | 370.8 |
| Example 65 | N-(2,4-dichloro-6-(hydroxymethyl)benzyl)-4,5,6,7-tetrahydrobenzo[d]thiazole-7-carboxamide | C | 2 | 0.92 | 371.0 |
| Example 66 | 2-bromo-N-(2-chloro-3-(trifluoromethyl)benzyl)-4,5,6,7-tetrahydrobenzo[d]thiazole-7-carboxamide | F | 3 | 0.86 | 452.9 |
| Example 67 | N-(2-chloro-3-(trifluoromethyl)benzyl)-4,5,6,7-tetrahydrobenzo[d]thiazole-7-carboxamide | D | 2 | 1.10 | 374.8 |
| Example 68 | N-(2,4-dichloro-6-(methoxymethyl)benzyl)-4,5,6,7-tetrahydrobenzo[d]thiazole-7-carboxamide | D | 2 | 1.13 | 385.0 |
| Example 69 | N-(3-fluoro-4-(trifluoromethoxy)benzyl)-4,5,6,7-tetrahydrobenzo[d]thiazole-7-carboxamide | D | 2 | 1.11 | 374.8 |
| Example 70 | N-(4-phenoxybenzyl)-4,5,6,7-tetrahydrobenzo[d]thiazole-7-carboxamide | D | 2 | 1.15 | 365.1 |
| Example 71 | 2-amino-N-(2,4-dichlorobenzyl)-5,6,7,8-tetrahydro-4H-cyclohepta[d]thiazole-8-carboxamide | H | 3 | 0.62 | 369.8 |
| Example 72 | N-(2,4-dichlorobenzyl)-5,6,7,8-tetrahydro-4H-cyclohepta[d]thiazole-8-carboxamide | F | 3 | 0.71 | 354.9 |

| Compound | Name | Purification method | LC-MS | $t_R$ [min] | $[M + H]^+$ |
|---|---|---|---|---|---|
| Example 73 | 2-amino-N-(2,4-dichloro-6-methylbenzyl)-5,6,7,8-tetrahydro-4H-cyclohepta[d]thiazole-8-carboxamide | H | 3 | 0.66 | 384.0 |
| Example 74 | N-(2,4-dichloro-6-methylbenzyl)-5,6,7,8-tetrahydro-4H-cyclohepta[d]thiazole-8-carboxamide | F | 3 | 0.75 | 368.9 |
| Example 75 | N-((S)-1-(2,4-dichlorophenyl)-2-hydroxyethyl)-5,6,7,8-tetrahydro-4H-cyclohepta[d]thiazole-8-carboxamide (epimer A) | F | 3 | 0.61 | 384.9 |
| Example 76 | N-((S)-1-(2,4-dichlorophenyl)-2-hydroxyethyl)-5,6,7,8-tetrahydro-4H-cyclohepta[d]thiazole-8-carboxamide (epimer B) | F | 3 | 0.60 | 384.9 |

II. Biological Assays

A. In Vitro Assay

The $P2X_7$ receptor antagonistic activity of the compounds of formula (I) is determined in accordance with the following experimental method.

B. Experimental Method

Cell Line Generation and YO-PRO Assay

Cell line generation was performed in general according to established molecular cloning protocols. Specifically, RNA was extracted from human whole blood using the Qiagen RNeasy kit (Qiagen, CH) according to the manufacturer's instructions. Subsequently cDNA was made (Superscript II, Invitrogen AG, CH) and the human P2X7 gene (genbank ref. BC011913) was amplified with the following primers: ATCGCGGCCGCTCAGTAAGGACTCTTGAAGCCACT and CGCCGCTAGCACCACCATGCCGGCCT-GCTGCAGCTGCA. The amplified sequence was subsequently ligated into a pcDNA3.1 (+) NotI, NheI digested plasmid. Human embryonic kidney (HEK) cells (ATCC CRL-1573, Manassas, Va., USA) were transfected with the pcDNA3.1 (+).hP2X7 plasmid using lipofectamine 2000 (Invitrogen AG, CH) according to the manufacturer's instructions. Following a 24 h exposure to DNA, cells were trypsinized and re-seeded at low density in the presence of 250 µg Geneticin. Geneticin resistant cells were then selected during two consecutive rounds of cloning by serial limiting dilution with visual inspection. Individual clones were screened for P2X7 expression by applying ATP and recording the resultant uptake of YO-PRO1. Specific cell clones were chosen based on RNA and protein expression. HEK cells stably expressing P2X7 were used to screen drugs using the YO-PRO1 assay. Cells were grown to confluency in adherent culture at 37° C. in a humidified 5% $CO_2$ incubator (split 1/5 every 3-4 days with DMEM, 10% FCS, 1% Penicillin/Streptomycin, 250 µg/ml Geneticin). Adherent cells were detached by incubation with Trypsine (1 ml per 165 $cm^2$ dish) for 2 minutes, then washed off with 10 ml PBS (without $Mg^{2+}$ and $Ca^{2+}$), and resuspended in DMEM, 10% FCS, 1% Penicillin/Streptomycin, no Geneticin. 10,000 cells per well (48 hours before the assay) or 25,000 cells per well (Vi-cell XR (Beckman Coulter) (24 hours before the assay) in 50 µl full medium were seeded on 384-well black-wall, clear bottom plates, that were coated before with 10 µl per well Poly-L-Lysine, incubated for 30-60 minutes at 37° C. and washed once with PBS. Medium was removed from cells and 50 µl of assay buffer containing 0.5 µM YO-PRO-1 was added into the wells. Solutions of antagonist compounds were prepared by serial dilutions of a 10 mM DMSO solution of the antagonist into PBS using a BioMek (Beckman Coulter). Each concentration was performed in duplicate. For $IC_{50}$ measurements 10 concentration points were measured (10 µM being the highest concentration followed by 9 serial dilution steps 1/3). The cells were incubated with the antagonists of the present invention together with ATP at a final concentration of 250 µM for 90 minutes. During this time period, four time points were taken. Each time point comprised the average of several measurements made within a few seconds. Fluorescence was measured in the FLIPR tetra (Molecular Devices) using the filters appropriate for YO-PRO-1 fluorescence (excitation 485/20, emission 530/25). The FLIPR tetra was equipped with Molecular Devices Screen Works system control software to define and run experimental protocols. For antagonist activity measurements, the maximal intensity was expressed as a percentage of that induced by the $EC_{50}$ value for agonist activation (0.25 mM ATP for HEK-293 cells expressing human recombinant P2X7 receptor). For IC50 measurements the maximum intensity is plotted against the concentration of compound to determine IC50 values.

Antagonistic activities with respect to the $P2X_7$ receptor ($IC_{50}$ values) of exemplified compounds are displayed in Table 1.

TABLE 1

| Compound | Name | $IC_{50}$ [nM] |
|---|---|---|
| Example 1 | N-(4-chlorobenzyl)-5,6-dihydrofuro[2,3-d]thiazole-6-carboxamide | 4630 |
| Example 2 | N-(2,4-dichlorobenzyl)-5,6-dihydrofuro[2,3-d]thiazole-6-carboxamide | 103 |

TABLE 1-continued

| Compound | Name | IC$_{50}$ [nM] |
|---|---|---|
| Example 3 | N-(2-chloro-4-fluorobenzyl)-5,6-dihydrofuro[2,3-d]thiazole-6-carboxamide | 183 |
| Example 4 | N-(3,4-dichlorobenzyl)-5,6-dihydrofuro[2,3-d]thiazole-6-carboxamide | 2945 |
| Example 5 | N-(2-bromo-4,6-dichlorobenzyl)-5,6-dihydrofuro[2,3-d]thiazole-6-carboxamide | 7.3 |
| Example 6 | N-(2,4-dichloro-6-methylbenzyl)-5,6-dihydrofuro[2,3-d]thiazole-6-carboxamide | 4.3 |
| Example 7 | N-(2,4-dichlorophenethyl)-5,6-dihydrofuro[2,3-d]thiazole-6-carboxamide | 428 |
| Example 8 | N-(3-(2,4-dichlorophenyl)propyl)-5,6-dihydrofuro[2,3-d]thiazole-6-carboxamide | 359 |
| Example 9 | N-((S)-1-(2,4-dichlorophenyl)-2-hydroxyethyl)-5,6-dihydrofuro[2,3-d]thiazole-6-carboxamide (mixture of epimers) | 316 |
| Example 10 | N-(2,4-dichloro-6-(hydroxymethyl)benzyl)-5,6-dihydrofuro[2,3-d]thiazole-6-carboxamide | 12 |
| Example 11 | N-(5,7-dichloro-2,3-dihydro-1H-inden-1-yl)-5,6-dihydrofuro[2,3-d]thiazole-6-carboxamide (mixture of epimers) | 4.1 |
| Example 12 | N-(2,4-dichloro-6-cyclopropylbenzyl)-5,6-dihydrofuro[2,3-d]thiazole-6-carboxamide | 13 |
| Example 13 | N-(2-chloro-3-(trifluoromethyl) benzyl)-5,6-dihydrofuro[2,3-d]thiazole-6-carboxamide | 17 |
| Example 14 | N-(3-chloro-2-(trifluoromethyl) benzyl)-5,6-dihydrofuro[2,3-d]thiazole-6-carboxamide | 38 |
| Example 15 | N-(2,4-dichloro-6-((2-hydroxyethoxy)methyl)benzyl)-5,6-dihydrofuro[2,3-d]thiazole-6-carboxamide | 15 |
| Example 16 | N-(4-phenoxybenzyl)-5,6-dihydrofuro[2,3-d]thiazole-6-carboxamide | 1572 |
| Example 17 | N-(2,4-dichlorobenzyl)-5,6-dihydro-4H-cyclopenta[d]thiazole-6-carboxamide | 11 |
| Example 18 | N-(2-chloro-4-fluorobenzyl)-5,6-dihydro-4H-cyclopenta[d]thiazole-6-carboxamide | 66 |
| Example 19 | N-(2-bromo-4,6-dichlorobenzyl)-5,6-dihydro-4H-cyclopenta[d]thiazole-6-carboxamide | 4.5 |
| Example 20 | N-(2,4-dichloro-6-methylbenzyl)-5,6-dihydro-4H-cyclopenta[d]thiazole-6-carboxamide | 1.5 |
| Example 21 | N-(2,4-dichlorophenethyl)-5,6-dihydro-4H-cyclopenta[d]thiazole-6-carboxamide | 122 |
| Example 22 | N-(2-chloro-3-cyanobenzyl)-5,6-dihydro-4H-cyclopenta[d]thiazole-6-carboxamide | 85 |
| Example 23 | N-(3-(2,4-dichlorophenyl)propyl)-5,6-dihydro-4H-cyclopenta[d]thiazole-6-carboxamide | 158 |
| Example 24 | N-((S)-1-(2,4-dichlorophenyl)-2-hydroxyethyl)-5,6-dihydro-4H-cyclopenta[d]thiazole-6-carboxamide (mixture of epimers) | 92 |
| Example 25 | N-(2,4-dichloro-6-(hydroxymethyl)benzyl)-5,6-dihydro-4H-cyclopenta[d]thiazole-6-carboxamide | 6.3 |
| Example 26 | N-(2,4-dichloro-6-methoxybenzyl)-5,6-dihydro-4H-cyclopenta[d]thiazole-6-carboxamide | 49 |
| Example 27 | N-(5,7-dichloro-2,3-dihydro-1H-inden-1-yl)-5,6-dihydro-4H-cyclopenta[d]thiazole-6-carboxamide (mixture of epimers) | 3.0 |
| Example 28 | N-(2-chloro-3-(trifluoromethyl)benzyl)-5,6-dihydro-4H-cyclopenta[d]thiazole-6-carboxamide | 4.7 |
| Example 29 | N-(3-fluoro-4-(trifluoromethoxy)benzyl)-5,6-dihydro-4H-cyclopenta[d]thiazole-6-carboxamide | 2000 |
| Example 30 | N-(4-chlorobenzyl)-N-methyl-6,7-dihydro-5H-pyrano[2,3-d]thiazole-7-carboxamide | 6105 |
| Example 31 | N-(2,4-dichlorobenzyl)-6,7-dihydro-5H-pyrano[2,3-d]thiazole-7-carboxamide | 22 |
| Example 32 | N-(2-chloro-4-fluorobenzyl)-6,7-dihydro-5H-pyrano[2,3-d]thiazole-7-carboxamide | 76 |
| Example 33 | N-(2,3-dichlorobenzyl)-6,7-dihydro-5H-pyrano[2,3-d]thiazole-7-carboxamide | 44 |
| Example 34 | N-(2,4-dichloro-6-methylbenzyl)-6,7-dihydro-5H-pyrano[2,3-d]thiazole-7-carboxamide | 1.6 |
| Example 35 | N-(2,4-dichlorophenethyl)-6,7-dihydro-5H-pyrano[2,3-d]thiazole-7-carboxamide | 111 |
| Example 36 | N-(2-chloro-3-cyanobenzyl)-6,7-dihydro-5H-pyrano[2,3-d]thiazole-7-carboxamide | 71 |
| Example 37 | N-(4-(trifluoromethyl)benzyl)-6,7-dihydro-5H-pyrano[2,3-d]thiazole-7-carboxamide | 1605 |
| Example 38 | N-(3-(2,4-dichlorophenyl)propyl)-6,7-dihydro-5H-pyrano[2,3-d]thiazole-7-carboxamide | 500 |
| Example 39 | N-((S)-1-(2,4-dichlorophenyl)-2-hydroxyethyl)-6,7-dihydro-5H-pyrano[2,3-d]thiazole-7-carboxamide (mixture of epimers) | 139 |
| Example 40 | N-(2,4-dichloro-6-(hydroxymethyl)benzyl)-6,7-dihydro-5H-pyrano[2,3-d]thiazole-7-carboxamide | 5.2 |

TABLE 1-continued

| Compound | Name | IC$_{50}$ [nM] |
|---|---|---|
| Example 41 | N-(5,7-dichloro-2,3-dihydro-1H-inden-1-yl)-6,7-dihydro-5H-pyrano[2,3-d]thiazole-7-carboxamide (mixture of epimers) | 1.8 |
| Example 42 | N-(2-chloro-3-(trifluoromethyl)benzyl)-6,7-dihydro-5H-pyrano[2,3-d]thiazole-7-carboxamide | 6.9 |
| Example 43 | N-(2,4-dichloro-6-(2-hydroxyethoxy)benzyl)-6,7-dihydro-5H-pyrano[2,3-d]thiazole-7-carboxamide | 53 |
| Example 44 | N-(3-fluoro-4-(trifluoromethoxy)benzyl)-6,7-dihydro-5H-pyrano[2,3-d]thiazole-7-carboxamide | 3795 |
| Example 45 | N-(4-phenoxybenzyl)-6,7-dihydro-5H-pyrano[2,3-d]thiazole-7-carboxamide | 733 |
| Example 46 | N-(4-chlorobenzyl)-4,5,6,7-tetrahydrobenzo[d]thiazole-7-carboxamide | 269 |
| Example 47 | N-(4-chlorobenzyl)-N-methyl-4,5,6,7-tetrahydrobenzo[d]thiazole-7-carboxamide | 736 |
| Example 48 | N-(3-chloro-2-methylbenzyl)-4,5,6,7-tetrahydrobenzo[d]thiazole-7-carboxamide | 7.5 |
| Example 49 | 2-amino-N-(2,4-dichlorobenzyl)-4,5,6,7-tetrahydrobenzo[d]thiazole-7-carboxamide | 25 |
| Example 50 | N-(2,4-dichlorobenzyl)-2-methyl-4,5,6,7-tetrahydrobenzo[d]thiazole-7-carboxamide | 20 |
| Example 51 | 2-bromo-N-(2,4-dichlorobenzyl)-4,5,6,7-tetrahydrobenzo[d]thiazole-7-carboxamide | 23 |
| Example 52 | N-(2,4-dichlorobenzyl)-4,5,6,7-tetrahydrobenzo[d]thiazole-7-carboxamide | 7.5 |
| Example 53 | N-(2-chloro-4-fluorobenzyl)-4,5,6,7-tetrahydrobenzo[d]thiazole-7-carboxamide | 13 |
| Example 54 | N-(2,3-dichlorobenzyl)-4,5,6,7-tetrahydrobenzo[d]thiazole-7-carboxamide | 8.9 |
| Example 55 | N-(2,3-dihydro-1H-inden-1-yl)-4,5,6,7-tetrahydrobenzo[d]thiazole-7-carboxamide (mixture of 4 stereoisomers) | 143 |
| Example 56 | N-((R)-1-(2,4-dichlorophenyl)ethyl)-4,5,6,7-tetrahydrobenzo[d]thiazole-7-carboxamide (mixture of epimers) | 6.7 |
| Example 57 | N-(2,4-dichloro-6-methylbenzyl)-2-phenyl-4,5,6,7-tetrahydrobenzo[d]thiazole-7-carboxamide | 1040 |
| Example 58 | N-(2,4-dichloro-6-methylbenzyl)-2-(trifluoromethyl)-4,5,6,7-tetrahydrobenzo[d]thiazole-7-carboxamide | 31 |
| Example 59 | 2-amino-N-(2,4-dichloro-6-methylbenzyl)-4,5,6,7-tetrahydrobenzo[d]thiazole-7-carboxamide | 4.9 |
| Example 60 | N-(2,4-dichloro-6-methylbenzyl)-2-methyl-4,5,6,7-tetrahydrobenzo[d]thiazole-7-carboxamide | 4.3 |
| Example 61 | 2-bromo-N-(2,4-dichloro-6-methylbenzyl)-4,5,6,7-tetrahydrobenzo[d]thiazole-7-carboxamide | 12 |
| Example 62 | N-(2,4-dichloro-6-methylbenzyl)-4,5,6,7-tetrahydrobenzo[d]thiazole-7-carboxamide | 1.9 |
| Example 63 | N-(2,4-dichlorophenethyl)-4,5,6,7-tetrahydrobenzo[d]thiazole-7-carboxamide | 20 |
| Example 64 | N-((S)-1-(2,4-dichlorophenyl)-2-hydroxyethyl)-4,5,6,7-tetrahydrobenzo[d]thiazole-7-carboxamide (mixture of epimers) | 96 |
| Example 65 | N-(2,4-dichloro-6-(hydroxymethyl)benzyl)-4,5,6,7-tetrahydrobenzo[d]thiazole-7-carboxamide | 2.7 |
| Example 66 | 2-bromo-N-(2-chloro-3-(trifluoromethyl)benzyl)-4,5,6,7-tetrahydrobenzo[d]thiazole-7-carboxamide | 13 |
| Example 67 | N-(2-chloro-3-(trifluoromethyl) benzyl)-4,5,6,7-tetrahydrobenzo[d]thiazole-7-carboxamide | 2.6 |
| Example 68 | N-(2,4-dichloro-6-(methoxymethyl)benzyl)-4,5,6,7-tetrahydrobenzo[d]thiazole-7-carboxamide | 4.3 |
| Example 69 | N-(3-fluoro-4-(trifluoromethoxy)benzyl)-4,5,6,7-tetrahydrobenzo[d]thiazole-7-carboxamide | 457 |
| Example 70 | N-(4-phenoxybenzyl)-4,5,6,7-tetrahydrobenzo[d]thiazole-7-carboxamide | 168 |
| Example 71 | 2-amino-N-(2,4-dichlorobenzyl)-5,6,7,8-tetrahydro-4H-cyclohepta[d]thiazole-8-carboxamide | 94 |
| Example 72 | N-(2,4-dichlorobenzyl)-5,6,7,8-tetrahydro-4H-cyclohepta[d]thiazole-8-carboxamide | 36 |
| Example 73 | 2-amino-N-(2,4-dichloro-6-methylbenzyl)-5,6,7,8-tetrahydro-4H-cyclohepta[d]thiazole-8-carboxamide | 13 |
| Example 74 | N-(2,4-dichloro-6-methylbenzyl)-5,6,7,8-tetrahydro-4H-cyclohepta[d]thiazole-8-carboxamide | 3.9 |
| Example 75 | N-((S)-1-(2,4-dichlorophenyl)-2-hydroxyethyl)-5,6,7,8-tetrahydro-4H-cyclohepta[d]thiazole-8-carboxamide (epimer A) | 82 |
| Example 76 | N-((S)-1-(2,4-dichlorophenyl)-2-hydroxyethyl)-5,6,7,8-tetrahydro-4H-cyclohepta[d]thiazole-8-carboxamide (epimer B) | 114 |

The invention claimed is:

1. A compound of the formula (I),

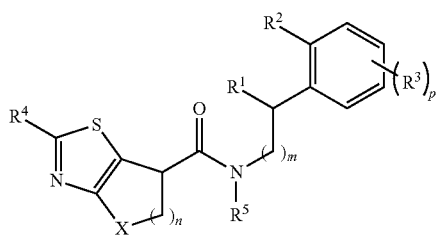

(I)

wherein n represents 1, 2 or 3;

m represents 0, 1 or 2;

p represents 0, 1 or 2;

X represents —O— or —CH$_2$—;

$R^1$ represents hydrogen, (C$_1$-C$_2$)alkyl or hydroxy-(C$_1$-C$_2$)alkyl and $R^2$ represents hydrogen or halogen; or $R^1$ and $R^2$ together represent a —CH$_2$CH$_2$— or a —CH$_2$CH$_2$CH$_2$— group;

each $R^3$ independently represents (C$_1$-C$_4$)alkyl, (C$_3$-C$_6$)cycloalkyl, (C$_1$-C$_4$)alkoxy, hydroxy-(C$_1$-C$_3$)alkyl, hydroxy-(C$_2$-C$_3$)alkoxy, hydroxy-(C$_2$-C$_3$)alkoxy-(C$_1$-C$_2$)alkyl, (C$_1$-C$_2$)alkoxy-(C$_1$-C$_2$)alkyl, (C$_1$-C$_3$)fluoroalkyl, (C$_1$-C$_3$)fluoroalkoxy, cyano, halogen or phenoxy;

$R^4$ represents hydrogen, (C$_1$-C$_4$)alkyl, (C$_1$-C$_3$)fluoroalkyl, amino, halogen or phenyl; and $R^5$ represents hydrogen or methyl;

or a salt of such a compound.

2. The compound of formula (I) according to claim 1, that is a compound of formula (Ixo),

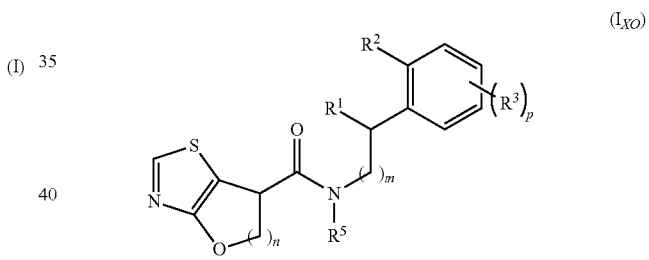

(I$_{XO}$)

wherein n represents 1, 2 or 3;

m represents 0, 1 or 2;

p represents 1 or 2;

$R^1$ represents hydrogen, (C$_1$-C$_2$)alkyl or hydroxy-(C$_1$-C$_2$)alkyl and $R^2$ represents hydrogen or halogen; or $R^1$ and $R^2$ together represent a —CH$_2$CH$_2$— or a —CH$_2$CH$_2$CH$_2$— group;

each $R^3$ independently represents (C$_1$-C$_4$)alkyl, (C$_3$-C$_6$)cycloalkyl, (C$_1$-C$_4$)alkoxy, hydroxy-(C$_1$-C$_3$)alkyl, hydroxy-(C$_2$-C$_3$)alkoxy, hydroxy-(C$_2$-C$_3$)alkoxy-(C$_1$-C$_2$)alkyl, (C$_1$-C$_2$)alkoxy-(C$_1$-C$_2$)alkyl, (C$_1$-C$_3$)fluoroalkyl, (C$_1$-C$_3$)fluoroalkoxy, cyano, halogen or phenoxy; and $R^5$ represents hydrogen or methyl;

or a salt of such a compound.

3. The compound of formula (I) according to claim 1, wherein m represents 0;

or a salt of such a compound.

4. The compound of formula (I) according to claim 1, wherein p represents 2;

or a salt of such a compound.

5. The compound of formula (I) according to claim 1, wherein
$R^1$ represents hydrogen and $R^2$ represents chloro;
or a salt of such a compound.

6. The compound of formula (I) according to claim 1, wherein
$R^1$ and $R^2$ together represent a —CH$_2$CH$_2$— group;
or a salt of such a compound.

7. The compound of formula (I) according to claim 1, wherein
a first $R^3$ group is attached in para-position relative to the $R^1$-bearing carbon atom and represents chloro; and
a second $R^3$ group is absent, or is attached in ortho-position relative to the $R^1$-bearing carbon atom and represents methyl, cyclopropyl, methoxy, hydroxy-methyl, 2-hydroxy-ethoxy, (2-hydroxy-ethoxy)-methyl, methoxy-methyl, chloro or bromo;
or a salt of such a compound.

8. The compound of formula (I) according to claim 1, wherein
$R^4$ represents hydrogen;
or a salt of such a compound.

9. The compound of formula (I) according to claim 1, wherein
$R^5$ represents hydrogen;
or a salt of such a compound.

10. The compound of formula (I) according to claim 1, selected from the group consisting of:
N-(4-chlorobenzyl)-5,6-dihydrofuro[2,3-d]thiazole-6-carboxamide;
N-(2,4-dichlorobenzyl)-5,6-dihydrofuro[2,3-d]thiazole-6-carboxamide;
N-(2-chloro-4-fluorobenzyl)-5,6-dihydrofuro[2,3-d]thiazole-6-carboxamide;
N-(3,4-dichlorobenzyl)-5,6-dihydrofuro[2,3-d]thiazole-6-carboxamide;
N-(2-bromo-4,6-dichlorobenzyl)-5,6-dihydrofuro[2,3-d]thiazole-6-carboxamide;
N-(2,4-dichloro-6-methylbenzyl)-5,6-dihydrofuro[2,3-d]thiazole-6-carboxamide;
N-(2,4-dichlorophenethyl)-5,6-dihydrofuro[2,3-d]thiazole-6-carboxamide;
N-(3-(2,4-dichlorophenyl)propyl)-5,6-dihydrofuro[2,3-d]thiazole-6-carboxamide;
N-(1-(2,4-dichlorophenyl)-2-hydroxyethyl)-5,6-dihydrofuro[2,3-d]thiazole-6-carboxamide;
N-(2,4-dichloro-6-(hydroxymethyl)benzyl)-5,6-dihydrofuro[2,3-d]thiazole-6-carboxamide;
N-(5,7-dichloro-2,3-dihydro-1H-inden-1-yl)-5,6-dihydrofuro[2,3-d]thiazole-6-carboxamide;
N-(2,4-dichloro-6-cyclopropylbenzyl)-5,6-dihydrofuro[2,3-d]thiazole-6-carboxamide;
N-(2-chloro-3-(trifluoromethyl)benzyl)-5,6-dihydrofuro[2,3-d]thiazole-6-carboxamide;
N-(3-chloro-2-(trifluoromethyl)benzyl)-5,6-dihydrofuro[2,3-d]thiazole-6-carboxamide;
N-(2,4-dichloro-6-((2-hydroxyethoxy)methyl)benzyl)-5,6-dihydrofuro[2,3-d]thiazole-6-carboxamide;
N-(4-phenoxybenzyl)-5,6-dihydrofuro[2,3-d]thiazole-6-carboxamide;
N-(2,4-dichlorobenzyl)-5,6-dihydro-4H-cyclopenta[d]thiazole-6-carboxamide;
N-(2-chloro-4-fluorobenzyl)-5,6-dihydro-4H-cyclopenta[d]thiazole-6-carboxamide;
N-(2-bromo-4,6-dichlorobenzyl)-5,6-dihydro-4H-cyclopenta[d]thiazole-6-carboxamide;
N-(2,4-dichloro-6-methylbenzyl)-5,6-dihydro-4H-cyclopenta[d]thiazole-6-carboxamide;
N-(2,4-dichlorophenethyl)-5,6-dihydro-4H-cyclopenta[d]thiazole-6-carboxamide;
N-(2-chloro-3-cyanobenzyl)-5,6-dihydro-4H-cyclopenta[d]thiazole-6-carboxamide;
N-(3-(2,4-dichlorophenyl)propyl)-5,6-dihydro-4H-cyclopenta[d]thiazole-6-carboxamide;
N-(1-(2,4-dichlorophenyl)-2-hydroxyethyl)-5,6-dihydro-4H-cyclopenta[d]thiazole-6-carboxamide;
N-(2,4-dichloro-6-(hydroxymethyl)benzyl)-5,6-dihydro-4H-cyclopenta[d]thiazole-6-carboxamide;
N-(2,4-dichloro-6-methoxybenzyl)-5,6-dihydro-4H-cyclopenta[d]thiazole-6-carboxamide;
N-(5,7-dichloro-2,3-dihydro-1H-inden-1-yl)-5,6-dihydro-4H-cyclopenta[d]thiazole-6-carboxamide;
N-(2-chloro-3-(trifluoromethyl)benzyl)-5,6-dihydro-4H-cyclopenta[d]thiazole-6-carboxamide;
N-(3-fluoro-4-(trifluoromethoxy)benzyl)-5,6-dihydro-4H-cyclopenta[d]thiazole-6-carboxamide;
N-(4-chlorobenzyl)-N-methyl-6,7-dihydro-5H-pyrano[2,3-d]thiazole-7-carboxamide;
N-(2,4-dichlorobenzyl)-6,7-dihydro-5H-pyrano[2,3-d]thiazole-7-carboxamide;
N-(2-chloro-4-fluorobenzyl)-6,7-dihydro-5H-pyrano[2,3-d]thiazole-7-carboxamide;
N-(2,3-dichlorobenzyl)-6,7-dihydro-5H-pyrano[2,3-d]thiazole-7-carboxamide;
N-(2,4-dichloro-6-methylbenzyl)-6,7-dihydro-5H-pyrano[2,3-d]thiazole-7-carboxamide;
N-(2,4-dichlorophenethyl)-6,7-dihydro-5H-pyrano[2,3-d]thiazole-7-carboxamide;
N-(2-chloro-3-cyanobenzyl)-6,7-dihydro-5H-pyrano[2,3-d]thiazole-7-carboxamide;
N-(4-(trifluoromethyl)benzyl)-6,7-dihydro-5H-pyrano[2,3-d]thiazole-7-carboxamide;
N-(3-(2,4-dichlorophenyl)propyl)-6,7-dihydro-5H-pyrano[2,3-d]thiazole-7-carboxamide;
N-((S)-1-(2,4-dichlorophenyl)-2-hydroxyethyl)-6,7-dihydro-5H-pyrano[2,3-d]thiazole-7-carboxamide;
N-(2,4-dichloro-6-(hydroxymethyl)benzyl)-6,7-dihydro-5H-pyrano[2,3-d]thiazole-7-carboxamide;
N-((S)-5,7-dichloro-2,3-dihydro-1H-inden-1-yl)-6,7-dihydro-5H-pyrano[2,3-d]thiazole-7-carboxamide;
N-(2-chloro-3-(trifluoromethyl)benzyl)-6,7-dihydro-5H-pyrano[2,3-d]thiazole-7-carboxamide;
N-(2,4-dichloro-6-(2-hydroxyethoxy)benzyl)-6,7-dihydro-5H-pyrano[2,3-d]thiazole-7-carboxamide;
N-(3-fluoro-4-(trifluoromethoxy)benzyl)-6,7-dihydro-5H-pyrano[2,3-d]thiazole-7-carboxamide;
N-(4-phenoxybenzyl)-6,7-dihydro-5H-pyrano[2,3-d]thiazole-7-carboxamide;
N-(4-chlorobenzyl)-4,5,6,7-tetrahydrobenzo[d]thiazole-7-carboxamide;
N-(4-chlorobenzyl)-N-methyl-4,5,6,7-tetrahydrobenzo[d]thiazole-7-carboxamide;
N-(3-chloro-2-methylbenzyl)-4,5,6,7-tetrahydrobenzo[d]thiazole-7-carboxamide;
2-amino-N-(2,4-dichlorobenzyl)-4,5,6,7-tetrahydrobenzo[d]thiazole-7-carboxamide;
N-(2,4-dichlorobenzyl)-2-methyl-4,5,6,7-tetrahydrobenzo[d]thiazole-7-carboxamide;
2-bromo-N-(2,4-dichlorobenzyl)-4,5,6,7-tetrahydrobenzo[d]thiazole-7-carboxamide;
N-(2,4-dichlorobenzyl)-4,5,6,7-tetrahydrobenzo[d]thiazole-7-carboxamide;

N-(2-chloro-4-fluorobenzyl)-4,5,6,7-tetrahydrobenzo[d]thiazole-7-carboxamide;
N-(2,3-dichlorobenzyl)-4,5,6,7-tetrahydrobenzo[d]thiazole-7-carboxamide;
N-(2,3-dihydro-1H-inden-1-yl)-4,5,6,7-tetrahydrobenzo[d]thiazole-7-carboxamide;
N-((R)-1-(2,4-dichlorophenyl)ethyl)-4,5,6,7-tetrahydrobenzo[d]thiazole-7-carboxamide;
N-(2,4-dichloro-6-methylbenzyl)-2-phenyl-4,5,6,7-tetrahydrobenzo[d]thiazole-7-carboxamide;
N-(2,4-dichloro-6-methylbenzyl)-2-(trifluoromethyl)-4,5,6,7-tetrahydrobenzo[d]thiazole-7-carboxamide;
2-amino-N-(2,4-dichloro-6-methylbenzyl)-4,5,6,7-tetrahydrobenzo[d]thiazole-7-carboxamide;
N-(2,4-dichloro-6-methylbenzyl)-2-methyl-4,5,6,7-tetrahydrobenzo[d]thiazole-7-carboxamide;
2-bromo-N-(2,4-dichloro-6-methylbenzyl)-4,5,6,7-tetrahydrobenzo[d]thiazole-7-carboxamide;
N-(2,4-dichloro-6-methylbenzyl)-4,5,6,7-tetrahydrobenzo[d]thiazole-7-carboxamide;
N-(2,4-dichlorophenethyl)-4,5,6,7-tetrahydrobenzo[d]thiazole-7-carboxamide;
N-((S)-1-(2,4-dichlorophenyl)-2-hydroxyethyl)-4,5,6,7-tetrahydrobenzo[d]thiazole-7-carboxamide;
N-(2,4-dichloro-6-(hydroxymethyl)benzyl)-4,5,6,7-tetrahydrobenzo[d]thiazole-7-carboxamide;
2-bromo-N-(2-chloro-3-(trifluoromethyl)benzyl)-4,5,6,7-tetrahydrobenzo[d]thiazole-7-carboxamide;
N-(2-chloro-3-(trifluoromethyl)benzyl)-4,5,6,7-tetrahydrobenzo[d]thiazole-7-carboxamide;
N-(2,4-dichloro-6-(methoxymethyl)benzyl)-4,5,6,7-tetrahydrobenzo[d]thiazole-7-carboxamide;
N-(3-fluoro-4-(trifluoromethoxy)benzyl)-4,5,6,7-tetrahydrobenzo[d]thiazole-7-carboxamide;
N-(4-phenoxybenzyl)-4,5,6,7-tetrahydrobenzo[d]thiazole-7-carboxamide;
2-amino-N-(2,4-dichlorobenzyl)-5,6,7,8-tetrahydro-4H-cyclohepta[d]thiazole-8-carboxamide;
N-(2,4-dichlorobenzyl)-5,6,7,8-tetrahydro-4H-cyclohepta[d]thiazole-8-carboxamide;
2-amino-N-(2,4-dichloro-6-methylbenzyl)-5,6,7,8-tetrahydro-4H-cyclohepta[d]thiazole-8-carboxamide;
N-(2,4-dichloro-6-methylbenzyl)-5,6,7,8-tetrahydro-4H-cyclohepta[d]thiazole-8-carboxamide;
(R)—N—((S)-1-(2,4-dichlorophenyl)-2-hydroxyethyl)-5,6,7,8-tetrahydro-4H-cyclohepta[d]thiazole-8-carboxamide; and
(S)—N—((S)-1-(2,4-dichlorophenyl)-2-hydroxyethyl)-5,6,7,8-tetrahydro-4H-cyclohepta[d]thiazole-8-carboxamide;
or a salt of such a compound.

11. A pharmaceutical composition containing, as active principle the compound of formula (I) according to claim 1, or a pharmaceutically acceptable salt thereof, and at least one therapeutically inert excipient.

12. A pharmaceutical composition containing, as active principle, a compound of formula (I) according to claim 10, or a pharmaceutically acceptable salt thereof, and at least one therapeutically inert excipient.

13. A method for the treatment of a disease selected from spinal cord injury, stroke, Alzheimer's disease, epilepsy, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, osteoporosis, and ischemic heart disease, comprising administering to a subject a pharmaceutically active amount of a compound according to claim 1, or a pharmaceutically acceptable salt thereof.

14. A method for the treatment of a disease selected from spinal cord injury, stroke, Alzheimer's disease, epilepsy, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, osteoporosis, and ischemic heart disease, comprising administering to a subject a pharmaceutically active amount of a compound according to claim 10, or a pharmaceutically acceptable salt thereof.

15. The compound of formula (I) according to claim 2, wherein
m represents 0;
or a salt of such a compound.

16. The compound of formula (I) according to claim 15, wherein
$R^1$ represents hydrogen and $R^2$ represents chloro;
or a salt of such a compound.

17. The compound of formula (I) according to claim 15, wherein
$R^1$ and $R^2$ together represent a —$CH_2CH_2$— group;
or a salt of such a compound.

18. The compound of formula (I) according to claim 15, wherein
$R^5$ represents hydrogen;
or a salt of such a compound.

19. The method of claim 13, wherein the disease is selected from spinal cord injury, Alzheimer's disease, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, and osteoporosis.

* * * * *

SEQUENCE LISTING

```
<160> NUMBER OF SEQ ID NOS: 2

<210> SEQ ID NO 1
<211> LENGTH: 35
<212> TYPE: DNA
<213> ORGANISM: Homo sapiens
<220> FEATURE:
<221> NAME/KEY: source
<222> LOCATION: 1..35
<223> OTHER INFORMATION: /mol_type="DNA"
      /organism="Homo sapiens"

<400> SEQUENCE: 1
atcgcggccg ctcagtaagg actcttgaag ccact                         35

<210> SEQ ID NO 2
<211> LENGTH: 38
<212> TYPE: DNA
<213> ORGANISM: Homo sapiens
<220> FEATURE:
<221> NAME/KEY: source
<222> LOCATION: 1..38
<223> OTHER INFORMATION: /mol_type="DNA"
      /organism="Homo sapiens"

<400> SEQUENCE: 2
cgccgctagc accaccatgc cggcctgctg cagctgca                      38
```